US007838648B2

(12) United States Patent
Caput et al.

(10) Patent No.: US 7,838,648 B2
(45) Date of Patent: Nov. 23, 2010

(54) PURIFIED SR-P70 PROTEIN

(75) Inventors: Daniel Caput, Labege (FR); Pascual Ferrara, Avignonet Lauragais (FR); Ahmed Mourad Kaghad, Montgiscard (FR)

(73) Assignee: Sanofi Aventis, Paris (FR)

( * ) Notice: Subject to any disclaimer, the term of this patent is extended or adjusted under 35 U.S.C. 154(b) by 0 days.

(21) Appl. No.: 12/464,274

(22) Filed: May 12, 2009

(65) Prior Publication Data

US 2009/0258409 A1 Oct. 15, 2009

Related U.S. Application Data

(60) Division of application No. 11/122,636, filed on May 5, 2005, now Pat. No. 7,557,187, which is a continuation of application No. 09/125,005, filed as application No. PCT/FR97/00214 on Feb. 3, 1997, now abandoned.

(30) Foreign Application Priority Data

Feb. 2, 1996 (FR) .................................. 96 01309

(51) Int. Cl.
C07H 21/02 (2006.01)
C07H 21/04 (2006.01)
C12N 5/00 (2006.01)
C12N 1/21 (2006.01)
C12N 15/00 (2006.01)

(52) U.S. Cl. ..................... 536/23.1; 536/23.5; 435/325; 435/252.3; 435/252.33; 435/320.1

(58) Field of Classification Search ........................ None
See application file for complete search history.

(56) References Cited

U.S. PATENT DOCUMENTS 5,532,348 A   7/1996  Huibregise et al.
5,912,143 A * 6/1999  Bandman et al. ........... 435/69.1
6,451,979 B1  9/2002  Kaelin

FOREIGN PATENT DOCUMENTS

EP    0 377 295       7/1990
WO    WO94/01563     1/1994
WO    WO94/08241     4/1994
WO    WO99/66946    12/1999

OTHER PUBLICATIONS

Matsushita et al. (FEBS Letters, 1999, vol. 443, pp. 348-352).*
Singh et al. (Glycobiology, 2001, vol. 11, pp. 587-592).*
Alberts et al., Molecular Biology of the Cell, 3rd ed., 1994, p. 465.
Arai et al., Immunologically distinct p53 molecules generated by alternative splicing, Mol. Cell. Biol., Sep. 1986, vol. 6. No. 9, pp. 3232-3239.
B. Curti, Physical barriers to drug delivery in tumors, Critical Reviews in Oncology/Hematology, 1993, pp. 29-39.

Benedict et al., The Long Isoform of Terminal Deoxynucleotidyl Transferase Enters the Nucleus and, Rather than Catalyzing Nontemplated Nucleotide . . . , J. of Exp. Medicine, 2001, vol. 193, No. 1., pp. 89-99.
Bodrug et al., Molecular analysis of a constitutional X-autosome translocation in a female with muscular dystrophy, Science, vol. 237, 1987, pp. 1620-1624.
Bork, P., Powers and Pitfalls in Sequence Analysis: The 70% Hurdle, Genome Research, 2000, vol. 10, pp. 398-400.
Bowie et al., Deciphering the Message in Protein Sequences: Tolerance to Amino Acid Substitutions, Science, 1990, vol. 247, pp. 1306-1310.
Burgess et al., Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue, J. of Cell Bio. 1990, vol. 111, pp. 2129-2138.
Dequiedt et al., DNA Seq. 5, 1995, pp. 255-259.
Dequiedt et al., See Score 20060927_162151_us-11-122-636-6_ copy_110_310.rup database Sequence search, Result 38, DNA Seq, 1995,5: 261-264.
Frasca et al., p73 Tumor-Suppressor Activity Is Impaired in Human Thyroid Cancer, Cancer Research, vol. 63, Sep. 15, 2003, pp. 5829-5837.
Fu et al., Translational regulation of human p53 g in Expression, EMBO Journal, 1996, vol. 15, pp. 4392-4401.
H. Drexler, Recent Results on the Biology of Hodgkin and Reed-Sternberg cells, Leukemia and Lymphoma, 1993, vol. 9, pp. 1-25.
Hartwell et al., Integrating Genetic Approaches into the Discovery of Anticancer Drugs, Science, Nov. 7, 1997, vol. 278, pp. 1064-1068.
Hirashima et al., Ecalectin/Galectin-9, a Novel Eosinophil Chemoattractant: Its Function and Production. Int. Arch. Allergy Immunol., 2000, Suppl. 1, pp. 6-9.
Ichimiya et al., p73: Structure and Function, Pathol Int. Aug. 2000, vol. 50, No. 8, pp. 589-593.
Ikawa et al., p53 family genes: structural comparison, expression and mutation, Cell Death and Differentiation, 1999, vol. 6, pp. 1154-1161.
Iwase et al., Identification of protein-tyrosine kinase gnes preferentially expressed in embryo stomach and gastric cancer, Biochem Biophys Res. Commun.
Jansen et al., Translational Control of Gene Expression, Pediatric Res. 1995, vol. 37, No. 6, pp. 681-686.
Jiang et al., Smooth Muscle Tissues Express a Major Dominant Negative Spice Varian of the Type 3 Ca2' Release Channel (Ryanodine Receptor), J. of Bio. Chem., 2003, vol. 278, No. 7, pp. 4763-4769.
Kaghad et al., Monoallelically Expressed Gene Related to p53 at 1p36, a Region Frequently Deleted in Neuroblastoma and Other Human Cancers, Cell, Aug. 22, 1997, vol. 90, pp. 809-819.
Lazar et al., Transforming Growth Factor alpha: Mutation of Aspartic Acid 47 and Leucine 48 Results in Different Biological Activities, Mol. & Cell. Biol., Mar. 1988, vol. 8, No. 3, pp. 1247-1252.
M. Embleton, Monoclonal Antibodies to Osteogenic Sarcoma Antigens, Immunol. Ser. 1984, pp. 181-207.
McClean et al., Evidence of Post-translational Regulation of P-Glycoprotein Associated with the Expression of a Distinctive Multiple Drug-resistant Phenotype in Chinese Hamster Ovary Cells, Eur. J. Cancer, 1993, vol. 29A, pp. 2243-2248.

(Continued)

Primary Examiner—Peter J Reddig

(57) ABSTRACT

The invention relates to new nucleic acid sequences of the family of tumor-suppressing genes related to the gene for the p53 protein, and to corresponding protein sequences.

7 Claims, 36 Drawing Sheets

OTHER PUBLICATIONS

Neumann et al., Multifactorial inheritance of neural tube defects: localization of the major gene and recognition of modifiers in ct mutant mice, Nature Genetics, 1994, vol. 6, pp. 357-362.

P. Bork, Powers and Pitfalls in Sequence Analysis: the 70% Hurdle, Genome Research, 2000, vol. 10, pp. 398-400.

Puig et al., p73 Expressio in Human Normal and Tumor Tissues: Loss of p73 alpa Expression is Associated with Tumor Progession in Bladder Cancer, Cancer Research, Nov. 15, 2003, vol. 9, pp. 5652-5651.

R. Jain, Barriers to Drug Delivery in Solid Tumors, Scientific American, Jul. 1994, pp. 58-65.

Scott et al., The Pendered syndrom gene encodes a chloride-iodide transport protein, Nature Genetics, 1999, vol. 21, pp. 440-443.

Shantz et al., Translational regulation of ornithine decarboxylase and other enzymes of the polyamine pathway, Int. J. Biochem and Cell Biol. 1999, vol. 31, pp. 107-122.

Soussi et al., Nucleotide sequence of a cDNA encoding the chicken p53 nuclear protein, Nucleic Acid Research, 1998, vol. 16, No. 23, p. 1183.

T. Gura, Systems for Identifying New Drugs Are Often Faulty, Science, Nov. 7, 1997, vol. 278, pp. 1041-1042.

T.C. Hsu, Karyology of Cells in Culture, Tissue Culture Methods and Applications, Kruse and Patterson Eds. 1973, Academic Press, NY, see abstract p. 764.

Tominaga et al., Detection of p73 antibodies in patients with various types of cancer: immunological characterization, Br. J. of Cancer, 2001, vol. 84, No. 1, pp. 57-63.

Wilson et al., 2.2 Mb of continguous nucleotide sequence from chromosome III of C. elegans, Nature, vol. 368, pp. 32-38.

Zellner et al., Disparity in Expression of Protein Kinase C alpha in Human Glioma versus Glioma-derived Primary Cell Lines: Therapeutic Implications, Clin. Can. Res. 1998, vol. 4, pp. 1797-1802.

* cited by examiner

```
  1 TGCCTCCCCGCCCGCGCACCCGCCCCGAGGCCTGTGCTCCTGCGAAGGGG  50
                                      ||  ||||
  1 ................................GGGGCTCCGGGG  12

51 ACGCAGCGAAGCCGGGGCCCGCGCCAGGCCGGCCGGGACGGACGCCGATG 100
    ||| |  |||||   ||  |  |     ||   |   |  |
 13 ACACTTGGCGTCCGGGCTGGAAGCGTGCTTTCCAAGACGGTGACACGCTT  62

101 CCCGGAGCTGCGACGGCTGCAGAGCGAGCTGCCCTCGGAGGCCGGTGTGA 150
    || |||    |||  |   || |||  |||  |        |||| ||
 63 CCCTGAGGATTGGCAGCCAGACTGCTTACGGGTCAC...TGCCATGGAGG 109

151 GGAAGATGGCCCAGTCCACCACCACCTCCCCGATGGGGCACCACGTTT   200
     ||  ||   ||| |  |||   |||   ||  |    |    || |||
110 AGCCGCAGTCAGATCCCAGCATCGAGCCCCTCTGAGTCAGGAAACATTT  159

201 GAGCACCTCTGGAGCTCTCTGGAACCAGACAGCACCTACTTCGACCTTCC 250
     | |  |||| ||   ||    |||| ||    || ||||| |||  |
160 TCAGACCTATGGAAACTACTTCCTGAAAACAAC.GTTCTGTCCCCCTTGC 208

251 CCAGTCAAGCCGGGGGAATAATGAGGTGGTGGGTGGCACGGATTCCAGCA 300
     | ||||||| |  |||  ||   |||| |  ||  |   ||    ||
209 CGTCCCAAGCGGTGGATGATTTGATGCTCTCTCCGGATGATCTTGCACAA 258

301 TGGACGTCTTCCACCTAGAGGGCATGACCACATCTGTCATGGCCCAGTTC 350
    |||                          |  | |  ||||||  ||
259 TGG...................TTAACTGAAGACCCAGGTC 280

351 AATTTGCTGAGCAGCACCATGGACCAGATGAGCAGCCGCGCTGCCTCGGC 400
     |  ||| |                |||||       ||||||
281 CAGATGAAGCTC..........CCAGAATGTCAGAGGCTGCTCCCCACA 319

401 CAGCCCGTACACCCCGGAGCACGCCGCCAGCGTGCCCACCCATTCACCCT 450
    ||| ||    |||||    |   ||  || |   |  ||||     ||
320 TGGCCCCCACACCAGCAGCTCCTACACCGGCGGCCCCTGCACCAGCCCC. 368

451 ACGCACAGCCCAGCTCCACCTTCGACACCATGTCGCCCGCGCCTGTCATC 500
          |||   |  |   ||| | | | | ||     |    |||||
369 ...........CTCCTGGCCCCTGTCATCCTCTGTC 393

501 CCCTCCAACACCGACTATCCCGGACCCCACCACTTCGAGGTCACTTTCCA 550
     |  |||||   ||  ||| | ||  ||   || || || | |  || ||
394 CCTTCCCAGAAAACCTACCACGGCAGCTACGGTTTCCGTCTGGGCTTCCT 443

551 GCAGTCCAGCACGGCCAAGTCAGCCACCTGGACGTACTCCCCACTCTTGA 600
    |||  || || ||||||||| |||  || |||||||||||| || ||
444 GCATTCTGGAACAGCCAAGTCTGTGACTTGCACGTACTCCCCTGACCTCA 493

601 AGAAACTCTACTGCCAGATCGCCAAGACATGCCCCATCCAGATCAAGGTG 650
    | ||  |  |  |||||| | ||||||| |||| ||||  |||| |||
494 ACAAGATGTTTTGCCAGCTGGCCAAGACCTGCCCCGTGCAGCTGTGGGTT 543

651 TCCGCCCCACCGCCCCCGGGCACCGCCATCCGGGCCATGCCTGTCTACAA 700
     || | ||  |  ||| ||||||| || || || ||| |||||| ||||
544 GATTCCACACCCCGCCCGGCAGCCGCGTCCGCGCCATGGCCATCTACAA 593

701 GAAGGCGGAGCACGTGACCGACATCGTGAAGCGCTGCCCCAACCACGAGC 750
    |  |   |  |||| |||| |  ||||||| ||||||||| ||||  ||
594 GCAGTCACAGCACATGACTGAGGTCGTGAGGCGCTGCCCCCACCATGAGC 643

751 TCGGGAGGGACTTCAACGAAGGACAGTCTGCCCCAGCCAGCCACCTCATC 800
     | |  |||   | | |              |||||  |  ||  |  |
644 GCTGCTCAGACAGCGATGGA......CTGGCCCCTCCTCAACATCTTATC 687

801 CGTGTGGAAGGCAATAATCTCTCGCAGTATGTGGACGACCCTGTCACCGG 850
    ||||||||||| |||||    |     | ||||| ||| || |   ||
688 CGAGTGGAAGGAAATTTGCGTGTGGAGTATTCGGATGACAGAAACACTTT 737

851 CAGGCAGAGCGTCGTGGTGCCCTATGAGCCACCACAGGTGGGGACAGAAT 900
     ||  ||| ||| |||||||||||||||||||||| ||  |||| | |||
738 TCGACATAGTGTGGTGGTGCCCTATGAGCCGCCTGAGGTTGGCTCTGACT 787
```

FIG. 1A

```
901  TCACCACCATCCTGTACAACTTCATGTGTAACAGCAGCTGTGTGGGGGC 950
     ||||||||| |||||| |||||||||| || ||| |||
788  GTACCACCATCCACTACAACTACATGTGTAACAGTTCCTGCATGGGCGGC 837

951  ATGAACCGACGGCCCATCCTCATCATCATCACCCTGGAGACGCGGGATGG 1000
     |||||||  ||||||||||||| || |||||| |||||        |||
838  ATGAACCGGAGGCCCATCCTCACAATTATCACACTGGAAGACTCCAGTGG 887

1001 GCAGGTGCTGGGCCGCCGGTCCTTCGAGGGCCGCATCTGCGCCTGTCCTG 1050
     |  |  |||| |   |||  |  || || ||  ||||||||||||||||
888  TAATCTACTGGGACGGAACAGCTTTGAGGTGCGAGTTTGTGCCTGTCCTG 937

1051 GCCGCGACCGAAAAGCCGATGAGGACCACTACCGGGAGCAGCAGGCCTTG 1100
     |  | ||||| |  | || || || |  | |                 |
938  GGAGAGACCGGCGCACAGAGGAAGAGAATTTCC................G 971

1101 AATGAGAGCTCCGCCAAGAACGGGGCTGCCAGCAAGCGCGCCTTCAAGCA 1150
     | | ||   |||  |  | ||||||  ||    ||  ||   |
972  CAAGAAAGGGGAGCCTTGCCACGAGCTGCCCCCTGGAGCACTAAGCGAG 1021

1151 GAGTCCCCCTGCCGTCCCCGCCCTGGGCCC.GGGTGTGAAGAAGCGGCGG 1199
     |  | ||   ||     |||     |||     ||||| | ||  || ||
1022 CACTGCCCAACAACACCAGCTCCTCTCCCCAGCCAAAGAAGAAACCACTG 1071

1200 CACGGAGACGAGGACACGTACTACCTGCAGGTGCGAGGCCGCGAGAACTT 1249
     | ||||| |   |||    ||| || | || || ||  ||   |||  ||
1072 GATGGAGAATATTTCAC......CCTTCAGATCCGCGGCGTGAGCGCTT 1115

1250 CGAGATCCTGATGAAGCTGAAGGAGAGCCTGGAGCTGATGGAGTTGGTGC 1299
     ||||||    |  |||||||  ||||||  |||  |  | |
1116 CGAGATGTTCCGAGAGCTGAATGAGGCCTTGGAACTCAAGGA........ 1157

1300 CGCAGCCGCTGGTAGACTCCTATCGGCAGCAGCAGCAGCTCCTACAGAGG 1349
     ||   |||||       |    |    |||  | |||||  || |||
1158 TGCCCAGGCTGGGAAAGAGCCAGCGG..GGAGCAGGGCTCACTCCAGCCA 1205

1350 CCGAGTCACCTACAGCCCCCATCCTACGGGCCGGTCCTCTCGCCCATGAA 1399
     ||   | ||    ||  ||  ||    ||| ||  ||
1206 CCTGAAGTCCAAGAAGGGGCAATCTACCTCCCGCCATAAAAAATTCATGT 1255

1400 CAAGGTGCACGGGGGCGTGAACAAGCTGCCCTCCGTCAACCAGCTGGTGG 1449
     | ||       |||| |    ||  || |||        |||| || ||
1256 TCAAGACAGAGGGGCCTGACTCAGACTGACATTC.....TCAGCTTCTTG 1300

1450 GCCAGCCTCCCCCGCACAGCTCGGCAGCTACACCCAACCTGGGACCTGTG 1499
     |  |  ||       || ||  ||  |    ||| ||    |    |||
1301 TTCCCCCACTGAGCCTCCCACCCCCATCT.CTCCCTCCCTGCCATTTTG 1349

1500 GGCTCTGGGATGCTCAACAACCACGGCCACGCAGTGCCAGCCAACAGCGA 1549
     | |||||     |||    |||    |  || ||    |   |||
1350 AGTTCTGGGTCTTTAAACCCTTGCTTGCAATAGGTGTGTGTCAGAAGCAA 1399

1550 GATGACCAGCAGCCACGGCACCCAGTCCATGGTCTCGGGGTCCCACTGCA 1599

```
  1 MAQSTTTSPDGGTTFEHLWSSLEPDSTYFDLPQSSRGNNEVVGGTDSSHD  50
    ..|::::..:|. :|    :.|: ||.  .:||:....:|
  1 .....MEEPQSDPSIEPPLS....QETFSDLWKLLPENNVLSPLPSQAVD  41

51 VFHLEGMTTSVHAQFNLLSSTMDQHSSRAASASPYTPEHAASVPTHSPYA 100
    : |   ...:|||:    ...|:......|...|..||..|. .|.:.
 42 DLML...SPDDLAQWLTEDPGPDEAPRMSEAAPHMAPTPAAPTPA.APAP  87

101 QPSSTFDTMSPAPVIPSNTDYPGPHHFEVTFQQSSTAKSATWTYSPLLKK 150
    .||...:     .. :||...|.|..  |:.|:|:||||.| |||| |.|
 88 APSWPL.....SSSVPSQKTYHGSYGFRLGFLHSGTAKSVTCTYSPDLNK 132

151 LYCQIAKTCPIQIKVSAPPPPGTAIRAMPVYKKAEHVTDIVKRCPNHELG 200
    :;||:|||||:|:,|...||||. :|||::||::||::|:||||:|
133 MFCQLAKTCPVQLWVDSTPPPGSRVRAMAIYKQSQHMTEVVRRCPHHE.. 180

201 RDFNEGQSAPASHLIRVEGNNLSQYVDDPVTGRQSVVVPYEPPQVGTEFT 250
    |  :.:. ||: ||||||||   :| ||.| |:||||||||:||.:  |
181 RCSDSDGLAPPQHLIRVEGNLRVEYSDDRNTFRHSVVVPYEPPEVGSDCT 230

251 TILYNFMCNSSCVGGMNRRPILIIITLETRDGQVLGRRSFEGRICACPGR 300
    || ||:||||||:|||||||||.||||...|.:|||.|||.|:||||||
231 TIHYNYMCNSSCMGGHNRRPILTIITLEDSSGNLLGRNSFEVRVCACPGR 280

301 DRKADEDHYREQQALNESSAKNGAAASKRAFKQSPPAVPALGPGVKKRRHG 350
    ||:..:|:::|... :,: . .:...|||:......|.    .|:;.
281 DRRTEEENFRKKG..EPCHELPPGSTKRALPNNTSSSPQ.....PKKKPL 323

351 DEDTYYLQVRGRENFEILHKLKESLELHELVPQPLVDSYRQQQQLLQRPS 400
    |:: : ||:|||| ||:..|.|.||| |.|:    ..:  |.:   |....
324 DGEYFTLQIRGRERFEMFRELNEALELKDAQAGKEPAGSRAHSSHLKSKK 373

401 HLQPPSYGPVLSPHNKVHGGVNKLPSVNQLVGQPPPHSSAATPNLGFVGS 450
    .... ..: . ..:|
374 GQSTSRHKKFMFKTEGPDSD.............................  393
```

FIG.2

```
  1 TGCCTCCCCGCCCGCGCACCCGCCCCGAGGCCTGTGCTCCTGCGAAGGGG  50
    ||||||||||||||||||||||||||||||||||||||||||||||||||
  1 TGCCTCCCCGCCCGCGCACCCGCCCCGAGGCCTGTGCTCCTGCGAAGGGG  50

51 ACGCAGCGAAGCCGGGGCCCGCGCCAGGCCGGCCGGGACGGACGCCGATG 100
    ||||||||||||||||||||||||||||||||||||||||||||||||||
 51 ACGCAGCGAAGCCGGGGCCCGCGCCAGGCCGGCCGGGACGGACGCCGATG 100

101 CCCGGAGCTGCGACGGCTGCAGAGCGAGCTGCCCTCGGAGGCCGGTGTGA 150
    ||||||||||||||||||||||||||||||||||||||||||||||||||
101 CCCGGAGCTGCGACGGCTGCAGAGCGAGCTGCCCTCGGAGGCCGGTGTGA 150

151 GGAAGATGGCCCAGTCCACCACCACCTCCCCCGATGGGGGCACCACGTTT 200
    ||||||||||||||||||||||||||||||||||||||||||||||||||
151 GGAAGATGGCCCAGTCCACCACCACCTCCCCCGATGGGGGCACCACGTTT 200

201 GAGCACCTCTGGAGCTCTCTGGAACCAGACAGCACCTACTTCGACCTTCC 250
    ||||||||||||||||||||||||||||||||||||||||||||||||||
201 GAGCACCTCTGGAGCTCTCTGGAACCAGACAGCACCTACTTCGACCTTCC 250

251 CCAGTCAAGCCGGGGGAATAATGAGGTGGTGGGTGGCACGGATTCCAGCA 300
    ||||||||||||||||||||||||||||||||||||||||||||||||||
251 CCAGTCAAGCCGGGGGAATAATGAGGTGGTGGGTGGCACGGATTCCAGCA 300

301 TGGACGTCTTCCACCTAGAGGGCATGACCACATCTGTCATGGCCCAGTTC 350
    ||||||||||||||||||||||||||||||||||||||||||||||||||
301 TGGACGTCTTCCACCTAGAGGGCATGACCACATCTGTCATGGCCCAGTTC 350

351 AATTTGCTGAGCAGCACCATGGACCAGATGAGCAGCCGCGCTGCCTCGGC 400
    ||||||||||||||||||||||||||||||||||||||||||||||||||
351 AATTTGCTGAGCAGCACCATGGACCAGATGAGCAGCCGCGCTGCCTCGGC 400

401 CAGCCCGTACACCCCGGAGCACGCCGCCAGCGTGCCCACCCATTCACCCT 450
    ||||||||||||||||||||||||||||||||||||||||||||||||||
401 CAGCCCGTACACCCCGGAGCACGCCGCCAGCGTGCCCACCCATTCACCCT 450

451 ACGCACAGCCCAGCTCCACCTTCGACACCATGTCGCCCGCGCCTGTCATC 500
    ||||||||||||||||||||||||||||||||||||||||||||||||||
451 ACGCACAGCCCAGCTCCACCTTCGACACCATGTCGCCCGCGCCTGTCATC 500

501 CCCTCCAACACCGACTATCCCGGACCCCACCACTTCGAGGTCACTTTCCA 550
    ||||||||||||||||||||||||||||||||||||||||||||||||||
501 CCCTCCAACACCGACTATCCCGGACCCCACCACTTCGAGGTCACTTTCCA 550

551 GCAGTCCAGCACGGCCAAGTCAGCCACCTGGACGTACTCCCCACTCTTGA 600
    ||||||||||||||||||||||||||||||||||||||||||||||||||
551 GCAGTCCAGCACGGCCAAGTCAGCCACCTGGACGTACTCCCCACTCTTGA 600

601 AGAAACTCTACTGCCAGATCGCCAAGACATGCCCCATCCAGATCAAGGTG 650
    ||||||||||||||||||||||||||||||||||||||||||||||||||
601 AGAAACTCTACTGCCAGATCGCCAAGACATGCCCCATCCAGATCAAGGTG 650

651 TCCGCCCCACCGCCCCCGGGCACCGCCATCCGGGCCATGCCTGTCTACAA 700
    ||||||||||||||||||||||||||||||||||||||||||||||||||
651 TCCGCCCCACCGCCCCCGGGCACCGCCATCCGGGCCATGCCTGTCTACAA 700

701 GAAGGCGGAGCACGTGACCGACATCGTGAAGCGCTGCCCCAACCACGAGC 750
    ||||||||||||||||||||||||||||||||||||||||||||||||||
701 GAAGGCGGAGCACGTGACCGACATCGTGAAGCGCTGCCCCAACCACGAGC 750

751 TCGGGAGGGACTTCAACGAAGGACAGTCTGCCCCAGCCAGCCACCTCATC 800
    ||||||||||||||||||||||||||||||||||||||||||||||||||
751 TCGGGAGGGACTTCAACGAAGGACAGTCTGCCCCAGCCAGCCACCTCATC 800

801 CGTGTGGAAGGCAATAATCTCTCGCAGTATGTGGACGACCCTGTCACCGG 850
    ||||||||||||||||||||||||||||||||||||||||||||||||||
801 CGTGTGGAAGGCAATAATCTCTCGCAGTATGTGGACGACCCTGTCACCGG 850

851 CAGGCAGAGCGTCCTGGTGCCCTATGAGCCACCACAGGTGGGGACAGAAT 900
    ||||||||||||||||||||||||||||||||||||||||||||||||||
851 CAGGCAGAGCGTCGTGGTGCCCTATGAGCCACCACAGGTGGGGACAGAAT 900
```

FIG. 3A

```
901  TCACCACCATCCTGTACAACTTCATGTGTAACAGCAGCTGTGTGGGGGC  950
     ||||||||||||||||||||||||||||||||||||||||||||||||
901  TCACCACCATCCTGTACAACTTCATGTGTAACAGCAGCTGTGTGGGGGC  950

951  ATGAACCGACGGCCCATCCTCATCATCATCACCCTGGAGACGCGGGATGG 1000
     ||||||||||||||||||||||||||||||||||||||||||||||||
951  ATGAACCGACGGCCCATCCTCATCATCATCACCCTGGAGACGCGGGATGG 1000

1001 GCAGGTGCTGGGCCGCCGGTCCTTCGAGGGCCGCATCTGCGCCTGTCCTG 1050
     ||||||||||||||||||||||||||||||||||||||||||||||||
1001 GCAGGTGCTGGGCCGCCGGTCCTTCGAGGGCCGCATCTGCGCCTGTCCTG 1050

1051 GCCGCGACCGAAAAGCCGATGAGGACCACTACCGGGAGCAGCAGGCCTTG 1100
     ||||||||||||||||||||||||||||||||||||||||||||||||
1051 GCCGCGACCGAAAAGCCGATGAGGACCACTACCGGGAGCAGCAGGCCTTG 1100

1101 AATGAGAGCTCCGCCAAGAACGGGGCTGCCAGCAAGCGCGCCTTCAAGCA 1150
     ||||||||||||||||||||||||||||||||||||||||||||||||
1101 AATGAGAGCTCCGCCAAGAACGGGGCTGCCAGCAAGCGCGCCTTCAAGCA 1150

1151 GAGTCCCCCTGCCGTCCCCGCCCTGGGCCCGGGTGTGAAGAAGCGGCGGC 1200
     ||||||||||||||||||||||||||||||||||||||||||||||||
1151 GAGTCCCCCTGCCGTCCCCGCCCTGGGCCCGGGTGTGAAGAAGCGGCGGC 1200

1201 ACGGAGACGAGGACACGTACTACCTGCAGGTGCGAGGCCGCGAGAACTTC 1250
     ||||||||||||||||||||||||||||||||||||||||||||||||
1201 ACGGAGACGAGGACACGTACTACCTGCAGGTGCGAGGCCGCGAGAACTTC 1250

1251 GAGATCCTGATGAAGCTGAAGGAGAGCCTGGAGCTGATGGAGTTGGTGCC 1300
     ||||||||||||||||||||||||||||||||||||||||||||||||
1251 GAGATCCTGATGAAGCTGAAGGAGAGCCTGGAGCTGATGGAGTTGGTGCC 1300

1301 GCAGCCGCTGGTAGACTCCTATCGGCAGCAGCAGCAGCTCCTACAGAGGC 1350
     ||||||||||||||||||||||||||||||||||||||||||||||||
1301 GCAGCCGCTGGTAGACTCCTATCGGCAGCAGCAGCAGCTCCTACAGAGGC 1350

1351 CGAGTCACCTACAGCCCCCATCCTACGGGCCGGTCCTCTCGCCCATGAAC 1400
     ||||||||||||||||||||||||||||||||||||||||||||||||
1351 CGAGTCACCTACAGCCCCCATCCTACGGGCCGGTCCTCTCGCCCATGAAC 1400

1401 AAGGTGCACGGGGGCGTGAACAAGCTGCCCTCCGTCAACCAGCTGGTGGG 1450
     ||||||||||||||||||||||||||||||||||||||||||||||||
1401 AAGGTGCACGGGGGCGTGAACAAGCTGCCCTCCGTCAACCAGCTGGTGGG 1450

1451 CCAGCCTCCCCCGCACAGCTCGGCAGCTACACCCAACCTGGGACCTGTGG 1500
     ||||||||||||||||||||||||||||||||||||||||||||||||
1451 CCAGCCTCCCCCGCACAGCTCGGCAGCTACACCCAACCTGGGACCTGTGG 1500

1501 GCTCTGGGATGCTCAACAACCACGGCCACGCAGTGCCAGCCAACAGCGAG 1550
     ||||||||||||||||||||||||||||||||||||||||||||||||
1501 GCTCTGGGATGCTCAACAACCACGGCCACGCAGTGCCAGCCAACAGCGAG 1550

1551 ATGACCAGCAGCCACGGCACCCAGTCCATGGTCTCGGGGTCCCACTGCAC 1600
     ||||||||||||||||||||||||||||||||||||||||||||||||
1551 ATGACCAGCAGCCACGGCACCCAGTCCATGGTCTCGGGGTCCCACTGCAC 1600

1601 TCCGCCACCCCCTACCACGCCGACCCCAGCCTCGTCAGTTTTTTAACAG 1650
     ||||||||||||||||||||||||||||||||||||
1601 TCCGCCACCCCCTACCACGCCGACCCCAGCCTCGTC............. 1637

1701 AGCATTTACCACCTGCAGAACCTGACCATCGAGGACCTGGGGGCCCTGAA 1750
                                       ||||||||||||||||
1638 ..................................AGGACCTGGGGGCCCTGAA 1656

1751 GATCCCCGAGCAGTATCGCATGACCATCTGGCGGGCCTGCAGGACCTGA 1800
     |||||||||||||||||||||||||||||||||||||||||||||||||
```

FIG. 3B

```
1657 GATCCCCGAGCAGTATCGCATGACCATCTGGCGGGCCTGCAGGACCTGA 1706

1801 AGCAGGGCCACGACTACGGCGCCGCCGCGCAGCAGCTGCTCCGCTCCAGC 1850
     ||||||||||||||||||||||||||||||||||||||||||||||||||
1707 AGCAGGGCCACGACTACGGCGCCGCCGCGCAGCAGCTGCTCCGCTCCAGC 1756

1851 AACGCGGCCGCCATTTCCATCGGCGGCTCCGGGGAGCTGCAGCGCCAGCG 1900
     ||||||||||||||||||||||||||||||||||||||||||||||||||
1757 AACGCGGCCGCCATTTCCATCGGCGGCTCCGGGGAGCTGCAGCGCCAGCG 1806

1901 GGTCATGGAGGCCGTGCACTTCCGCGTGCGCCACACCATCACCATCCCCA 1950
     ||||||||||||||||||||||||||||||||||||||||||||||||||
1807 GGTCATGGAGGCCGTGCACTTCCGCGTGCGCCACACCATCACCATCCCCA 1856

1951 ACCGCGGCGGCCCCGGCGCCGGCCCCGACGAGTGGGCGGACTTCGGCTTC 2000
     ||||||||||||||||||||||||||||||||||||||||||||||||||
1857 ACCGCGGCGGCCCCGGCGCCGGCCCCGACGAGTGGGCGGACTTCGGCTTC 1906

2001 GACCTGCCCGACTGCAAGGCCCGCAAGCAGCCCATCAAGGAGGAGTTCAC 2050
     ||||||||||||||||||||||||||||||||||||||||||||||||||
1907 GACCTGCCCGACTGCAAGGCCCGCAAGCAGCCCATCAAGGAGGAGTTCAC 1956

2051 GGAGGCCGAGATCCACTGAGGGGCCGGGCCCAGCCAGAGCCTGTGCCACC 2100
     ||||||||||||||||||||||||||||||||||||||||||||||||||
1957 GGAGGCCGAGATCCACTGAGGGGCCGGGCCCAGCCAGAGCCTGTGCCACC 2006

2101 GCCCAGAGACCCAGGCCGCCTCGCTCTC 2128
     ||||||||||||||||||||||||||||
2007 GCCCAGAGACCCAGGCCGCCTCGCTCTC 2034
```

FIG. 3C

```
   1 TGCCTCCCCGCCCGCGCACCCGCCCCGAGGCCTGTGCTCCTGCGAAGGGGACGCAGCGAA   60
  61 GCCGGGGCCCGCGCCAGGCCGGCCGGGACGGACGCCGATGCCCGGAGCTGCGACGGCTGC  120
 121 AGAGCGAGCTGCCCTCGGAGGCCGGTGTGAGGAAGATGGCCCAGTCCACCACCACCTCCC  180
 -10                                    M  A  Q  S  T  T  T  S  P    9
 181 CCGATGGGGGCACCACGTTTGAGCACCTCTGGAGCTCTCTGGAACCAGACAGCACCTACT  240
  10  D  G  G  T  T  F  E  H  L  W  S  S  L  E  P  D  S  T  Y  F   29
 241 TCGACCTTCCCCAGTCAAGCCGGGGGAATAATGAGGTGGTGGGTGGCACGGATTCCAGCA  300
  30  D  L  P  Q  S  S  R  G  N  N  E  V  V  G  G  T  D  S  S  M   49
 301 TGGACGTCTTCCACCTAGAGGGCATGACCACATCTGTCATGGCCCAGTTCAATTTGCTGA  360
  50  D  V  F  H  L  E  G  M  T  T  S  V  M  A  Q  F  N  L  L  S   69
 361 GCAGCACCATGGACCAGATGAGCAGCCGCGCTGCCTCGGCCAGCCCGTACACCCCGGAGC  420
  70  S  T  M  D  Q  M  S  S  R  A  A  S  A  S  P  Y  T  P  E  H   89
 421 ACGCCGCCAGCGTGCCCACCCATTCACCCTACGCACAGCCCAGCTCCACCTTCGACACCA  480
  90  A  A  S  V  P  T  H  S  P  Y  A  Q  P  S  S  T  F  D  T  M  109
 481 TGTCGCCCGCGCCTGTCATCCCCTCCAACACCGACTATCCCGGACCCCACCACTTCGAGG  540
 110  S  P  A  P  V  I  P  S  N  T  D  Y  P  G  P  H  H  F  E  V  129
 541 TCACTTTCCAGCAGTCCAGCACGGCCAAGTCAGCCACCTGGACGTACTCCCCACTCTTGA  600
 130  T  F  Q  Q  S  S  T  A  K  S  A  T  W  T  Y  S  P  L  L  K  149
 601 AGAAACTCTACTGCCAGATCGCCAAGACATGCCCCATCCAGATCAAGGTGTCCGCCCCAC  660
 150  K  L  Y  C  Q  I  A  K  T  C  P  I  Q  I  K  V  S  A  P  P  169
 661 CGCCCCCGGGCACCGCCATCCGGGCCATGCCTGTCTACAAGAAGGCGGAGCACGTGACCG  720
 170  P  P  G  T  A  I  R  A  M  P  V  Y  K  K  A  E  H  V  T  D  189
 721 ACATCGTGAAGCGCTGCCCCAACCACGAGCTCGGGCGGGACTTCAACGAAGGACAGTCTG  780
 190  I  V  K  R  C  P  N  H  E  L  G  R  D  F  N  E  G  Q  S  A  209
 781 CCCCCAGCCAGCCACCTCATCCGTGTGGAAGGCAATAATCTCTCGCAGTATGTGGACGAC  840
 210  P  A  S  H  L  I  R  V  E  G  N  N  L  S  Q  Y  V  D  D  P  229
 841 CTGTCACCGGCAGGCAGAGCGTCGTGGTGCCCTATGAGCCACCACAGGTGGGGACAGAAT  900
 230  V  T  G  R  Q  S  V  V  V  P  Y  E  P  P  Q  V  G  T  E  F  249
 901 TCACCACCATCCTGTACAACTTCATGTGTAACAGCAGCTGTGTGGGGGGCATGAACCGAC  960
 250  T  T  I  L  Y  N  F  M  C  N  S  S  C  V  G  G  M  N  R  R  269
 961 GGCCCATCCTCATCATCATCACCCTGGAGACGCGGGATGGGCAGGTGCTGGGCCGCCGT 1020
 270  P  I  L  I  I  I  T  L  E  T  R  D  G  Q  V  L  G  R  R  S  289
1021 CCTTCGAGGGCCGCATCTGCGCCTGTCCTGGCCGGGACCGAAAAGCCGATGAGGACCACT 1080
 290  F  E  G  R  I  C  A  C  P  G  R  D  R  K  A  D  E  D  H  Y  309
1081 ACCGGGAGCAGCAGGCCTTGAATGAGAGCTCCGCCAAGAACGGGGCTGCCAGCAAGCGCG 1140
 310  R  E  Q  Q  A  L  N  E  S  S  A  K  N  G  A  A  S  K  R  A  329
1141 CCTTCAAGCAGAGTCCCCCTGCCGTCCCCGCCCTGGGCCCGGGTGTGAAGAAGCGGCGGC 1200
 330  F  K  Q  S  P  P  A  V  P  A  L  G  P  G  V  K  K  R  R  H  349
1201 ACGGAGACGAGGACACGTACTACCTGCAGGTGCGAGGCCGCGAGAACTTCGAGATCCTGA 1260
 350  G  D  E  D  T  Y  Y  L  Q  V  R  G  R  E  N  F  E  I  L  M  369
1261 TGAAGCTGAAGGAGAGCCTGGAGCTGATGGAGTTGGTGCCGCAGCCGCTGGTAGACTCCT 1320
 370  K  L  K  E  S  L  E  L  M  E  L  V  P  Q  P  L  V  D  S  Y  389
1321 ATCGGCAGCAGCAGCAGCTCCTACAGAGGCCGAGTCACCTACAGCCCCCATCCTACGGGC 1380
 390  R  Q  Q  Q  Q  L  L  Q  R  P  S  H  L  Q  P  P  S  Y  G  P  409
1381 CGGTCCTCTCGCCCATGAACAAGGTGCACGGGGGCGTGAACAAGCTGCCCTCCGTCAACC 1440
 410  V  L  S  P  M  N  K  V  H  G  G  V  N  K  L  P  S  V  N  Q  429
1441 AGCTGGTGGGCCAGCCTCCCCCGCACAGCTCGGCAGCTACACCCAACCTGGGACCTGTGG 1500
 430  L  V  G  Q  P  P  P  H  S  S  A  A  T  P  N  L  G  P  V  G  449
1501 GCTCTGGGATGCTCAACAACCACGGCCACGCAGTGCCAGCCAACAGCGAGATGACCAGCA 1560
 450  S  G  M  L  N  N  H  G  H  A  V  P  A  N  S  E  M  T  S  S  469
1561 GCCACGGCACCCAGTCCATGGTCTCGGGGTCCCACTGCACTCCGCCACCCCCCTACCACG 1620
 470  H  G  T  Q  S  M  V  S  G  S  H  C  T  P  P  P  P  Y  H  A  489
1621 CCGACCCCAGCCTCGTCAGTTTTTTTAACAGGATTGGGGTGTCCAAACTGCATCGAGTATT 1680
 490  D  P  S  L  V  S  F  L  T  G  L  G  C  P  N  C  I  E  Y  F  509
```

FIG. 4A

```
1681 TCACGTCCCAGGGGGTTACAGAGCATTTACCACCTGCAGAACCTGACCATCGAGGACCTGG 1740
 510   T  S  Q  G  L  Q  S  I  Y  H  L  Q  N  L  T  I  E  D  L  G  529
1741 GGGCCCTGAAGATCCCCGAGCAGTATCGCATGACCATCTGGCGGGGCCTGCAGGACCTGA 1800
 530   A  L  K  I  P  E  Q  Y  R  M  T  I  W  R  G  L  Q  D  L  K  549
1801 AGCAGGGCCACGACTACGGCGCCGCCGCGCAGCAGCTGCTCCGCTCCAGCAACGCGGCCG 1860
 550   Q  G  H  D  Y  G  A  A  A  Q  Q  L  L  R  S  S  N  A  A  A  569
1861 CCATTTCCATCGGCGGCTCCGGGGAGCTGCAGCGCCAGCGGGTCATGGAGGCCGTGCACT 1920
 570   I  S  I  G  G  S  G  E  L  Q  R  Q  R  V  M  E  A  V  H  F  589
1921 TCCGCGTGCGCCACACCATCACCATCCCCAACCGCGGCGGCCCCGGCGCCGGCCCCGACG 1980
 590   R  V  R  H  T  I  T  I  P  N  R  G  G  P  A  G  P  D  E  609
1981 AGTGGGCGGACTTCGGCTTCGACCTGCCCGACTGCAAGGCCCGCAAGCAGCCCATCAAGG 2040
 610   W  A  D  F  G  F  D  L  P  D  C  K  A  R  K  Q  P  I  K  E  629
2041 AGGAGTTCACGGAGGCCGAGATCCACTGAGGGGCCGGGCCCAGCCAGAGCCTGTGCCACC 2100
 630   E  F  T  E  A  E  I  H  *                                   649
2101 GCCCAGAGACCCAGGCCGCCTCGCTCTCCTTCCTGTGTCCAAAACTGCCTCCGGAGGCAG 2160
2161 GGCCTCCAGGCTGTGCCCGGGAAAGGCAAGGTCCGGCCCATGCCCCGGCACCTCACCGG 2220
2221 CCCCAGGAGAGGCCCAGCCACCAAAGCCGCCTGCGGACAGCCTGAGTCACCTGCAGAACC 2280
2281 TTCTGGAGCTGCCCTAATGCTGGGCTTGCGGGGCAGGGGCCGGCCCACTCTCAGCCCTGC 2340
2341 CACTGCCGGGCGTGCTCCATGGCAGGCGTGGGTGGGGACCGCAGTGTCAGCTCCGACCTC 2400
2401 CAGGCCTCATCCTAGAGACTCTGTCATCTGCCGATCAAGCAAGGTCCTTCCAGAGGAAAG 2460
2461 AATCCTCTTCGCTGGTGGACTGCCAAAAAGTATTTTGCGACATCTTTTGGTTCTGGAGAG 2520
2521 TGGTGAGCAGCCAAGCGACTGTGTCTGAAACACCGTGCATTTTCAGGGAATGTCCCTAAC 2580
2581 GGGCTGGGGACTCTCTCTGCTGGACTTGGGAGTGGCCTTTGCCCCCAGCACACTGTATTC 2640
2641 TGCGGGACCGCCTCCTTCCTGCCCCTAACAACCACCAAAGTGTTGCTGAAATTGGAGAAA 2700
2701 ACTGGGGAAGGCGCAACCCCTCCCAGGTGCGGGAAGCATCTGGTACCGCCTCGGCCAGTG 2760
2761 CCCCTCAGCCTGGCCACAGTCACCTCTCCTTGGGGAACCCTGGGCAGAAAGGGACAGCCT 2820
2821 GTCCTTAGAGGACCGGAAATTGTCAATATTTGATAAAATGATACCCTTTTCTAC     2874
```

FIG. 4B

```
  1 TGCCTCCCCGCCCGCGCACCCGCCCCGAGGCCTGTGCTCCTGCGAAGGGGACGCAGCGAA   60
 61 GCCGGGGCCCGCGCCAGGCCGGCCGGGACGGACGCCGATGCCCGGAGCTGCGACGGCTGC  120
121 AGAGCGAGCTGCCCTCGGAGGCCGGTGTGAGGAAGATGGCCCAGTCCACCACCTCCC     180
-10                                            M  A  Q  S  T  T  T  S  P    9
181 CCGATGGGGGCACCACGTTTGAGCACCTCTGGAGCTCTCTGGAACCAGACAGCACCTACT  240
 10  D  G  G  T  T  F  E  H  L  W  S  S  L  E  P  D  S  T  Y  F    29
241 TCGACCTTCCCCAGTCAAGCCGGGGGAATAATGAGGTGGTGGGTGGCACGGATTCCAGCA  300
 30  S  D  L  P  Q  S  S  R  G  N  N  E  V  V  G  G  T  D  S  S  H   49
301 TGGACGTCTTCCACCTAGAGGGCATGACCACATCTGTCATGGCCCAGTTCAATTTGCTGA  360
 50  D  V  F  H  L  E  G  M  T  T  S  V  M  A  Q  F  N  L  L  S    69
361 GCAGCACCATGGACCAGATGAGCAGCCGCGCTGCCTCGGCCAGCCCGTACACCCCGGAGC  420
 70  S  T  M  D  Q  M  S  S  R  A  A  S  A  S  P  Y  T  P  E  H    89
421 ACGCCGCCAGCGTGCCCACCCATTCACCCTACGCACAGCCCAGCTCCACCTTCGACACCA  480
 90  A  A  S  V  P  T  H  S  P  Y  A  Q  P  S  S  T  F  D  T  M   109
481 TGTCGCCCGCGCCTGTCATCCCCTCAACACCGACTATCCCGGACCCCACCACTTCGAGG   540
110  S  P  A  P  V  I  P  S  N  T  D  Y  P  G  P  H  H  F  E  V   129
541 TCACTTTCCAGCAGTCCAGCACGGCCAAGTCAGCCACCTGGACGTACTCCCCACTCTTGA  600
130  T  F  Q  Q  S  S  T  A  K  S  A  T  W  T  Y  S  P  L  L  K   149
601 AGAAACTCTACTGCCAGATCGCCAAGACATGCCCCATCCAGATCAAGGTGTCCGCCCCAC  660
150  K  L  Y  C  Q  I  A  K  T  C  P  I  Q  I  K  V  S  A  P  P   169
661 CGCCCCCGGGCACCGCCATCCGGGCCATGCCTGTCTACAAGAAGGCGGAGCACGTGACCG  720
170  P  P  G  T  A  I  R  A  M  P  V  Y  K  K  A  E  H  V  T  D   189
721 ACATCGTGAAGCGCTGCCCCAACCACGAGCTCGGGAGGGACTTCAACGAAGGACAGTCTG  780
190  I  V  K  R  C  P  N  H  E  L  G  R  D  F  N  E  G  Q  S  A   209
781 CCCCAGCCAGCCACCTCATCCGTGTGGAAGGCAATAATCTCTCGCAGTATGTGGACGACC  840
210  P  A  S  H  L  I  R  V  E  G  N  N  L  S  Q  Y  V  D  D  P   229
841 CTGTCACCGGCAGGCAGAGCGTCGTGGTGCCCTATGAGCCACCACAGGTGGGACAGAAT   900
230  V  T  G  R  Q  S  V  V  V  P  Y  E  P  P  Q  V  G  T  E  F   249
901 TCACCACCATCCTGTACAACTTCATGTGTAACAGCAGCTGTGTGGGGCATGAACCGAC   960
250  T  T  I  L  Y  N  F  M  C  N  S  S  C  V  G  G  M  N  R  R   269
961 GGCCCATCCTCATCATCATCACCCTGGAGACGCGGGATGGGCAGGTGCTGGGCCGCCGT  1020
270  P  I  L  I  I  I  T  L  E  T  R  D  G  Q  V  L  G  R  R  S   289
1021 CCTTCGAGGGCCGCATCTGCGCCTGTCCTGGCCGCGACCGAAAAGCCGATCAGGACCACT 1080
290  F  E  G  R  I  C  A  C  P  G  R  D  R  K  A  D  E  D  H  Y   309
1081 ACCGGGAGCAGCAGGCCTTGAATGAGAGCTCCGCCAAGAACGGGGCTGCCAGCAAGCGCG 1140
310  R  E  Q  Q  A  L  N  E  S  S  A  K  N  G  A  A  S  K  R  A   329
1141 CCTTCAAGCAGAGTCCCCCCTGCCGTCCCCGCCTGGGGCCGGGTGTGAAGAAGCGGCGC  1200
330  F  K  Q  S  P  P  A  V  P  A  L  G  P  G  V  K  K  R  R  H   349
1201 ACGGAGACGAGGACACGTACTACCTGCAGGTGCGAGGCCGCGAGAACTTCGAGATCCTGA 1260
350  G  D  E  D  T  Y  Y  L  Q  V  R  G  R  E  H  F  E  I  L  M   369
1261 TGAAGCTGAAGGAGAGCCTGGAGCTGATGGAGTTGGTGCCGCAGCCGCTGGTAGACTCCT 1320
370  K  L  K  E  S  L  E  L  M  E  L  V  P  Q  P  L  V  D  S  Y   389
1321 ATCGGCAGCAGCAGCAGCTCCTACAGAGGCCGAGTCACCTACAGCCCCCATCCTACGGGC 1380
390  R  Q  Q  Q  Q  L  L  Q  R  P  S  H  L  Q  P  P  S  Y  G  P   409
1381 CGGTCCTCTCGCCCATGAACAAGGTGCACGGGGGCGTGAACAAGCTGCCCTCCGTCAACC 1440
410  V  L  S  P  M  N  K  V  H  G  G  V  N  K  L  P  S  V  N  Q   429
1441 AGCTGGTGGGCCAGCCTCCCCCGCACAGCTCGGCAGCTACACCCAACCTGGGACCTGTGG 1500
430  L  V  G  Q  P  P  P  H  S  S  A  A  T  P  H  L  G  P  V  G   449
1501 GCTCTGGGATGCTCAACAACCACGGCCACGCAGTGCCAGCCAACAGCGAGATGACCAGCA 1560
450  S  G  M  L  N  N  H  G  H  A  V  P  A  N  S  E  M  T  S  S   469
1561 GCCACGGCACCCAGTCCATGGTCTCGGGGTCCCACTGCACTCCGCCACCCCCTACCACG  1620
470  H  G  T  Q  S  M  V  S  G  S  H  C  T  P  P  P  Y  H  A   489
1621 CCGACCCCAGCCTCGTCAGGACCTGGGGGCCCTGAAGATCCCCGAGCAGTATCGCATGAC 1680
490  D  P  S  L  V  R  T  W  G  P  *                              509
1681 CATCTGGCGGGGCCTGCAGGACCTGAAGCAGGGCCCACGACTACGGCGCCGCGCGCAGCA 1740
1741 GCTGCTCCGCTCCAGCAACGCGGCCGCCATTTCCATCGGCGGCTCCGGGAGCTGCAGCG  1800
1801 CCAGCGGGTCATGGAGGCCGTGCACTTCCGCGTGCGCCACACCATCACCATCCCCAACCG 1860
1861 CGGCGGCCCCGGCGCCGGCCCCGACGAGTGGCGGACTTCGGCTTCGACCTGCCCGACTG  1920
1921 CAAGGCCCGCAAGCAGCCCATCAAGGAGGAGTTCACGGAGGCCGAGATCCACTGAGGGGC 1980
1981 CGGGCCCAGCCAGAGCCTGTGCCACCGCCCAGAGACCCAGGCCGCCTCGCTCTC     2034
```

FIG.5

```
   1  GCGAGCTGCCCTCGGAGGCCGGCGTGGGGAAGATGGCCCAGTCCACCGCCACCTCCCCTG    60
  -9                                   M  A  Q  S  T  A  T  S  P  D   10
  61  ATGGGGGCACCACGTTTGAGCACCTCTGGAGCTCTCTGGAACCAGACAGCACCTACTTCG   120
  11   G  G  T  T  F  E  H  L  W  S  S  L  E  P  D  S  T  Y  F  D    30
 121  ACCTTCCCCAGTCAAGCCGGGGGAATAATGAGGTGGTGGGCGGAACGGATTCCAGCATGG   180
  31   L  P  Q  S  S  R  G  N  N  E  V  V  G  G  T  D  S  S  M  D    50
 181  ACGTCTTCCACCTGGAGGGCATGACTACATCTGTCATGGCCCAGTTCAATCTGCTGAGCA   240
  51   V  F  H  L  E  G  M  T  T  S  V  M  A  Q  F  N  L  L  S  S    70
 241  GCACCATGGACCAGATGAGCAGCCGCGCGGCCTCGGCCAGCCCCTACACCCCAGAGCACG   300
  71   T  M  D  Q  M  S  S  R  A  A  S  A  S  P  Y  T  P  E  H  A    90
 301  CCGCCAGCGTGCCCACCCACTCGCCCTACGCACAACCCAGCTCCACCTTCGACACCATGT   360
  91   A  S  V  P  T  H  S  P  Y  A  Q  P  S  S  T  F  D  T  M  S   110
 361  CGCCGGCGCCTGTCATCCCCTCCAACACCGACTACCCCGGACCCCACCACTTTGAGGTCA   420
 111   P  A  P  V  I  P  S  N  T  D  Y  P  G  P  H  H  F  E  V  T   130
 421  CTTTCCAGCAGTCCAGCACGGCCAAGTCAGCCACCTGGACGTACTCCCCGCTCTTGAAGA   480
 131   F  Q  Q  S  S  T  A  K  S  A  T  W  T  Y  S  P  L  L  K  K   150
 481  AACTCTACTGCCAGATCGCCAAGACATGCCCCATCCAGATCAAGGTGTCCACCCCGCCAC   540
 151   L  Y  C  Q  I  A  K  T  C  P  I  Q  I  K  V  S  T  P  P  P   170
 541  CCCCAGGCACTGCCATCCGGGCCATGCCTGTTTACAAGAAAGCGGAGCACGTGACCGACG   600
 171   P  G  T  A  I  R  A  M  P  V  Y  K  K  A  E  H  V  T  D  V   190
 601  TCGTGAAACGCTGCCCCAACCACGAGCTCGGGAGGGACTTCAACGAAGGACAGTCTGCTC   660
 191   V  K  R  C  P  N  H  E  L  G  R  D  F  N  E  G  Q  S  A  P   210
 661  CAGCCAGCCACCTCATCCGCGTGGAAGGCAATAATCTCTCGCAGTATGTGGATGACCCTG   720
 211   A  S  H  L  I  R  V  E  G  N  N  L  S  Q  Y  V  D  D  P  V   230
 721  TCACCGGCAGGCAGAGCGTCGTGGTGCCCTATGAGCCACCACAGGTGGGGACGGAATTCA   780
 231   T  G  R  Q  S  V  V  V  P  Y  E  P  P  Q  V  G  T  E  F  T   250
 781  CCACCATCCTGTACAACTTCATGTGTAACAGCAGCTGTGTAGGGGGCATGAACCGGCGGC   840
 251   T  I  L  Y  N  F  M  C  N  S  S  C  V  G  G  M  N  R  R  P   270
 841  CCATCCTCATCATCATCACCCTGGAGATGCGGGATGGGCAGGTGCTGGGCCGCCGGTCCT   900
 271   I  L  I  I  I  T  L  E  M  R  D  G  Q  V  L  G  R  R  S  F   290
 901  TTGAGGGCCGCATCTGCGCCTGTCCTGGCCGCGACCGAAAAGCTGATGAGGACCACTACC   960
 291   E  G  R  I  C  A  C  P  G  R  D  R  K  A  D  E  D  H  Y  R   310
 961  GGGAGCAGCAGGCCCTGAACGAGAGCTCCGCCAAGAACGGGGCCGCCAGCAAGCGTGCCT  1020
 311   E  Q  Q  A  L  N  E  S  S  A  K  N  G  A  A  S  K  R  A  F   330
1021  TCAAGCAGAGCCCCCCTGCCGTCCCCGCCCTTGGTGCCGGTGTGAAGAAGCGGCGGCATG  1080
 331   K  Q  S  P  P  A  V  P  A  L  G  A  G  V  K  K  R  R  H  G   350
1081  GAGACGAGGACACGTACTACCTTCAGGTGCGAGGCCGGGAGAACTTTGAGATCCTGATGA  1140
 351   D  E  D  T  Y  Y  L  Q  V  R  G  R  E  N  F  E  I  L  M  K   370
1141  AGCTGAAAGAGAGCCTGGAGCTGATGGAGTTGGTGCCGCAGCCACTGGTGGACTCCTATC  1200
 371   L  K  E  S  L  E  L  M  E  L  V  P  Q  P  L  V  D  S  Y  R   390
1201  GGCAGCAGCAGCAGCTCCTACAGAGGCCGAGTCACCTACAGCCCCCGTCCTACGGGCCGG  1260
 391   Q  Q  Q  Q  L  L  Q  R  P  S  H  L  Q  P  P  S  Y  G  P  V   410
1261  TCCTCTCGCCCATGAACAAGGTGCACGGGGGCATGAACAAGCTGCCCTCCGTCAACCAGC  1320
 411   L  S  P  M  N  K  V  H  G  G  M  N  K  L  P  S  V  N  Q  L   430
1321  TGGTGGGCCAGCCTCCCCCGCACAGTTCGGCAGCTACACCCAACCTGGGGCCCGTGGGCC  1380
 431   V  G  Q  P  P  P  H  S  S  A  A  T  P  N  L  G  P  V  G  P   450
1381  CCGGGATGCTCAACAACCATGGCCACGCAGTGCCAGCCAACGGCGAGATGAGCAGCAGCC  1440
 451   G  M  L  N  N  H  G  H  A  V  P  A  N  G  E  M  S  S  S  H   470
```

FIG. 6A

```
1441 ACAGCGCCCAGTCCATGGTCTCGGGGTCCCACTGCACTCCGCCACCCCCTACCACGCCG 1500
 471    S  A  Q  S  M  V  S  G  S  H  C  T  P  P  P  Y  H  A  D   490
1501 ACCCCAGCCTCGTCAGTTTTTTAACAGGATTGGGGTGTCCAAACTGCATCGAGTATTTCA 1560
 491    P  S  L  V  S  F  L  T  G  L  G  C  P  N  C  I  E  Y  F  T  510
1561 CCTCCCAAGGGTTACAGAGCATTTACCACCTGCAGAACCTGACCATTGAGGACCTGGGG  1620
 511    S  Q  G  L  Q  S  I  Y  H  L  Q  N  L  T  I  E  D  L  G  A  530
1621 CCCTGAAGATCCCCGAGCAGTACCGCATGACCATCTGGCGGGGCCTGCAGGACCTGAAGC 1680
 531    L  K  I  P  E  Q  Y  R  M  T  I  W  R  G  L  Q  D  L  K  Q  550
1681 AGGGCCACGACTACAGCACCGCGCAGCAGCTGCTCCGCTCTAGCAACGCGGCCACCATCT 1740
 551    G  H  D  Y  S  T  A  Q  Q  L  L  R  S  S  N  A  A  T  I  S  570
1741 CCATCGGCGGCTCAGGGGAACTGCAGCGCCAGCGGGTCATGGAGGCCGTGCACTTCCGCG 1800
 571    I  G  G  S  G  E  L  Q  R  Q  R  V  M  E  A  V  H  F  R  V  590
1801 TGCGCCACACCATCACCATCCCCAACCGCGGCGGCCCAGGCGGCGGCCCTGACGAGTGGG 1860
 591    R  H  T  I  T  I  P  N  R  G  G  P  G  G  G  P  D  E  W  A  610
1861 CGGACTTCGGCTTCGACCTGCCCGACTGCAAGGCCCGCAAGCAGCCCATCAAGGAGGAGT 1920
 611    D  F  G  F  D  L  P  D  C  K  A  R  K  Q  P  I  K  E  E  F  630
1921 TCACGGAGGCCGAGATCCACTGAGGGCCTCGCCTGGCTGCAGCCTGCGCCACCGCCCAGA 1980
 631    T  E  A  E  I  H  *                                        650
1981 GACCCAAGCTGCCTCCCCTCTCCTTCCTGTGTGTCCAAAACTGCCTCAGGAGGCAGGACC 2040
2041 TTCGGGCTGTGCCCGGGGAAAGGCAAGGTCCGGCCCATCCCCAGGCACCTCACAGGCCCC 2100
2101 AGGAAAGGCCCAGCCACCGAAGCCGCCTGTGGACAGCCTGAGTCACCTGCAGAACC      2156
```

FIG. 6B

```
   1 TGATCTCCCTGTGGCCTGCAGGGGACTGAGCCAGGGAGTAGATGCCCTGAGACCCCAAGG   60
  61 GACACCCAAGGAAACCTTGCTGGCTTTGAGAAAGGGATCGTCTCTCTCCTGCCCAAGAGA  120
 121 AGCATGTGTATGGGCCCTGTGTATGAATCCTTGGGGCAGGCCCAGTTCAATTTGCTCAGC  180
   0           M  C  M  G  P  V  Y  E  S  L  G  Q  A  Q  F  N  L  L  S   19
 181 AGTGCCATGGACCAGATGGGCAGCCGTGCGGCCCCGGCGAGCCCCTACACCCCGGAGCAC  240
  20  S  A  M  D  Q  M  G  S  R  A  A  P  A  S  P  Y  T  P  E  H    39
 241 GCCGCCAGCGCGCCCACCCACTCGCCCTACGCGCAGCCCAGCTCCACCTTCGACACCATG  300
  40  A  A  S  A  P  T  H  S  P  Y  A  Q  P  S  S  T  F  D  T  M    59
 301 TCTCCGGCGCCTGTCATCCCTTCCAATACCGACTACCCCGGCCCCCACCACTTCGAGGTC  360
  60  S  P  A  P  V  I  P  S  N  T  D  Y  P  G  P  H  H  F  E  V    79
 361 ACCTTCCAGCAGTCGAGCACTGCCAAGTCGGCCACCTGGACATACTCCCCACTCTTGAAG  420
  80  T  F  Q  Q  S  S  T  A  K  S  A  T  W  T  Y  S  P  L  L  K    99
 421 AAGTTGTACTGTCAGATTGCTAAGACATGCCCCATCCAGATCAAAGTGTCCACACCACCA  480
 100  K  L  Y  C  Q  I  A  K  T  C  P  I  Q  I  K  V  S  T  P  P   119
 481 CCCCCGGGCACGGCCATCCGGGCCATGCCTGTCTACAAGAAGGCAGAGCATGTGACCGAC  540
 120  P  P  G  T  A  I  R  A  M  P  V  Y  K  K  A  E  H  V  T  D   139
 541 ATTGTTAAGCGCTGCCCCAACCACGAGCTGGAAGGGACTTCAATGAAGGACAGTCTGCC   600
 140  I  V  K  R  C  P  N  H  E  L  G  R  D  F  N  E  G  Q  S  A   159
 601 CCGGCTAGCCACCTCATCCGTGTAGAAGGCAACAACCTCGCCCAGTACGTGGATGACCCT  660
 160  P  A  S  H  L  I  R  V  E  G  N  N  L  A  Q  Y  V  D  D  P   179
 661 GTCACCGGAAGGCAGAGTGTGGTTGTGCCGTATGAACCCCCACAGGTGGGAACAGAATTT  720
 180  V  T  G  R  Q  S  V  V  V  P  Y  E  P  P  Q  V  G  T  E  F   199
 721 ACCACCATCCTGTACAACTTCATGTGTAACAGCAGCTGTGTGGGGGGCATGAATCGGAGG  780
 200  T  T  I  L  Y  N  F  M  C  N  S  S  C  V  G  G  M  N  R  R   219
 781 CCCATCCTTGTCATCATCACCCTGGAGACCCGGGATGGACAGGTCCTGGGCCGCCGGTCT  840
 220  P  I  L  V  I  I  T  L  E  T  R  D  G  Q  V  L  G  R  R  S   239
 841 TTCGAGGGTCGCATCTGTGCCTGTCCTGGCCGTGACCGCAAAGCTGATGAAGACCATTAC  900
 240  F  E  G  R  I  C  A  C  P  G  R  D  R  K  A  D  E  D  H  Y   259
 901 CGGGAGCAACAGGCTCTGAATGAAAGTACCACCAAAAATGGAGCTGCCAGCAAACGTGCA  960
 260  R  E  Q  Q  A  L  N  E  S  T  T  K  N  G  A  A  S  K  R  A   279
 961 TTCAAGCAGAGCCCCCTGCCATCCCTGCCCTGGGTACCAACGTGAAGAAGAGACGCCAC  1020
 280  F  K  Q  S  P  P  A  I  P  A  L  G  T  N  V  K  K  R  R  H   299
1021 GGGGACGAGGACATGTTCTACATGCACGTGCGAGGCCGGGAGAACTTTGAGATCTTGATG  1080
 300  G  D  E  D  M  F  Y  M  H  V  R  G  R  E  N  F  E  I  L  M   319
1081 AAAGTCAAGGAGAGCCTAGAACTGATGGAGCTTGTGCCCCAGCCTTTGGTTGACTCCTAT  1140
 320  K  V  K  E  S  L  E  L  M  E  L  V  P  Q  P  L  V  D  S  Y   339
1141 CGACAGCAGCAGCAGCAGCAGCTCCTACAGAGGCCGAGTCACCTGCAGCCTCCATCCTAT  1200
 340  R  Q  Q  Q  Q  Q  Q  L  L  Q  R  P  S  H  L  Q  P  P  S  Y   359
1201 GGGCCCGTGCTCTCCCCAATGAACAAGGTACACGGTGGTGTCAACAAACTGCCCTCCGTC  1260
 360  G  P  V  L  S  P  M  N  K  V  H  G  G  V  N  K  L  P  S  V   379
1261 AACCAGCTGGTGGGCCAGCCTCCCCCGCACAGCTCAGCAGCTGGGCCCAACCTGGGGCCC  1320
 380  N  Q  L  V  G  Q  P  P  P  H  S  S  A  A  G  P  N  L  G  P   399
1321 ATGGGCTCCGGGATGCTCAACAGCCACGGCCACAGCATGCCGGCCAATGGTGAGATGAAT  1380
 400  M  G  S  G  M  L  N  S  H  G  H  S  M  P  A  N  G  E  M  N   419
1381 GGAGGCCACAGCTCCCAGACCATGGTTTCGGGATCCCACTGCACCCCGCCACCCCCCTAT  1440
 420  G  G  H  S  S  Q  T  M  V  S  G  S  H  C  T  P  P  P  P  Y   439
1441 CATGCAGACCCCAGCCTCGTCAGTTTTTTGACAGGGTTGGGGTGTCCAAACTGCATCGAG  1500
 440  H  A  D  P  S  L  V  S  F  L  T  G  L  G  C  P  N  C  I  E   459
1501 TGCTTCACTTCCCAAGGGTTGCAGAGCATCTACCACCTGCAGAACCTTACCATCGAGGAC  1560
 460  C  F  T  S  Q  G  L  Q  S  I  Y  H  L  Q  N  L  T  I  E  D   479
1561 CTTGGGGCTCTGAAGGTCCCTGACCAGTACCGTATGACCATCTGGAGGGGCCTACAGGAC  1620
 480  L  G  A  L  K  V  P  D  Q  Y  R  M  T  I  W  R  G  L  Q  D   499
1621 CTGAAGCAGAGCCATGACTGCGGCCAGCAACTGCTACGCTCCAGCAGCAACGCGGCCACC  1680
 500  L  K  Q  S  H  D  C  G  Q  Q  L  L  R  S  S  S  N  A  A  T   519
1681 ATCTCCATCGGCGGCTCTGGCGAGCTGCAGCGGCAGCGGGTCATGGAAGCCGTGCATTTC  1740
 520  I  S  I  G  G  S  G  E  L  Q  R  Q  R  V  M  E  A  V  H  F   539
1741 CGTGTGCGCCACACCATCACAATCCCCAACCGTGGAGGCGCAGGTGCGGTGACAGGTCCC  1800
 540  R  V  R  H  T  I  T  I  P  N  R  G  G  A  G  A  V  T  G  P   559
1801 GACGAGTGGGCGGACTTTGGCTTTGACCTGCCTGACTGCAAGTCCCGTATGCAGCCCATC  1860
 560  D  E  W  A  D  F  G  F  D  L  P  D  C  K  S  R  K  Q  P  I   579
1861 AAAGAGGAGTTCACAGAGACAGAGAGCCACTGAGGAACGTACCTTCTTCTCCTGTCCTTC  1920
 580  K  E  E  F  T  E  T  E  S  H  *                              599
1921 CTCTGTGAGAAACTGCTCTTGGAAGTGGGACCTGTTGGCTGTGCCCACAGAAACCAGCAA  1980
1981 GGACCTTCTGCCGGATGCCATTCCTGAAGGGAAGTCGCTCATGAACTAACTCCCTCTTGG  2040
```

FIG.7

```
  1 TGGTCCCGCTTCGACCAAGACTCCGGCTACCAGCTTGCGGGCCCCGCGGAGGAGGAGACC   60
 61 CCGCTGGGGCTAGCTGGGCGACGCGCGCCAAGCGGCGGCGGGAAGGAGGCGGGAGGAGCG  120
121 GGGCCCGAGACCCCGACTCGGGCAGAGCCAGCTGGGGAGGCGGGGCGCGCGTGGGAGCCA  180
181 GGGGCCCGGGTGGCCGGCCCTCCTCCGCCACGGCTGAGTGCCCGCGCTGCCTTCCCGCCG  240
241 GTCCGCCAAGAAAGGCGCTAAGCCTGCGGCAGTCCCCTCGCCGCCGCCTCCCTGCTCCGC  300
301 ACCCTTATAACCCGCCGTCCCGCATCCAGGCGAGGAGGCAACGCTGCAGCCCAGCCCTCG  360
361 CCGACGCCGACGCCCGGCCCGGAGCAGAATGAGCGGCAGCGTTGGGGAGATGGCCCAGAC  420
 -8                                  M  S  G  S  V  G  E  M  A  Q  T   11
421 CTCTTCTTCCTCCTCCTCCACCTTCGAGCACCTGTGGAGTTCTCTAGAGCCAGACAGCAC  480
 12  S  S  S  S  S  S  T  F  E  H  L  W  S  S  L  E  P  D  S  T   31
481 CTACTTTGACCTCCCCCAGCCCAGCCAAGGGACTAGCGAGGCATCAGGCAGCGAGGAGTC  540
 32  Y  F  D  L  P  Q  P  S  Q  G  T  S  E  A  S  G  S  E  E  S   51
541 CAACATGGATGTCTTCCACCTGCAAGGCATGGCCCAGTTCAATTTGCTCAGCAGTGCCAT  600
 52  N  M  D  V  F  H  L  Q  G  M  A  Q  F  N  L  L  S  S  A  M   71
601 GGACCAGATGGGCAGCCGTGCGGCCCCGGCGAGCCCCTACACCCCGGAGCACGCCGCCAG  660
 72  D  Q  M  G  S  R  A  A  P  A  S  P  Y  T  P  E  H  A  A  S   91
661 CGCGCCCACCCACTCGCCCTACGCGCAGCCCAGCTCCACCTTCGACACCATGTCTCCGGC  720
 92  A  P  T  H  S  P  Y  A  Q  P  S  S  T  F  D  T  M  S  P  A  111
721 GCCTGTCATCCCTTCCAATACCGACTACCCCGGCCCCC  758
112  P  V  I  P  S  N  T  D  Y  P  G  P  123
```

FIG. 8

```
_ Name: sr-p70a-cos3    Len:   650  Check: 9661  Weight:  1.00
_ Name: sr-p70b-cos3    Len:   650  Check: 3605  Weight:  1.00
_ Name: sr-p70-ht29     Len:   650  Check:   85  Weight:  1.00
_ Name: sr-p70c-att20   Len:   650  Check: 4072  Weight:  1.00
_ Name: sr-p70a-att20   Len:   650  Check: 4204  Weight:  1.00
_//
```

|               |    1              |            |            |            |       50  |
|---------------|-------------------|------------|------------|------------|-----------|
| sr-p70a-cos3  | .......MAQ        | STTTSPDGGT | TFEHLWSSLE | PDSTYFDLPQ | SSRGNNEVVG |
| sr-p70b-cos3  | .......MAQ        | STTTSPDGGT | TFEHLWSSLE | PDSTYFDLPQ | SSRGNNEVVG |
| sr-p70-ht29   | .......MAQ        | STATSPDGGT | TFEHLWSSLE | PDSTYFDLPQ | SSRGNNEVVG |
| sr-p70c-att20 | ..........        | .......... | .......... | .......... | .......... |
| sr-p70a-att20 | MSGSVGEMAQ        | ...TSSSSSS | TFEHLWSSLE | PDSTYFDLPQ | PSQGTSEASG |

|               |    51             |            |            |            |      100  |
|---------------|-------------------|------------|------------|------------|-----------|
| sr-p70a-cos3  | GTDSSMD.VF        | HLEGMTTSVH | AQFNLLSSTM | DQMSSRAASA | SPYTPEHAAS |
| sr-p70b-cos3  | GTDSSMD.VF        | HLEGMTTSVH | AQFNLLSSTM | DQMSSRAASA | SPYTPEHAAS |
| sr-p70-ht29   | GTDSSMD.VF        | HLEGMTTSVH | AQFNLLSSTM | DQMSSRAASA | SPYTPEHAAS |
| sr-p70c-att20 | ...MCMGPVY        | ..ESLG...Q | AQFNLLSSAM | DQMGSRAAPA | SPYTPEHAAS |
| sr-p70a-att20 | SEESNMD.VF        | HLQGM..... | AQFNLLSSAM | DQMGSRAAPA | SPYTPEHAAS |

|               |    101            |            |            |            |      150  |
|---------------|-------------------|------------|------------|------------|-----------|
| sr-p70a-cos3  | VPTHSPYAQP        | SSTFDTMSPA | PVIPSNTDYP | GPHHFEVTFQ | QSSTAKSATW |
| sr-p70b-cos3  | VPTHSPYAQP        | SSTFDTMSPA | PVIPSNTDYP | GPHHFEVTFQ | QSSTAKSATW |
| sr-p70-ht29   | VPTHSPYAQP        | SSTFDTMSPA | PVIPSNTDYP | GPHHFEVTFQ | QSSTAKSATW |
| sr-p70c-att20 | APTHSPYAQP        | SSTFDTMSPA | PVIPSNTDYP | GP........ | .......... |
| sr-p70a-att20 | APTHSPYAQP        | SSTFDTMSPA | PVIPSNTDYP | GP........ | .......... |

|               |    151            |            |            |            |      200  |
|---------------|-------------------|------------|------------|------------|-----------|
| sr-p70a-cos3  | TYSPLLKKLY        | CQIAKTCPIQ | IKVSAPPPPG | TAIRAHPVYK | KAEHVTDIVK |
| sr-p70b-cos3  | TYSPLLKKLY        | CQIAKTCPIQ | IKVSAPPPPG | TAIRAHPVYK | KAEHVTDIVK |
| sr-p70-ht29   | TYSPLLKKLY        | CQIAKTCPIQ | IKVSTPPPPG | TAIRAHPVYK | KAEHVTDVVK |
| sr-p70c-att20 | TYSPLLKKLY        | CQIAKTCPIQ | IKVSTPPPPG | TAIRAHPVYK | KAEHVTDIVK |
| sr-p70a-att20 | ..........        | .......... | .......... | .......... | .......... |

|               |    201            |            |            |            |      250  |
|---------------|-------------------|------------|------------|------------|-----------|
| sr-p70a-cos3  | RCPNHELGRD        | FNEGQSAPAS | HLIRVEGNNL | SQYVDDPVTG | RQSVVVPYEP |
| sr-p70b-cos3  | RCPNHELGRD        | FNEGQSAPAS | HLIRVEGNNL | SQYVDDPVTG | RQSVVVPYEP |
| sr-p70-ht29   | RCPNHELGRD        | FNEGQSAPAS | HLIRVEGNNL | SQYVDDPVTG | RQSVVVPYEP |
| sr-p70c-att20 | RCPNHELGRD        | FNEGQSAPAS | HLIRVEGNNL | AQYVDDPVTG | RQSVVVPYEP |
| sr-p70a-att20 | ..........        | .......... | .......... | .......... | .......... |

|               |    251            |            |            |            |      300  |
|---------------|-------------------|------------|------------|------------|-----------|
| sr-p70a-cos3  | PQVGTEFTTI        | LYNFMCNSSC | VGGMNRRPIL | IIITLETRDG | QVLGRRSFEG |
| sr-p70b-cos3  | PQVGTEFTTI        | LYNFMCNSSC | VGGMNRRPIL | IIITLETRDG | QVLGRRSFEG |
| sr-p70-ht29   | PQVGTEFTTI        | LYNFMCNSSC | VGGMNRRPIL | IIITLEMRDG | QVLGRRSFEG |
| sr-p70c-att20 | PQVGTEFTTI        | LYNFMCNSSC | VGGMNRRPIL | VIITLETRDG | QVLGRRSFEG |
| sr-p70a-att20 | ..........        | .......... | .......... | .......... | .......... |

|               |    301            |            |            |            |      350  |
|---------------|-------------------|------------|------------|------------|-----------|
| sr-p70a-cos3  | RICACPGRDR        | KADEDHYREQ | QALNESSAKN | GAASKRAFKQ | SPPAVPALGP |
| sr-p70b-cos3  | RICACPGRDR        | KADEDHYREQ | QALNESSAKN | GAASKRAFKQ | SPPAVPALGP |
| sr-p70-ht29   | RICACPGRDR        | KADEDHYREQ | QALNESSAKN | GAASKRAFKQ | SPPAVPALGA |
| sr-p70c-att20 | RICACPGRDR        | KADEDHYREQ | QALNESTTKN | GAASKRAFKQ | SPPAIPALGT |
| sr-p70a-att20 | ..........        | .......... | .......... | .......... | .......... |

FIG. 9A

```
                   351                                                          400
_ sr-p70a-cos3     GVKKRRHGDE DTYYLQVRGR ENFEILMKLK ESLELMELVP QPLVDSYR..
_ sr-p70b-cos3     GVKKRRHGDE DTYYLQVRGR ENFEILMKLK ESLELMELVP QPLVDSYR..
_ sr-p70-ht29      GVKKRRHGDE DTYYLQVRGR ENFEILMKLK ESLELMELVP QPLVDSYR..
_sr-p70c-att20     NVKKRRHGDE DMFYMHVRGR ENFEILMKVK ESLELMELVP QPLVDSYRQQ
_sr-p70a-att20     .......... .......... .......... .......... ..........

401                                                          450
_ sr-p70a-cos3     QQQQLLQRPS HLQPPSYGPV LSPMNKVHGG VNKLPSVNQL VGQPPPHSSA
_ sr-p70b-cos3     QQQQLLQRPS HLQPPSYGPV LSPMNKVHGG VNKLPSVNQL VGQPPPHSSA
_ sr-p70-ht29      QQQQLLQRPS HLQPPSYGPV LSPMNKVHGG MNKLPSVNQL VGQPPPHSSA
_sr-p70c-att20     QQQQLLQRPS HLQPPSYGPV LSPMNKVHGG VNKLPSVNQL VGQPPPHSSA
_sr-p70a-att20     .......... .......... .......... .......... ..........

451                                                          500
_ sr-p70a-cos3     ATPNLGPVGS GMLNNHGHAV PANSEMTSSH GTQSMVSGSH CTPPPPYHAD
_ sr-p70b-cos3     ATPNLGPVGS GMLNNHGHAV PANSEMTSSH GTQSMVSGSH CTPPPPYHAD
_ sr-p70-ht29      ATPNLGPVGP GMLNNHGHAV PANGEMSSSH SAQSMVSGSH CTPPPPYHAD
_sr-p70c-att20     AGPNLGPMGS GMLNSHGHSM PANGEMNGGH SSQTMVSGSH CTPPPPYHAD
_sr-p70a-att20     .......... .......... .......... .......... ..........

501                                                          550
_ sr-p70a-cos3     PSLVSFLTGL GCPNCIEYFT SQGLQSIYHL QNLTIEDLGA LKIPEQYRMT
_ sr-p70b-cos3     PSLVR..T.W G.P....... .......... .......... ..........
_ sr-p70-ht29      PSLVSFLTGL GCPNCIEYFT SQGLQSIYHL QNLTIEDLGA LKIPEQYRMT
_sr-p70c-att20     PSLVSFLTGL GCPNCIECFT SQGLQSIYHL QNLTIEDLGA LKVPDQYRMT
_sr-p70a-att20     .......... .......... .......... .......... ..........

551                                                          600
_ sr-p70a-cos3     IWRGLQDLKQ GHDYGAAAQQ LLR.SSNAAA ISIGGSGELQ RQRVMEAVHF
_ sr-p70b-cos3     .......... .......... .......... .......... ..........
_ sr-p70-ht29      IWRGLQDLKQ GHDYS.TAQQ LLR.SSNAAT ISIGGSGELQ RQRVMEAVHF
_sr-p70c-att20     IWRGLQDLKQ SHDCG...QQ LLRSSSNAAT ISIGGSGELQ RQRVMEAVHF
_sr-p70a-att20     .......... .......... .......... .......... ..........

601                                                          650
_ sr-p70a-cos3     RVRHTITIPN RGGPGA..GP DEWADFGFDL PDCKARKQPI KEEFTEAEIH
_ sr-p70b-cos3     .......... .......... .......... .......... ..........
_ sr-p70-ht29      RVRHTITIPN RGGPGG...GP DEWADFGFDL PDCKARKQPI KEEFTEAEIH
_sr-p70c-att20     RVRHTITIPN RGGAGAVTGP DEWADFGFDL PDCKSRKQPI KEEFTETESH
_sr-p70a-att20     .......... .......... .......... .......... ..........
```

FIG. 9B

```
1↔2                        ↔3
  1 MAQS..TATSPDGGTTFEHLWSSLEPDSTYFDLPQSSRGNNEVVGGTDSSMD  50
    ||     |      ||  ||   |              ||         ||
  1 MEEPQSDPSVEPPLSQETFSDLWKLLPE............NNVLSPLPSQAMD 41
1↔2                    ↔3                    ↔4
                     ↔4
 51 VFHLEGMTTSVMAQFNLLSSTMDQMSSRAASASPYTPEHAASVPTHSPYA 100
        |         |                |    |  |   |
 42 DLML...SPDDIEQWFTEDPGPDEAPRMPEAAPPVAPAPAAPTPA.APAP  87
                                                 ↔5
101 QPSSTFDTMSPAPVIPSNTDYPGPHHFEVTFQQSSTAKSATWIYSPLLKK 150
    ||              ||  |     |    |||||  |||||  |
 88 APSWPL.....SSSVPSQKTYQGSYGFRLGFLHSGTAKSVTCTYSPALNK 132
                                                ↔5
151 LYCQIAKTCPIQIKVSTPPPPGTAIRAMPVYKKAEHVTDVVKRCPNHELG 200
    ||  ||||| |    |||||  |||| ||   ||   |  | ||  ||
133 MFCQLAKTCPVQLWVDSTPPPGTRVRAMAIYKQSQHMTEVVRRCPHHE.. 180
       ↔6                              ↔7
201 RDFNEGQSAPASHLIRVEGNNLSQYVDDPVTGRQSVVVPYEPPQVGTEFT 250
     |     ||  ||||||||  |  ||   | |||||||||||  |   |
181 RCSDSDGLAPPQHLIRVEGNLRVEYLDDRNTFRHSVVVPYEPPEVGSDCT 230
        ↔6                ↔8            ↔7
251 TILYNFMCNSSCVGGMNRRPILIIITLEMRDGQVLGRRSFEGRICACPGR 300
    || || ||||| |||||||||| |||| || ||||| |||| ||||||
231 TIHYNYMCNSSCMGGMNRRPILTIITLEDSSGNLLGRNSFEVRVCACPGR 280
                                 ↔9
                               ↔8
301 DRKADEDHYREQQALNESSAKNGAASKRAFKQSPPAVPALGAGVKKRRHG 350
    ||    |    |             |||     |
281 DRRTEEENLRKKGEPHHELP..PGSTKRALPNNTSSSPQ.....PKKKPL 323
        ↔10                ↔9                 ↔11
351 DEDTYYLQVRGRENFEILMKLKESLELMELVPQPLVDSYRQQQQLLQRPS 400
    |   ||||||||| || | |||   |           |     |
324 DGEYFTLQIRGRERFEMFRELNEALELKDAQAGKEPGGSRAHSSHLKSKK 373
        ↔10                            ↔11 ↔12
401 HLQPPSYGPVLSPMNKVHGGMNKLPSVNQLVGQPPPHSSAATPNLGPVGP 450

374 GQSTSRHKKLMFKTEGPDSD                              393
                                              ↔13
451 GMLNNHGHAVPANGEMSSSHSAQSMVSGSHCTPPPPYHADPSLVSFLTGL 500

↔14
501 GCPNCIEYFTSQGLQSIYHLQNLTIEDLGALKIPEQYRMTIWRGLQDLKQ 550

551 GHDYSTAQQLLRSSNAATISIGGSGELQRQRVMEAVHFRVRHTITIPNRG 600

601 GPGGGPDEWADFGFDLPDCKARKQPIKEEFTEAEIH              636
```

```
                                                                    INTRON1
  1        CACCTACTCC AGGGATGCCC CAGGCAGGCC CACTTGCCTG CGGCCCCCAC
 51        CGAGGCTGTC ACAGGAGGAC AGAGCACGAG TTCCCAGGGT GCTCAGGTGT
                                                                    EXON2
CCTCGG -STY1 101  CATTCCTTCC TTCCTGCAGA GCCAGCTGCC CTCGGAGGCC GGCGTGGGGA
CCTTGG +STY1                                    A
                                                T
      151  AGATGGCCCA GTCCACCGCC ACCTCCCCTG ATGGGGCAC CACGTTTGAG
      201  CACCTCTGGA GCTCTCTGTG AGTGCGCTTG GCTGGCCAGA GTGGGGGCC
      251  CCCCTGGGAG GCACTCTGGG CTAGCCTCAG CCACCTTCGC TGGGCTAACT
      301  GGGCCAGAGC AGGAGGGGTG GCCCCGGGAG GACTCTGGGC TAGCCCCAGC
      351  CACCCTCACT GAGACTTTGG GCTAAACTTG GCAACCCTCA CTGGGATTCT
      401  GGGCTAGCCT CGACCACCCT TGCTGCACTA ACTGGACCAG AGCAGGAGAG
      451  GTGGCTCCAC ACTAGTCTTG GGCTAGCCTT AGCCACCTTG ATCAGCTTGG
                                                                    INTRON2
      501  GGACAGGGCG GGTCGGAGGG GCAGGGAAGA GGGACTGCTG CCCTAGGCCT
      551  TCCCTGGGGA TGCAGGACCA AAATTCAGAC TCTTTTCTCT GGCCAGCTCT
      601  GGAGAGGGCC CATGGCCAGC AGAGGCCCAG AATAACAGAG CCCATGACTG
      651  GCTCTGCCTC TCTGGCACTC ACAGCAGCCG TGGAATGGCA GGTGGAGGAC
      701  AGAGATGGGA TGAGAGGGAA TGGGAAGGGC AGGAGACGTA GGCCTCACCA
      751  GGAGTCCAG GCTAGCCTTG AGCTCTGGGC CTGGGAGGTA TTGGGGTGAC
                                                                    EXON3
      801  ACCCAAACTG GGGACTGACG CTTCTATTTT CCTCTCCCTG CCCCAGGGAA
      851  CCAGACAGCA CCTTCCCCAG TCAAGCCGG...
```

```
sr-p70d-imr32                          CG ACCTTCCCCA GTCAAGCCGG GGGAATAATG  32
sr-p70a-ht29                           CG ACCTTCCCCA GTCAAGCCGG GGGAATAATG 150

AGGTGGTGGG CGGAACGGAT TCCAGCATGG ACGTCTTCCA CCTGGAGGGC  82
AGGTGGTGGG CGGAACGGAT TCCAGCATGG ACGTCTTCCA CCTGGAGGGC 200

ATGACTACAT CTGTCATGCA TCCTCGGCTC CTGCCTCACT AGCTGCGGAG 132
ATGACTACAT CTGTCAT.... .......... .......... .......... 217

CCTCTCCCGC TCGGTCCACG CTGCCGGGCG GCCACGACCG TGACCCTTCC 182
.......... .......... .......... .......... ..........

CCTCGGGCCG CCCAGATCCA TGCCTCGTCC CACGGGACAC CAGTTCCCTG 232
.......... .......... .......... .......... ..........

GCGTGTGCAG ACCCCCGGC GCCTACCATG CTGTACGTCG GTGACCCCGC 282
.......... .......... .......... .......... ..........

ACGGCACCTC GCCACGGCCC AGTTCAATCT GCTGAGCAGC ACCATGGACC 332
.......... .....GGCCC AGTTCAATCT GCTGAGCAGC ACCATGGACC 252

AGATGAGCAG CCGCGCGGCC TCGGCCAGCC CCTACACCCC AGAGCACGCC 382
AGATGAGCAG CCGCGCGGCC TCGGCCAGCC CCTACACCCC AGAGCACGCC 302

GCCAGCGTGC CCACCCACTC GCCCTACGCA CAACCCAGCT CCACCTTCGA 432
GCCAGCGTGC CCACCCAcTC GCCCTACGCA CAACCCAGCT CCACCTTCGA 352

CACCATGTCG CCGGCGCCTG TCATCCCCTC CAACACCGAC TACCCCGGAC 482
CACCATGTCG CCGGCGCCTG TCATCCCCTC CAACACCGAC TACCCCGGAC 402

CCCACCACTT TGAGGTCACT TTCCAGCAGT CCAGCACGGC CAAGTCAGCC 532
CCCACCACTT TGAGGTCACT TTCCAGCAGT CCAGCACGGC CAAGTCAGCC 452

ACCTGGACGT ACTCCCCGCT CTTGAAG
ACCTGGACGT ACTCCCCGCT CTTGAAG
```

```
sr-p70a  GCTGTGCCCGGGAAAGGCAAGGTCCGAAGCCCCCATCCCCCAGGCACCTCACAG  2300
sr-p70f  ...................................................  1870
sr-p70d  ...................................................  1764
sr-p70e  ...................................................  1521
sr-p70b  ...................................................  1817 sr-p70a  GCCCAGGAAAGGCCAGCCACCGCCCTGTGGACAGGCACCCTGAGTCA  2350
sr-p70f  ...............................................  1870
sr-p70d  ...............................................  1764
sr-p70e  ...............................................  1521
sr-p70b  ...............................................  1817 sr-p70a  CCTGCAGAACC  2361
sr-p70f  ...........  1870
sr-p70d  ...........  1764
sr-p70e  ...........  1521
sr-p70b  ...........  1817
```

FIG. 15J

```
sr-p70a  MAQSTATSPDGGTTFEHLWSSLEPDSTYFDLPQSSRGNNEVVGGTDSSMD    50
sr-p70f  ------------------------------------------------MD     2
sr-p70d  -------------------------------------------------M     1
sr-p70b  MAQSTATSPDGGTTFEHLWSSLEPDSTYFDLPQSSRGNNEVVGGTDSSMD    50
sr-p70e  -------------------------------------------------M     1 sr-p70a  VPHLEGNTTSVMAQFNLLSSTMDQMSSRAASASPYTPEHAASVPTHSPYA   100
sr-p70f  VPHLEGNTTSVMAQFNLLSSTMDQMSSRAASASPYTPEHAASVPTHSPYA    52
sr-p70d  LYVGDPARHLATAQFNLLSSTMDQMSSRAASASPYTPEHAASVPTHSPYA    51
sr-p70b  VPHLEGMTTSVMAQFNLLSSTMDQMSSRAASASPYTPEHAASVPTHSPYA   100
sr-p70e  LYVGDPARHLATAQFNLLSSTMDQMSSRAASASPYTPEHAASVPTHSPYA    51 sr-p70a  QPSSTFDTMSPAPVIPSNTDYPGPHHFEVTFQQSSTAKSATWTYSPLLKK   150
sr-p70f  QPSSTFDTMSPAPVIPSNTDYPGPHHFEVTFQQSSTAKSATWTYSPLLKK   102
sr-p70d  QPSSTFDTMSPAPVIPSNTDYPGPHHFEVTFQQSSTAKSATWTYSPLLKK   101
sr-p70b  QPSSTFDTMSPAPVIPSNTDYPGPHHFEVTFQQSSTAKSATWTYSPLLKK   150
sr-p70e  QPSSTFDTMSPAPVIPSNTDYPGPHHFEVTFQQSSTAKSATWTYSPLLKK   101 sr-p70a  LYCQIAKTCPIQIKVSTPPPGTAIRANPVYKKAEHVTDVVKRCPNHELG   200
sr-p70f  LYCQIAKTCPIQIKVSTPPPGTAIRANPVYKKAEHVTDVVKRCPNHELG   152
sr-p70d  LYCQIAKTCPIQIKVSTPPPGTAIRANPVYKKAEHVTDVVKRCPNHELG   151
sr-p70b  LYCQIAKTCPIQIKVSTPPPGTAIRANPVYKKAEHVTDVVKRCPNHELG   200
sr-p70e  LYCQIAKTCPIQIKVSTPPPGTAIRANPVYKKAEHVTDVVKRCPNHELG   151 sr-p70a  RDFNEGQSAPASHLITRVEGNNLSQYVDDPVTGRQSVVVPYEPPQVGTEFT   250
sr-p70f  RDFNEGQSAPASHLITRVEGNNLSQYVDDPVTGRQSVVVPYEPPQVGTEFT   202
sr-p70d  RDFNEGQSAPASHLITRVEGNNLSQYVDDPVTGRQSVVVPYEPPQVGTEFT   201
sr-p70b  RDFNEGQSAPASHLITRVEGNNLSQYVDDPVTGRQSVVVPYEPPQVGTEFT   250
sr-p70e  RDFNEGQSAPASHLITRVEGNNLSQYVDDPVTGRQSVVVPYEPPQVGTEFT   201
```

| | | |
|---|---|---|
| sr-p70a_ | GCPNCIEYFTSQGLQSIYHLQNLTIEDLGALKIPEQYRMTIWRGLQDLKQ | 550 |
| sr-p70f_ | GCPNCIEYFTSQGLQSIYHLQNLTIEDLGALKIPEQYRMTIWRGLQDLKQ | 502 |
| sr-p70d_ | GCPNCIEYFTSQGLQSIYHLQNLTIEDLGALKIPEQYRMTIWRGLQDLKQ | 501 |
| sr-p70b_ | ------------------------------------------------- | 499 |
| sr-p70e_ | -----------------QDLGALKIPEQYRMTIWRGLQDLKQ | 420 |

| | | |
|---|---|---|
| sr-p70a_ | GHDYSTAQQLLRSSNAATISIGGSGELQRQRVMEAVHFRVRHTITIPNRG | 600 |
| sr-p70f_ | GHDYSTAQQLLRSSNAATISIGGSGELQRQRVMEAVHFRVRHTITIPNRG | 552 |
| sr-p70d_ | GHDYSTAQQLLRSSNAATISIGGSGELQRQRVMEAVHFRVRHTITIPNRG | 551 |
| sr-p70b_ | ------------------------------------------------- | 499 |
| sr-p70e_ | GHDYSTAQQLLRSSNAATISIGGSGELQRQRVMEAVHFRVRHTITIPNRG | 470 |

| | | |
|---|---|---|
| sr-p70a_ | GPGGGPDEWADFGFDLPDCKARKQPIKEEFTEAEIH | 636 |
| sr-p70f_ | GPGGGPDEWADFGFDLPDCKARKQPIKEEFTEAEIH | 588 |
| sr-p70d_ | GPGGGPDEWADFGFDLPDCKARKQPIKEEFTEAEIH | 587 |
| sr-p70b_ | ----------------------------------- | 499 |
| sr-p70e_ | GPGGGPDEWADFGFDLPDCKARKQPIKEEFTEAEIH | 506 |

FIG. 16C

```
  1  TAACGCCCGCGGGGCCGGCTACTCCCCGCGGGGCCGCTCCCCTCCCGGCGCCTCCCGGCCCATATAACCCGC     60
 61  CTAGGGCCGGGGCCAGCCCGGGCCCTGCCTCCCCCGGGCCGGGCCGCTCCCCGGCCCACCCGGAGGCTCGGCGCG  120
121  CCCGCGAAGGGGACGCAGCGAAACCGGGCCCGGCGCCTGCGCAGCCGGGACGCAGCGACGCCGA            180
181  TGCCCGGGCCTGCGACGCGGCTGCCGACGCGGCTGCCCTTGGAGCGCCTTGGGACGTGGGGAAGATG           240
                                                                    M            1
241  GCCCAGTCCACCGCCACCTCCCCTGATGGGGGCACCACGTTTGAGCACCTCTGGAGCTCT                 300
  2   A   Q   S   T   A   T   S   P   D   G   G   T   T   F   E   H   L   W   S   S    21
301  CTGGAACCAGACAGCACCTACTTCGACCTTCCCCAGTCAAGCCGGGGAATAATGAGGTG                  360
 22   L   E   P   D   S   T   Y   F   D   L   P   Q   S   S   R   G   N   N   E   V    41
361  GTGGGCGGGAACGGATTCCAGCATGGACGTCTTCCACCTGGAGGGCATGACTACATCTGTC                420
 42   V   G   G   T   D   S   S   M   D   V   F   H   L   E   G   M   T   T   S   V    61
421  ATGGCCCAGTTCAATCTGCTGAGCAGCACCATGGACCAGATGAGCAGCCGCGCGGCCTCG                 480
 62   M   A   Q   F   N   L   L   S   S   T   M   D   Q   M   S   S   R   A   A   S    81
481  GCCAGCCCCTACACCCCAGAGCACGCGGCCAGCGTTCCCACCCACTCGCCTTACGCACAA                 540
 82   A   S   P   Y   T   P   E   H   A   A   S   V   P   T   H   S   P   Y   A   Q   101
541  CCCAGCTCCACCTTCGACACCATGTCGCCCGGCGCCCCTGTCATCCCCTCCAACACCGACTAC              600
102   P   S   S   T   F   D   T   M   S   P   A   P   V   I   P   S   N   T   D   Y   121
601  CCCGGACCCCACCACTTTGAGGTCACTTTCCAGCAGTCCAGTACGGCACGGAAGTCAGCCACC              660
122   P   G   P   H   H   F   E   V   T   F   Q   Q   S   S   T   A   K   S   A   T   141
661  TGGACGTA                                                                     
142   W   T
```

FIG. 17

… # PURIFIED SR-P70 PROTEIN

The invention relates to new nucleic acid sequences of the family of tumour-suppressing genes related to the gene for the p53 protein, and to the corresponding protein sequences.

The invention also relates to the prophylactic, therapeutic and diagnostic applications of these sequences, in particular in the field of pathologies linked to the phenomena of apoptosis or of cell transformation.

Tumour-suppressing genes perform a key role in protection against the phenomena of carcinogenesis, and any modification capable of bringing about the loss of one of these genes, its inactivation or its dysfunction may have oncogenic character, thereby creating favourable conditions for the development of a malignant tumour.

The authors of the present invention have identified transcription products of a new gene, as well as the corresponding proteins. This gene, SR-p70, is related to the p53 tumour-suppressing gene, the antitumour activity of which is linked to its transcription factor activity, and more specifically to the controls exerted on the activity of the Bax and Bcl-2 genes which are instrumental in the mechanisms of cell death.

Hence the present invention relates to purified SR-p70 proteins, or biologically active fragments of the latter.

The invention also relates to isolated nucleic acid sequences coding for the said proteins or their biologically active fragments, and to specific oligonucleotides obtained from these sequences.

It relates, in addition, to the cloning and/or expression vectors containing at least one of the nucleotide sequences defined above, and the host cells transfected by these cloning and/or expression vectors under conditions permitting the replication and/or expression of one of the said nucleotide sequences.

The methods of production of recombinant SR-p70 proteins or their biologically active fragments by the transfected host cells also form part of the invention.

The invention also comprises antibodies or antibody derivatives specific for the proteins defined above.

It relates, in addition, to methods of detection of cancers, either by measuring the accumulation of SR-p70 proteins in the tumours according to immunohistochemical techniques, or by demonstrating autoantibodies directed against these proteins in patients' serum.

The invention also relates to any inhibitor or activator of SR-p70 activity, for example of protein-protein interaction, involving SR-p70.

It also relates to antisense oligonucleotide sequences specific for the above nucleic acid sequences, capable of modulating in vivo the expression of the SR-p70 gene.

Lastly, the invention comprises a method of gene therapy, in which vectors such as, for example, inactivated viral vectors capable of transferring coding sequences for a protein according to the invention are injected into cells deficient for this protein, for purposes of regulating the phenomena of apoptosis or of reversion of transformation.

A subject of the present invention is a purified polypeptide comprising an amino acid sequence selected from:
 a) the sequence SEQ ID No. 2;
 b) the sequence SEQ ID No. 4;
 c) the sequence SEQ ID No. 6;
 d) the sequence SEQ ID No. 8;
 e) the sequence SEQ ID No. 10;
 f) the sequence SEQ ID No. 13;
 g) the sequence SEQ ID No. 15;
 h) the sequence SEQ ID No. 17;
 i) the sequence SEQ ID No. 19;
 j) any biologically active sequence derived from SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19.

In the description of the invention, the following definitions are used:
 SR-p70 protein: a polypeptide comprising an amino acid sequence selected from the sequences SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, or any biologically active fragment or derivative of this polypeptide;
 derivative: any variant polypeptide of the polypeptide of sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, or any molecule resulting from a modification of a genetic and/or chemical nature of the sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, that is to say obtained by mutation, deletion, addition, substitution and/or chemical modification of a single amino acid or of a limited number of amino acids, as well as any isoform sequence, that is to say sequence identical to the sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, or to one of its fragments or modified sequences, containing one or more amino acids in the form of the D enantiomer, the said variant, modified or isoform sequences having retained at least one of the properties that make them biologically active;
 biologically active: capable of binding to DNA and/or of exerting transcription factor activity and/or of participating in the control of the cell cycle, of differentiation and of apoptosis and/or capable of being recognized by the antibodies specific for the polypeptide of sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, and/or capable of inducing antibodies which recognize this polypeptide.

The manufacture of derivatives may have different objectives, including especially that of increasing the affinity of the polypeptide for DNA or its transcription factor activity, and that of improving its levels of production, of increasing its resistance to proteases, of modifying its biological activities or of endowing it with new pharmaceutical and/or biological properties.

Among the polypeptides of the invention, the polypeptide of human origin comprising the sequence SEQ ID No. 6, SEQ ID No. 13, SEQ ID No. 15, SEQ ID No. 17 or SEQ ID No. 19 is preferred. The polypeptide of 636 amino acids corresponding to the sequence SEQ ID No. 6 is more than 97% identical to the polypeptide of sequence SEQ ID No. 2.

The polypeptide of sequence SEQ ID No. 2 and that of sequence SEQ ID No. 4 are two expression products of the same gene, and the same applies to the sequences SEQ ID No. 8 and SEQ ID No. 10 and to the sequences SEQ ID No. 6, SEQ ID No. 13, SEQ ID No. 15, SEQ ID No. 17 or SEQ ID No. 19.

As will be explained in the examples, the polypeptide of sequence SEQ ID No. 4 corresponds to a premature termination of the peptide of sequence SEQ ID No. 2, linked to an alternative splicing of the longer transcript (messenger RNA), coding for the polypeptide of SEQ ID No. 2, of the corresponding gene. Similarly, in humans, the polypeptides corresponding to the sequences SEQ ID No. 6, SEQ ID No. 13, SEQ ID No. 15, SEQ ID No. 17 and SEQ ID No. 19, diverge in their composition in respect of the N- and/or C-terminal portions, this being the outcome of alternative splicing of the same primary transcript. The N-terminal peptide sequence of the sequence SEQ ID No. 10 is deleted, this being linked to an alternative splicing of its coding transcript.

Advantageously, the invention relates to a polypeptide corresponding to the DNA binding domain of one of the above polypeptides.

This domain corresponds to the sequence lying between residue 110 and residue 310 for the sequences SEQ ID No. 2 or 6, and between residue 60 and residue 260 for the sequence SEQ ID No. 8.

A subject of the present invention is also nucleic acid sequences coding for a SR-p70 protein or biologically active fragments or derivatives of the latter.

More preferably, a subject of the invention is an isolated nucleic acid sequence selected from:
a) the sequence SEQ ID No. 1;
b) the sequence SEQ ID No. 3;
c) the sequence SEQ ID No. 5;
d) the sequence SEQ ID No. 7;
e) the sequence SEQ ID No. 9;
f) the sequence SEQ ID No. 11;
g) the sequence SEQ ID No. 12;
h) the sequence SEQ ID No. 14;
i) the sequence SEQ ID No. 16;
j) the sequence SEQ ID No. 18;
k) the nucleic acid sequences capable of hybridizing specifically with the sequence SEQ ID No. 1, SEQ ID No. 3, SEQ ID No. 5, SEQ ID No. 7, SEQ ID No. 9, SEQ ID No. 11, SEQ ID No. 12, SEQ ID No. 14, SEQ ID No. 16 or SEQ ID No. 18 or with the sequences complementary to them, or of hybridizing specifically with their proximal sequences;
l) the sequences derived from the sequences a), b), c), d), e), f), g), h), i), j) or k) as a result of the degeneracy of the genetic code.

According to a preferred embodiment, a subject of the invention is nucleotide sequences SEQ ID No. 5, SEQ ID No. 12, SEQ ID No. 14, SEQ ID No. 16 and SEQ ID No. 18, corresponding, respectively, to the cDNAS of the human proteins of the sequences SEQ ID No. 6, SEQ ID No. 13, SEQ ID No. 15, SEQ ID No. 17 and SEQ ID No. 19.

The different nucleotide sequences of the invention may be of artificial origin or otherwise. They can be DNA or RNA sequences obtained by the screening of libraries of sequences by means of probes prepared on the basis of the sequences SEQ ID No. 1, 3, 5, 7, 9, 11, 12, 14, 16 or 18. Such libraries may be prepared by traditional techniques of molecular biology which are known to a person skilled in the art.

The nucleotide sequences according to the invention may also be prepared by chemical synthesis, or alternatively by mixed methods including the chemical or enzymatic modification of sequences obtained by the screening of libraries.

These nucleotide sequences enable nucleotide probes to be produced which are capable of hybridizing strongly and specifically with a nucleic acid sequence, of a genomic DNA or of a messenger RNA, coding for a polypeptide according to the invention or a biologically active fragment of the latter. Such probes also form part of the invention. They may be used as an in vitro diagnostic tool for the detection, by hybridization experiments, of transcripts specific for the polypeptides of the invention in biological samples, or for the demonstration of aberrant syntheses or of genetic abnormalities such as loss of heterozygosity or genetic rearrangement resulting from a polymorphism, from mutations or from a different splicing.

The probes of the invention contain at least 10 nucleotides, and contain at most the whole of the sequence of the SR-p70 gene or of its cDNA contained, for example, in a cosmid.

Among the shortest probes, that is to say of approximately 10 to 20 nucleotides, the appropriate hybridization conditions correspond to the stringent conditions normally used by a person skilled in the art.

The temperature used is preferably between $T_m$-5° C. and $T_m$-30° C., and as a further preference between $T_m$-5° C. and $T_m$-10° C., $T_m$ being the melting temperature, the temperature at which 50% of the paired DNA strands separate.

The hybridization is preferably conducted in solutions of high ionic strength, such as, in particular, 6×SSC solutions.

Advantageously, the hybridization conditions used are as follows:
temperature: 42° C.,
hybridization buffer: 6×SSC, 5× Denhart's, 0.1% SDS, as described in Example III.

Advantageously, these probes are represented by the following oligonucleotides or the sequences complementary to them:

```
SEQ ID No. 20:    GCG AGC TGC CCT CGG AG
SEQ ID No. 21:    GGT TCT GCA GGT GAC TCA G
SEQ ID No. 22:    GCC ATG CCT GTC TAC AAG
SEQ ID No. 23:    ACC AGC TGG TTG ACG GAG
SEQ ID No. 24:    GTC AAC CAG CTG GTG GGC CAG
SEQ ID No. 25:    GTG GAT CTC GGC CTC C
SEQ ID No. 26:    AGG CCG GCG TGG GGA AG
SEQ ID No. 27:    CTT GGC GAT CTG GCA GTA G
SEQ ID No. 28:    GCG GCC ACG ACC GTG AC
SEQ ID No. 29:    GGC AGC TTG GGT CTC TGG
SEQ ID No. 30:    CTG TAC GTC GGT GAC CCC
SEQ ID No. 31:    TCA GTG GAT CTC GGC CTC
SEQ ID No. 32:    AGG GGA CGC AGC GAA ACC
SEQ ID No. 33:    CCA TCA GCT CCA GGC TCT C
SEQ ID No. 34:    CCA GGA CAG GCG CAG ATG
SEQ ID No. 35:    GAT GAG GTG GCT GGC TGG A
SEQ ID No. 36:    TGG TCA GGT TCT GCA GGT G
SEQ ID No. 37:    CAC CTA CTC CAG GGA TGC
SEQ ID No. 38:    AGG AAA ATA GAA GCG TCA GTC
SEQ ID No. 39:    CAG GCC CAC TTG CCT GCC
SEQ ID No. 40:    CTG TCC CCA AGC TGA TGA G
```

Preferably, the probes of the invention are labelled prior to their use. To this end, several techniques are within the capacity of a person skilled in the art (fluorescent, radioactive, chemoluminescence, enzyme, and the like, labelling).

The in vitro diagnostic methods in which these nucleotide probes are employed are included in the subject of the present invention.

These methods relate, for example, to the detection of abnormal syntheses (e.g. accumulation of transcription products) or of genetic abnormalities, such as loss of heterozygosity and genetic rearrangement, and point mutations in the nucleotide sequences of nucleic acids coding for an SR-p70 protein, according to the definition given above.

The nucleotide sequences of the invention are also useful for the manufacture and use of oligonucleotide primers for sequencing reactions or specific amplification reactions according to the so-called PCR technique or any variant of the latter (ligase chain reaction (LCR), etc).

Preferred primer pairs consist of primers selected from the nucleotide sequences: SEQ ID No. 1: monkey sequence of 2,874 nucleotides, and SEQ ID No. 5: human SR-p70a cDNA, in particular upstream of the ATG translation initiation codon and downstream of the TGA translation stop codon.

Advantageously, these primers are represented by the following pairs:

```
pair No. 1:
                                       (SEQ ID No. 20)
sense primer: GCG AGC TGC CCT CGG AG
                                       (SEQ ID No. 21)
antisense primer: GGT TCT GCA GGT GAC TCA G pair No. 2:
                                       (SEQ ID No. 22)
sense primer: GCC ATG CCT GTC TAC AAG
                                       (SEQ ID No. 23)
antisense primer: ACC AGC TGG TTG ACG GAG pair No. 3:
                                       (SEQ ID No. 24)
sense primer: GTC AAC CAG CTG GTG GGC CAG
                                       (SEQ ID No. 25)
antisense primer: GTG GAT CTC GGC CTC C pair No. 4:
                                       (SEQ ID No. 26)
sense primer: AGG CCG GCG TGG GGA AG
                                       (SEQ ID No. 27)
antisense primer: CTT GGC GAT CTG GCA GTA G pair No. 5:
                                       (SEQ ID No. 28)
sense primer: GCG GCC ACG ACC GTG A
                                       (SEQ ID No. 29)
antisense primer: GGC AGC TTG GGT CTC TGG pair No. 6:
                                       (SEQ ID No. 30)
sense primer: CTG TAC GTC GGT GAC CCC
                                       (SEQ ID No. 31)
antisense primer: TCA GTG GAT CTC GGC CTC pair No. 7:
                                       (SEQ ID No. 32)
sense primer: AGG GGA CGC AGC GAA ACC
                                       (SEQ ID No. 29)
antisense primer: GGC AGC TTG GGT CTC TGG pair No. 8:
                                       (SEQ ID No. 41)
sense primer: CCCCCCCCCCCCCCN
(where N equals G, A or T)
                                       (SEQ ID No. 33)
antisense primer: CCA TCA GCT CCA GGC TCT C pair No. 9:
                                       (SEQ ID No. 41)
sense primer: CCCCCCCCCCCCCCN
(where N equals G, A or T)
                                       (SEQ ID No. 34)
antisense primer: CCA GGA CAG GCG CAG ATG pair No. 10:
                                       (SEQ ID No. 41)
sense primer: CCCCCCCCCCCCCCCN
(where N equals G, A or T)
                                       (SEQ ID No. 27)
antisense primer: CTT GGC GAT CTG GCA GTA G pair No. 11:
                                       (SEQ ID No. 37)
sense primer: CAC CTA CTC CAG GGA TGC
                                       (SEQ ID No. 38)
antisense primer: AGG AAA ATA GAA GCG TCA GTC pair No. 12:
                                       (SEQ ID No. 39)
sense primer: CAG GCC CAC TTG CCT GCC
                                       (SEQ ID No. 40)
antisense primer: CTG TCC CCA AGC TGA TGA G
```

These primers correspond to the sequences extending, respectively:

from nucleotide No. 124 to nucleotide No. 140 on SEQ ID No. 1 and from nucleotide No. 1 to nucleotide No. 17 on SEQ ID No. 5 for SEQ ID No. 20 from nucleotide No. 2280 to nucleotide No. 2262 on SEQ ID No. 1 and from nucleotide No. 2156 to nucleotide 2138 on SEQ ID No. 5 for SEQ ID No. 21 from nucleotide No. 684 to nucleotide No. 701 on SEQ ID No. 1 for SEQ ID No. 22 from nucleotide No. 1447 to nucleotide No. 1430 on SEQ ID No. 1 and from nucleotide 1324 to nucleotide 1307 on SEQ ID No. 5 for SEQ ID No. 23 from nucleotide 1434 to nucleotide 1454 on SEQ ID No. 1 and from nucleotide 1311 to nucleotide 1331 on SEQ ID No. 5 for SEQ ID No. 24 from nucleotide 2066 to nucleotide 2051 on SEQ ID No. 1 and from nucleotide 1940 to nucleotide 1925 on SEQ ID No. 5 for SEQ ID No. 25 from nucleotide 16 to nucleotide 32 on SEQ ID No. 5 for SEQ ID No. 26 from nucleotide 503 to nucleotide 485 on SEQ ID No. 5 for SEQ ID No. 27 from nucleotide 160 to nucleotide 176 on SEQ ID No. 11 for SEQ ID No. 28 from nucleotide 1993 to nucleotide 1976 on SEQ ID No. 5 for SEQ ID No. 29 from nucleotide 263 to nucleotide 280 on SEQ ID No. 11 for SEQ ID No. 30 from nucleotide 1943 to nucleotide 1926 on SEQ ID No. 5 for SEQ ID No. 31 from nucleotide 128 to nucleotide 145 on the nucleotide sequence depicted in FIG. 22 for SEQ ID No. 32 from nucleotide 1167 to nucleotide 1149 on SEQ ID No. 5 for SEQ ID No. 33 from nucleotide 928 to nucleotide 911 on SEQ ID No. 5 for SEQ ID No. 34 from nucleotide 677 to nucleotide 659 on SEQ ID No. 5 for SEQ ID No. 35 from nucleotide 1605 to nucleotide 1587 on SEQ ID No. 5 for SEQ ID No. 36 from nucleotide 1 to nucleotide 18 on the nucleotide sequence depicted in FIG. 13 for SEQ ID No. 37 from nucleotide 833 to nucleotide 813 on the nucleotide sequence depicted in FIG. 13 for SEQ ID No. 38 from nucleotide 25 to nucleotide 42 on the nucleotide sequence depicted in FIG. 13 for SEQ ID No. 39 from nucleotide 506 to nucleotide 488 on the nucleotide sequence depicted in FIG. 13 for SEQ ID No. 40

The nucleotide sequences according to the invention can have, moreover, uses in gene therapy, in particular for controlling the phenomena of apoptosis and of reversion of transformation.

The nucleotide sequences according to the invention may, moreover, be used for the production of recombinant SR-p70 proteins, according to the definition which has been given to this term.

These proteins may be produced from the nucleotide sequences defined above, according to techniques of production of recombinant products which are known to a person skilled in the art. In this case, the nucleotide sequence used is placed under the control of signals permitting its expression in a cell host.

An effective system for production of a recombinant protein necessitates having at one's disposal a vector, for example of plasmid or viral origin, and a compatible host cell.

The cell host may be selected from prokaryotic systems such as bacteria, or eukaryotic systems such as, for example, yeasts, insect cells, CHO cells (Chinese hamster ovary cells) or any other system advantageously available. A preferred cell host for the expression of proteins of the invention consists of the *E. coli* bacterium, in particular the strain MC 1061 (Clontec).

The vector must contain a promoter, translation initiation and termination signals and also the appropriate transcription regulation regions. It must be capable of being maintained stably in the cell and can, where appropriate, possess particular signals specifying the secretion of the translated protein.

These various control signals are selected in accordance with the cell host used. To this end, the nucleotide sequences according to the invention may be inserted into vectors which are autonomously replicating within the selected host, or vectors which are integrative for the chosen host. Such vectors will be prepared according to methods commonly used by a person skilled in the art, and the clones resulting therefrom may be introduced into a suitable host by standard methods such as, for example, electroporation.

The cloning and/or expression vectors containing at least one of the nucleotide sequences defined above also form part of the present invention.

A preferred cloning and expression vector is the plasmid pSE1, which contains the elements necessary for its use both as a cloning vector in *E. coli* (origin of replication in *E. coli* and ampicillin resistance gene originating from the plasmid pTZ 18R) and as an expression vector in animal cells (promoter, intron, polyadenylation site, origin of replication of the SV40 virus), as well as the elements enabling it to be copied as a single strand with the object of sequencing (origin of replication of phage f1).

The characteristics of this plasmid are described in Application EP 0,506,574.

Its construction and also the integration of the cDNAs originating from the nucleic acid sequences of the invention are, moreover, described in the examples below. According to a preferred embodiment, the proteins of the invention are in the form of fusion proteins, in particular in the form of a protein fused with glutathione S-transferase (GST). A designated expression vector in this case is represented by the plasmid vector pGEX-4T-3 (Pharmacia ref-27.4583).

The invention relates, in addition, to the host cells transfected by these aforementioned vectors. These cells may be obtained by introducing into host cells a nucleotide sequence inserted into a vector as defined above, followed by culturing of the said cells under conditions permitting the replication and/or expression of the transfected nucleotide sequence.

These cells are usable in a method of production of a recombinant polypeptide of sequence SEQ ID No. 2, SEQ ID No. 4, SEQ ID No. 6, SEQ ID No. 8, SEQ ID No. 10, SEQ ID No. 12, SEQ ID No. 14, SEQ ID No. 16 or SEQ ID No. 18 or any biologically active fragment or derivative of the latter.

The method of production of a polypeptide of the invention in recombinant form is itself included in the present invention, and is characterized in that the transfected cells are cultured under conditions permitting the expression of a recombinant polypeptide of sequence SEQ ID No. 2, SEQ ID No. 4, SEQ ID No. 6, SEQ ID No. 8, SEQ ID No. 10, SEQ ID No. 12, SEQ ID No. 14, SEQ ID No. 16 or SEQ ID No. 18 or of any biologically active fragment or derivative of the latter, and in that the said recombinant polypeptide is recovered.

The purification methods used are known to a person skilled in the art. The recombinant polypeptide may be purified from lysates and cell extracts or from the culture medium supernatant, by methods used individually or in combination, such as fractionation, chromatographic methods, immunoaffinity techniques using specific mono- or polyclonal antibodies, and the like. A preferred variant consists in producing a recombinant polypeptide fused to a "carrier" protein (chimeric protein). The advantage of this system is that it permits a stabilization and a decrease in proteolysis of the recombinant product, an increase in solubility during in vitro renaturation and/or a simplification of the purification when the fusion partner possesses an affinity for a specific ligand.

Advantageously, the polypeptides of the invention are fused with glutathione S-transferase at the N-terminal position (Pharmacia "GST" system). The fusion product is, in this case, detected and quantified by means of the enzyme activity of the GST. The colorimetric reagent used is a glutathione acceptor, a substrate for GST. The recombinant product is purified on a chromatographic support to which glutathione molecules have been coupled beforehand.

The mono- or polyclonal antibodies capable of specifically recognizing an SR-p70 protein according to the definition given above also form part of the invention. Polyclonal antibodies may be obtained from the serum of an animal immunized against protein, produced, for example, by genetic recombination according to the method described above, according to standard procedures.

The monoclonal antibodies may be obtained according to the traditional hybridoma culture method described by Köhler and Milstein, Nature, 1975, 256, 495-497.

Advantageous antibodies are antibodies directed against the central region lying between residue 110 and residue 310 for the sequences SEQ ID No. 2 or 6, or between residue 60 and residue 260 for the sequence SEQ ID No. 8.

The antibodies according to the invention are, for example, chimeric antibodies, humanized antibodies or Fab and F(ab')$_2$ fragments. They may also take the form of immunoconjugates or labelled antibodies.

Moreover, besides their use for the purification of the recombinant polypeptides, the antibodies of the invention, especially the monoclonal antibodies, may also be used for detecting these polypeptides in a biological sample.

Thus they constitute a means of immunocytochemical or immunohistochemical analysis of the expression of SR-p70 proteins on sections of specific tissues, for example by immunofluorescence, gold labelling or enzyme immunoconjugates.

They make it possible, in particular, to demonstrate an abnormal accumulation of SR-p70 proteins in certain tissues or biological samples, which makes them useful for detecting cancers or monitoring the progression or remission of preexisting cancers.

More generally, the antibodies of the invention may be advantageously employed in any situation where the expression of an SR-p70 protein has to be observed.

Hence the invention also relates to a method of in vitro diagnosis of pathologies correlated with an expression or an abnormal accumulation of SR-p70 proteins, in particular the phenomena of carcinogenesis, from a biological sample, characterized in that at least one antibody of the invention is brought into contact with the said biological sample under conditions permitting the possible formation of specific immunological complexes between an SR-p70 protein and the said antibody or antibodies, and in that the specific immunological complexes possibly formed are detected.

The invention also relates to a kit for the in vitro diagnosis of an expression or an abnormal accumulation of SR-p70 proteins in a biological sample and/or for measuring the level of expression of this protein in the said sample, comprising:

at least one antibody specific for an SR-p70 protein, optionally bound to a support, means of visualization of the formation of specific antigen-antibody complexes between an SR-p70 protein and the said antibody, and/or means of quantification of these complexes.

The invention also relates to a method of early diagnosis of tumour formation, by detecting autoantibodies directed against an SR-p70 protein in an individual's serum.

Such a method of early diagnosis is characterized in that a serum sample drawn from an individual is brought into contact with a polypeptide of the invention, optionally bound to a support, under conditions permitting the formation of specific immunological complexes between the said polypeptide and the autoantibodies possibly present in the serum sample, and in that the specific immunological complexes possibly formed are detected.

A subject of the invention is also a method of determination of an allelic variability, a mutation, a deletion, an insertion, a loss of heterozygosity or a genetic abnormality of the SR-p70 gene which may be involved in pathologies, characterized in that it utilizes at least one nucleotide sequence described above. Among the methods of determination of an allelic variability, a mutation, a deletion, an insertion, a loss of heterozygosity or a genetic abnormality of the SR-p70 gene, preference is given to the method which is characterized in that it comprises at least one step of PCR amplification of the target nucleic acid sequence of SR-p70 liable to exhibit a polymorphism, a mutation, a deletion or an insertion, using a pair of primers of nucleotide sequences defined above, a step during which the amplified products are treated using a suitable restriction enzyme and a step during which at least one of the products of the enzyme reaction is detected or assayed.

The invention also comprises pharmaceutical compositions comprising as active principle a polypeptide corresponding to the above definitions, preferably in soluble form, in combination with a pharmaceutically acceptable vehicle.

Such compositions afford a novel approach to treating the phenomena of carcinogenesis at the level of the control of multiplication and cell differentiation.

Preferably, these compositions can be administered systemically, preferably intravenously, intramuscularly, intradermally or orally.

Their optimal modes of administration, dosages and pharmaceutical dosage forms may be determined according to the criteria generally borne in mind in establishing a therapeutic treatment suitable for a patient, such as, for example, the patient's age or body weight, the severity of his or her general state, the tolerability of treatment and the observed side effects, and the like.

Lastly, the invention comprises a method of gene therapy, in which nucleotide sequences coding for an SR-p70 protein are transferred to target cells by means of inactivated viral vectors.

Other features and advantages of the invention are to be found in the remainder of the description, with the examples and the figures for which the legends are given below.

BRIEF DESCRIPTION OF THE DRAWINGS

FIGS. 1A and 1B: Nucleic acid comparison of monkey SR-p70a cDNA (corresponding to nucleotides 1-1599 of SEQ ID No. 1) with the nucleic acid sequence of monkey p53 cDNA (SEQ ID No. 43).

FIG. 2: Protein comparison of monkey SR-p70a amino acids 1-450 of SEQ ID No. 1 with monkey p53 protein (SEQ ID No. 44) (sw: p53-cerae).

FIGS. 3A-C: Comparison of the nucleic acid sequence of monkey SR-p70a and b cDNA (corresponding, respectively, to SEQ ID No. 1 and SEQ ID No. 3).

FIGS. 4A and 4B: Nucleic acid sequence (SEQ ID No. 1) and deduced protein sequence (SEQ ID No. 2) of monkey SR-p70a.

FIG. 5: Partial nucleic acid sequence (SEQ ID No. 3) and complete deduced protein sequence (SEQ ID No. 4) of monkey SR-p70b.

FIGS. 6A and 6B: Partial nucleic acid sequence (SEQ ID No. 5) and deduced complete protein sequence (SEQ ID No. 6) of human SR-p70a.

FIG. 7: Partial nucleic acid sequence (SEQ ID No. 7) and complete deduced protein sequence (SEQ ID No. 8) of mouse SR-p70c.

FIG. 8: Partial nucleic acid sequence (SEQ ID No. 9) and partially deduced protein sequence (SEQ ID No. 10) of mouse SR-p70a.

FIGS. 9A and 9B: Multialignment of the proteins deduced from monkey (SR-p70a-cos3 and SR-p70b-cos3) (SEQ ID No. 2 and SEQ ID No. 4, respectively), human (SR-p70-ht29) and mouse (SR-p70c-att20 and sr-p70a-att20) (SEQ ID No. 10 and SEQ ID No. 8, respectively) SR-p70 cDNAs.

FIG. 12: Genomic structure of the SR-p70 gene and comparison with that of the p53 gene. The human protein sequences of SR-p70a (SEQ ID No. 6) (upper line of the alignment) and of p53 (SEQ ID No. 45) (lower line) are divided up into peptides on the basis of the respective exons from which they are encoded. The figures beside the arrows correspond to the numbering of the corresponding exons.

FIG. 13: Human genomic sequence of SR-p70 from the 3' end of intron 1 to the 5' end of exon 3 (SEQ ID No. 46). The introns are boxed. At positions 123 and 133, two variable nucleic acid positions are localized (G→A at 123 and C→T at 133). The restriction sites for the enzyme StyI are underlined (position 130 in the case where a T is present instead of a C at position 133, position 542 and position 610). The arrows indicate the positions of the nucleic acid primers used in Example XI.

FIG. 14: Nucleic acid comparison of the 5' region of the human cDNAs of SR-p70d (SEQ ID No. 12) and of SR-p70a (SEQ ID No. 5).

FIGS. 15A-J: Multialignment of the nucleic acid sequences corresponding to human SR-p70a, b, d, e, and f (SEQ ID No. 5, SEQ ID No. 18, SEQ ID No. 12, SEQ ID No. 14 and SEQ ID No. 16, respectively).

FIGS. 16A-C: Multialignment of the proteins deduced from human SR-p70 (a, b, d, e and f) (SEQ ID No. 6, SEQ ID No. 19, SEQ ID No. 13, SEQ ID No. 15 and SEQ ID No. 17, respectively), cDNA's.

FIG. 17: Partial nucleic acid sequence (SEQ ID No. 5) and partial deduced protein sequence (SEQ ID No. 6) of human SR-p70a. The two bases in bold characters correspond to two variable positions (see FIG. 6). This sequence possesses a more complete non-coding 5' region than the one presented in FIG. 6.

FIG. 20: Diagrammatic representation with a partial restriction map of the plasmid pcDNA3 containing human SR-p70a.

EXAMPLE I

Figure 10A:
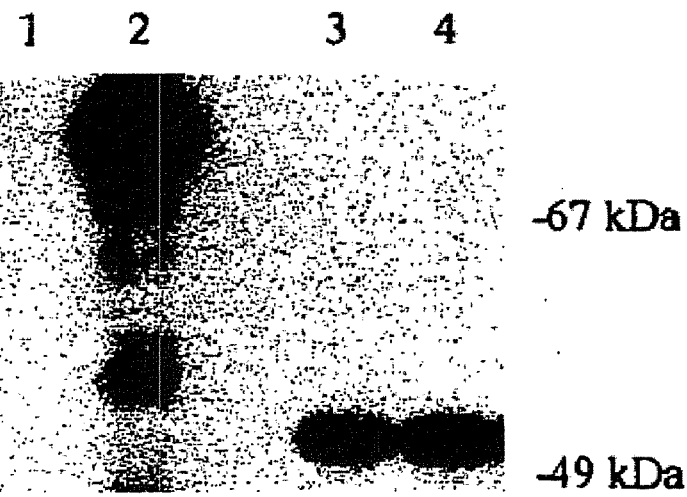
FIG. 10a: Immunoblot of the SR-p70 protein.

Cloning of SR-p70 cDNA from COS-3 Cells

1. Culturing of COS-3 Cells

COS-3 cells (African green monkey kidney cells transformed with the SV 40 virus T antigen) are cultured in DMEM medium (GIBCO-BRL reference 41 965-047) containing 2 mM L-glutamine and supplemented with 50 mg/l of gentamicin and 5% of foetal bovine serum (GIBCO-BRL reference 10231-074) to semi-confluence.

2. Preparation of the Messenger RNA a) Extraction of the Messenger RNA

The cells are recovered in the following manner:
the adherent cells are washed twice with PBS buffer (phosphate buffered saline, reference 04104040-GIBCO-BRL), then scraped off with a rubber scraper and centrifuged.

The cell pellet is suspended in the lysis buffer of the following composition: 4 M guanidine thiocyanate; 25 mM sodium citrate pH 7; 0.5% sarcosyl; 0.1 M β-mercaptoethanol. The suspension is sonicated using an Ultra-Turrax No. 231256 sonicator (Janke and Kundel) at maximum power for one minute. Sodium acetate pH 4 is added to a concentration of 0.2 M. The solution is extracted with one volume of a phenol/chloroform (5:1 v/v) mixture. The RNA contained in the aqueous phase is precipitated at −20° C. using one volume of isopropanol. The pellet is resuspended in the lysis buffer. The solution is extracted again with a phenol/chloroform mixture and the RNA is precipitated with isopropanol. After washing of the pellet with 70% and then 100% ethanol, the RNA is resuspended in water.

b) Purification of the Poly(A)+ Fraction of the RNA

Purification of poly(A)+ fraction of the RNA is carried out using the DYNAL Dynabeads oligo(dT)$_{25}$ kit (reference 610.05) according to the protocol recommended by the manufacturer. The principle is based on the use of superparamagnetic polystyrene beads to which an oligonucleotide poly(dT)$_{25}$ is attached. The poly(A)+ fraction of the RNA is hybridized with the oligo(dT)$_{25}$ coupled to the beads, which are trapped on a magnetic support.

3. Production of the Complementary DNA Library a) Preparation of the complementary DNA From 0.5 μg of the poly(A)+ RNA from COS-3 cells obtained at the end of step 2, the [$^{32}$P]dCTP-labelled single-stranded complementary DNA is prepared (the complementary DNA obtained possesses a specific activity of 3000 dpm/ng) with the synthetic primer of the following sequence (comprising a BamHI site):

```
5'<GATCCGGGCC CTTTTTTTTT TTT<3'    (SEQ ID No. 47)
``` in a volume of 30 μl of buffer of composition: 50 mM Tris-HCl pH 8.3, 6 mM MgCl$_2$, 10 mM DDT, 40 mM KCl, containing 0.5 mM each of the deoxynucleotide triphosphates, 30 μCi of [α-$^{32}$P]dCTP and 30 U of RNasin (Promega). After one hour of incubation at 37° C., then 10 minutes at 50° C., then 10 minutes again at 37° C., with 200 units of the enzyme reverse transcriptase RNase if (GIBCO-BRL reference 8064A), 4 nl of EDTA are added.

b) Alkaline Hydrolysis of the RNA Template

6 μl of 2N NaOH solution are added and the mixture is then incubated for 5 minutes at 65° C.

c) Purification on a Sephacryl S-400 Column

In order to remove the synthetic primer, the complementary DNA is purified on a column of 1 ml of Sephacryl S-400 (Pharmacia) equilibrated in TE buffer.

The first two radioactive fractions are pooled and precipitated with ⅒ volume of 10 M ammonium acetate solution and 2.5 volumes of ethanol, this being done after extraction with one volume of chloroform.

d) Homopolymer Addition of dG

The complementary DNA is elongated at the 3' end with a dG tail with 20 units of the enzyme terminal transferase (Pharmacia 27073001). The mixture is incubated in 20 μl of buffer of composition: 30 mM Tris-HCl pH 7.6, 1 mM cobalt chloride, 140 mM cacodylic acid, 0.1 mM DTT, 1 mM dGTP, for 15 minutes at 37° C., and 2 μl of 0.5 M EDTA are then added.

e) Steps b) and c) are Repeated Again f) Pairing of the cloning vector pSE1 (EP 506,574) and the complementary DNA in the presence of the adaptor.

The mixture is centrifuged, the pellet is dissolved in 33 μl of TE buffer, 5 μl (125 ng) of cloning vector pSE1, 1 μl (120 ng) of the adaptor of the following sequence (comprising an ApaI site):

```
5'AAAAAAAAAAAAAGGGCCCG3'    (SEQ ID No. 48)
``` and 10 μl of 200 mM NaCl solution are added, and the reaction mixture is incubated for 5 minutes at 65° C. and then allowed to cool to room temperature.

g) Ligation

The cloning vector and the single-stranded cDNA are ligated in a volume of 100 µl with 32.5 units of the enzyme phage T4 DNA ligase (Pharmacia reference 270 87002) overnight at 15° C. in a buffer of composition: 50 mM Tris-HCl pH 7.5, 10 mM MgCl$_2$, 1 mM ATP.

h) Synthesis of the Second Strand of the cDNA

The proteins are removed by phenol extraction followed by chloroform extraction, and 1/10 volume of 10 mM ammonium acetate solution and then 2.5 volumes of ethanol are then added. The mixture is centrifuged, the pellet is dissolved in a buffer of composition 33 mM Tris-acetate pH 7.9, 62.5 mM potassium acetate, 1 mM magnesium acetate and 1 mM dithiothreitol (DTT), and the second strand of complementary DNA is synthesized in a volume of 30 µl with 30 units of the enzyme phage T4 DNA polymerase (Pharmacia reference 270718) and a mixture of 1 mM the four deoxynucleotide triphosphates dATP, dCTP, dGTP and dTTP as well as two units of phage T4 gene 32 protein (Pharmacia reference 27-0213) for one hour at 37° C. The mixture is extracted with phenol and the traces of phenol are removed with a column of polyacrylamide P10 (Biogel P10-200-400 mesh—reference 15011050—Biorad).

i) Transformation by Electroporation

E. coli MC 1061 cells are transformed with the recombinant DNA obtained above by electroporation using a Biorad Gene Pulser apparatus (Biorad) used at 2.5 kV under the conditions specified by the manufacturer, and the bacteria are then grown for one hour in the medium known as LB medium (Sambrook op. cit.) of composition: bactotryptone 10 g/l; yeast extract 5 g/l; NaCl 10 g/l.

The number of independent clones is determined by plating out a 1/1000 dilution of the transformation after the first hour of incubation on a dish of LB medium with the addition of 1.5% of agar (w/v) and 100 µg/ml of ampicillin, hereinafter referred to as LB agar medium. The number of independent clones is 1 million.

j) Analysis of the cDNAs of the Library

In the context of the analysis of individual clones of the library by nucleic acid sequencing of the 5' region of the cDNAs, one clone, designated SR-p70a, was shown to exhibit a partial homology with the cDNA of the already known protein, the p53 protein (Genbank X 02469 and X 16384) (FIG. 1). The sequences were produced with the United States Biochemical kit (reference 70770) and/or the Applied Biosystems kit (references 401434 and/or 401628), which use the method of Sanger et al., Proc. Natl. Acad. Sci. USA; 1977, 14, 5463-5467. The plasmid DNA is prepared from the WIZARD mini-preparation kit (Promega reference A7510). The primers used are 16- to 22-mer oligonucleotides, complementary either to the vector pSE1 in the region immediately at the 5' end of the cDNA, or to the sequence of the cDNA.

A second cDNA was isolated from the same library by screening, in a manner similar to the technique described in EXAMPLE III.3 below, with a fragment of SR-p70a the DNA labelled with $^{32}$P with the BRL "Random Primers DNA labelling systems" kit (reference 18187-013). The hybridization and washing buffers are treated by adding 50% of formamide. The last wash is carried out in 0.1×SSC/0.1% SDS at 60° C. This second sequence (SR-p70b cDNA) is identical to the first but an internal fragment has been deleted from it (FIG. 3).

The two SR-p70 cDNAs, of length 2874 nucleotides (SR-p70a) and 2780 nucleotides (SR-p70b), correspond to the products of a single gene, an alternative splicing bringing about a deletion of 94 bases between nucleotides 1637 and 1732 and a premature termination of the corresponding encoded protein. The proteins deduced from the two cDNAs possess 637 amino acids and 499 amino acids, respectively (FIGS. 4 and 5).

EXAMPLE II

Obtaining of the Sequence and Cloning of the cDNA of the SR-p70a Protein from HT-29 (Human Colon Adenocarcinoma) Cells 1) Culturing of HT-29 Cells The cells are cultured in McCoy's 5 medium (GIBCO 26600-023) with the addition of 10% of foetal calf serum (GIBCO 10081-23) and 50 mg/l of gentamicin, to semi-confluence.

2) Preparation of the Complementary DNA

The messenger RNA is prepared as described in EXAMPLE I.2. The cDNA is prepared in a manner similar to that described in EXAMPLE I.3, with 5 µg of total messenger RNA, using a poly(T)$_{12}$ primer. The reaction is not interrupted with EDTA.

3) Specific Amplification of the Human cDNA by the so-called PCR Technique

The polymerization is carried out with 4 µl of cDNA in 50 µl final with the buffer of the following composition: 10 mM Tris-HCl pH 8.3, 2.5 mM MgCl$_2$, 50 mM KCl in the presence of 10% DMSO, 0.5 mM dNTP, 4 µg/ml of each of the two nucleic acid primers and 2.5 units of TAQ DNA polymerase (Boehringer). The primer pairs were selected on the basis of the nucleic acid sequence of the COS-3 SR-p70 clone, in particular upstream of the translation initiation ATG and downstream of the translation stop TGA, and are of the following compositions:

```
                                        (SEQ ID No. 49)
sense primer:
ACT GGT ACC GCG AGC TGC CCT CGG AG
    Kpn I restriction site (SEQ ID No. 50)
antisense primer:
GAC TCT AGA GGT TCT GCA GGT GAC TCA G
    Xba I restriction site
```

The reaction is carried out for 30 cycles of 94° C./1 minute, 54-60° C./1 minute 30 seconds and 72° C./1 minute 30 seconds, followed by a final cycle of 72° C./6 minutes.

4) Obtaining of the Sequence of the Human cDNA

In a first step, the PCR product is removed from the oligonucleotides on a column of Sephacryl S-400, and then desalted by exclusion chromatography on a column of polyacrylamide P10 (Biorad reference 1504144). The sequencing reactions are carried out using the Applied Biosystems kit (reference 401628) with oligonucleotides specific for the cDNA. The sequence obtained is very similar to that of monkey SR-p70a, and the deduced protein contains 636 amino acids (FIG. 6).

In a similar manner, other sequences originating from human lines or tissues were obtained for the coding portion of human SR-p70, in particular from the lung or pancreas. The proteins deduced from these sequences are identical to those obtained for the HT-29 line.

5) Cloning of the Human cDNA into Plasmid pCDNA3 (Invitrogen V 790-20)

The PCR product obtained in 3) and also the plasmid are digested with the two restriction enzymes Kpn I and Xba I and then purified after migration on a 1% agarose gel using the Geneclean kit (Bio 101 reference 3105). After ligation with 100 ng of insert and 10 ng of vector and transformation (technique described in EXAMPLE I.3.g and i), the recombinant clones are verified by sequencing using the Applied Biosystems kit mentioned above.

EXAMPLE III

Cloning of Mouse SR-p70 cDNA from AtT-20 (Pituitary Tumour) Cells

1) Cell Culturing of the Line AtT-20

The cells are cultured in Ham F10 medium (GIBCO 31550-023) with the addition of 15% of horse serum (GIBCO 26050-047), 2.5% of foetal calf serum (GIBCO 10081-073) and 50 mg/l of gentamicin, to semi-confluence.

2) Preparation of the Complementary DNA Library

The library is produced as described in EXAMPLE I.2 and 3 from the cells cultured above.

3) Screening of the Library a) Preparation of the Membranes

The clones of the library are plated out on LB agar medium (Petri dishes 150 mm in diameter) coated with Biodyne A membranes (PALL reference BNNG 132). After one night at 37° C., the clones are transferred by contact onto fresh membranes. The latter are treated by depositing them on 3 mm Whatman paper soaked with the following solutions: 0.5 N NaOH, 1.5 M NaCl for 5 minutes, then 0.5 M Tris-HCl pH 8, 1.5 M NaCl for 5 minutes. After treatment with proteinase K in the following buffer: 10 mM Tris-HCl p8, 10 mM EDTA, 50 mM NaCl, 0.1% SDS, 100 µg/ml proteinase K, for one hour at room temperature, the membranes are washed copiously in 2×SSC (sodium citrate, NaCl), dried and then incubated in an oven under vacuum at 80° C. for 20 minutes.

b) Preparation of the probe

On the basis of monkey and human SR-p70 cDNA sequences, a first sequence was produced on a fragment amplified from line AtT-20 mRNA as described in EXAMPLE 11.3 and 4, with the oligomers of the following compositions:

```
                                    (SEQ ID No. 22)
sense primer:       GCC ATG CCT GTC TAC AAG (SEQ ID No. 23)
antisense primer:   ACC AGC TGG TTG ACG GAG.
```

On the basis of this sequence, an oligomeric probe specific for mouse was chosen and possesses the following composition:

```
GAG CAT GTG ACC GAC ATT G.      (SEQ ID No. 50)
```

100 ng of the probe are labelled at the 3' end with 10 units of terminal transferase (Pharmacia) and 100 µCi of [α-$^{32}$P] dCTP 3000 Ci/mmol (Amersham reference PB 10205) in 10 µl of the following buffer: 30 mM Tris-HCl pH 7.6, 140 mM cacodylic acid, 1 mM CoCl$_2$, 0.1 mM DTT for 15 minutes at 37° C. The radiolabelled nucleotides not incorporated are removed on a column of polyacrylamide P10 (Biorad, reference 1504144). The probe obtained has a specific activity of approximately 5×10$^8$ dpm/µg.

c) Prehybridization and Hybridization

The membranes prepared in a) are prehybridized for 30 minutes at 42° C. in 6×SSC, 5× Denhart's, 0.1% SDS, and then hybridized for a few hours in the same buffer with the addition of the probe prepared in b) in the proportion of 10$^6$ dpm/ml.

d) Washing and Exposure of the Membranes

The membranes are washed twice at room temperature in 2×SSC/0.1% SDS buffer and then for one hour at 56° C. in 6×SSC/0.1% SDS. The hybridized clones are visualized with KODAK XOMAT films. A positive clone containing the mouse SR-p70 is selected and hereinafter designated as SR-p70c.

4) Sequencing of Mouse SR-p70 and Analysis of the Sequence

The sequence is obtained using the Applied Biosystem kit (reference 401628). The protein sequence deduced from mouse SR-p70c cDNA (FIG. 7) exhibits a very strong homology with the human and monkey sequences, except in the N-terminal portion which diverges strongly (see FIG. 9). Using the so-called PCR technique in a similar manner to that described in EXAMPLE II.3 and 4, a second 5' sequence (originating from the same AtT-20 library) was obtained (FIG. 8). The deduced N-terminal protein sequence (sequence designated SR-p70a) is very similar to that deduced from human and monkey SR-p70 cDNAs (SR-p70a) (FIG. 9). The line AtT-20 hence affords at least two SR-p70 transcripts. The latter 2 diverge in the N-terminal portion through different splicings.

EXAMPLE IV

1) Production of Recombinant SR-p70 Protein in *E. coli* a) Construction of the Expression Plasmid

This consists in placing the COOH-terminal portion of the monkey SR-p70a protein, from the valine at position 427 to the COOH-terminal histidine at position 637, in fusion with the glutathione S-transferase (GST) of the plasmid vector pGEX-4T-3 (Pharmacia reference 27-4583). For this purpose, the corresponding insert of SR-p70a (position 1434 to 2066) was amplified by PCR with 10 ng of plasmid containing monkey SR-p70a cDNA. The nucleic acid primers are of the following composition:

```
sense primer:
                                    (SEQ ID No. 52)
    TTT GGA TCC GTC AAC CAG CTG GTG GGC CAG
       BamHI restriction site antisense primer:
                                    (SEQ ID No. 52)
    AAA GTC GAC GTG GAT CTC GGC CTC C.
       Sal I site
```

The fragment obtained and also the vector are digested with the restriction enzymes BamHI and Sal I and cloning is carried out as described in EXAMPLE II.5. The selected clone is referred to as pG SR-p70.

b) Expression and Purification of the GST-pSR-p70 Fusion Protein

This step was carried out using the "bulk GST purification module" kit (Pharmacia Reference 27-4570-01).

In outline, the recombinant clone was cultured at 37° C. in one litre of 2×YTA medium+100 µg/ml ampicillin. At OD 0.8, expression is induced with 0.5 mM IPTG for 2 hours at 37° C. After centrifugation, the cell pellet is taken up in cold PBS and then sonicated by ultrasound. After the addition of 1% Triton X-100, the preparation is incubated for 30 minutes with agitation at room temperature. After centrifugation at 12,000 g for 10 minutes at 4° C., the supernatant is recovered. Purification is then carried out on a glutathione-Sepharose 4B affinity chromatography column. Binding and washing are carried out in PBS buffer and elution is carried out by competition with reduced glutathione. The final concentration is brought to 300 µg/ml of fusion protein.

2) Production of SR-p 70a Protein in COS-3 Cells

COS-3 cells are transfected with pSE1 plasmid DNA into which monkey SR-p70a cDNA has been cloned (EXAMPLE I.1), or with the vector pSE1 plasmid DNA as control, by the DEAE-dextran technique: the COS-3 cells are inoculated at $5 \times 10^5$ cells per 6 cm dish in culture medium containing 5% of foetal bovine serum (EXAMPLE I.1). After culture, the cells are rinsed with PBS. 1 ml of the following mixture is added: medium containing 6.5 µg of DNA, 250 µg/ml of DEAE-dextran and 100 µM chloroquine. The cells are incubated at 37° C. in 5% $CO_2$ for 4 to 5 hours. The medium is aspirated off, 2 ml of PBS containing 10% of DMSO are added and the cells are incubated for one minute, shaking the dishes gently. The medium is aspirated off again and the cells are rinsed twice with PBS. The cells are then incubated at 37° C. with medium containing 2% of foetal bovine serum for the period during which expression takes place, which is generally 3 days.

The SR-p70a protein is then analysed as described in EXAMPLE IV by immunoblotting.

EXAMPLE V

Preparation of Specific Antibodies

150 µg of proteins of the sample prepared according to EXAMPLE IV were used to immunize a rabbit (New Zealand male weighing 1.5 to 2 kg approximately). The immunizations were performed every 15 days according to the protocol described by Vaitukaitis, Methods in Enzymology, 1981, 73, 46. At the first injection, one volume of antigenic solution is emulsified with one volume of Freund's complete adjuvant (Sigma reference 4258). Five boosters were administered in Freund's incomplete adjuvant (Sigma reference 5506).

EXAMPLE VI

Detection of the SR-p70 Protein: Western Immunoblotting

1) Materials Used for Immunoblotting a) Cell Lines Used for Immunoblotting

The following cell lines were cultured as described in the catalogue "Catalogue of cell lines and hybridomas, 7th edition, 1992" of the ATCC (American Type Culture Collection): COS-3, CV-1 (monkey kidney cell line), HT-29, U-373MG (human glioblastoma), MCF7 (human mammary adenocarcinoma), SKNAS (human neuroblastoma cultured under the same conditions as COS-3), SK-N-MC (human neuroblastoma), IMR-32 (human neuroblastoma), CHP212 (human neuroblastoma cultured under the same conditions as CV-1), Saos-2 (osteosarcoma), SK-OV-3 (ovarian adenocarcinoma) and SW 480 (human colon adenocarcinoma).

b) COS-3 Cells Transfected by SR-p70a cDNA

COS-3 cells were transfected as described in EXAMPLE IV.2. As a control, the cells were transfected with pSE1 plasmid DNA not containing recombinant SR-p70a cDNA.

2) Preparation of Protein Samples from a Eukaryotic Cell Culture or from Transfected Cells After culture, the cells are washed with PBS and then taken up in RIPA buffer (PBS with 1% NP40, 0.5% sodium deoxycholate, 0.5% SDS) supplemented with 10 µg/ml RNAse A, 20 µg/ml DNAse 1, 2 µg/ml aprotinin, 0.5 µg/ml leupeptin, 0.7 µg/ml pepstatin and 170 µg/ml PMSF. The cells are sonicated by ultrasound at 4° C. and left for 30 minutes at 4° C. After microcentrifugation at 12,000 rpm, the supernatant is recovered. The protein concentration is measured by the Bradford method.

3) Western Blotting 5 or 50 µg of proteins (50 µg for the cell lines and 5 µg for transfected cells) are placed in 0.2 volume of the following 6× electrophoresis buffer: 0.35 mM Tris-HCl pH 6.8, 10.3% SDS, 36% glycerol, 0.6 mM DTT, 0.012% bromophenol blue. The samples are applied and run in a 10% SDS-PAGE gel (30:0.8 Bis) and then electrotransferred onto a nitrocellulose membrane.

4) Visualization with the Antibody

The membrane is incubated for 30 minutes in TBST blocking buffer (10 mM Tris-HCl pH 8, 150 mM NaCl, 0.2% Tween 20) with the addition of 5% of milk (GIBCO—SKIM MILK) at room temperature. The membrane is brought into contact successively with the anti-SR-p70 (αSR-p70) antibody in the same buffer for 16 hours at 4° C., washed 3 times for 10 minutes with TBST and then incubated for one hour at 37° C. with a second, anti-rabbit immunoglobulin antibody coupled to peroxidase (SIGMA A055). After three washes of 15 minutes, the visualization is performed using the ECL kit (Amersham RPN2106) by chemiluminescence.

In parallel, the same samples were subjected to visualization with an anti-p53 (αp53) antibody (Sigma BP5312) followed by a second, anti-mouse immunoglobulin antibody.

5) Figures and results

FIG. 10: Immunoblot of the SR-p70 Protein

FIG. 10a: Detection of the recombinant SR-p70 protein
  columns 1 and 3: COS-3 transfected by the vector pSE1.
  columns 2 and 4: COS-3 transfected by plasmid pSE1 containing SR-p70a cDNA.
  columns 1 and 2: visualization with the anti-SR-p70 (αSR-p70) antibody.
  columns 3 and 4: visualization with the anti-p53 (αp53) antibody.

Figure 10B:
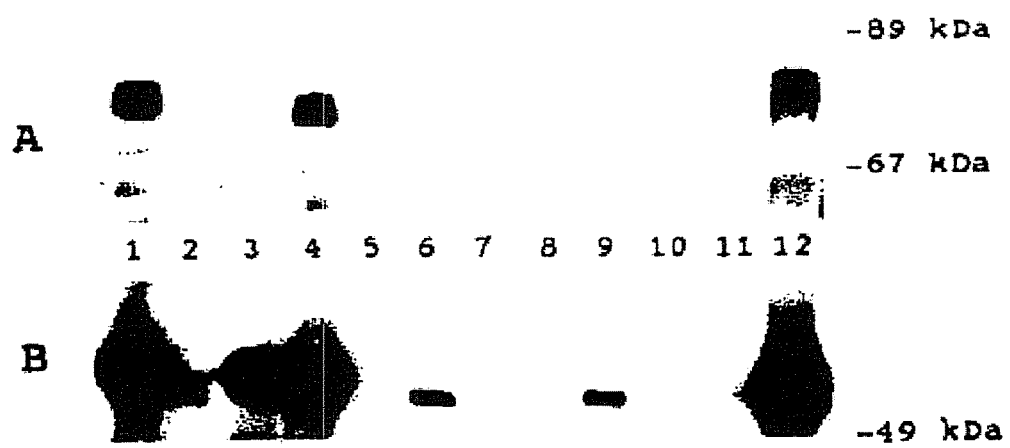
FIG. 10b: Detection of the endogenous SR-p70 protein.

FIG. 10b: Detection of the endogenous SR-p70 protein
  columns 1: COS-3; 2: CV-1; 3: HT-29; 4: U-373 MG; 5: MCF7; 6: SKNAS; 7: SK-N-MC; 8: IMR-32; 9: CHP212; 10: Saos-2; 11: SK-OV-3 and 12: SW480.

A: Visualization with the αSR-p70 antibody

B: Visualization with the αp53 antibody.

The αSR-p70 antibody specifically recognizes the recombinant proteins (FIG. 10a) and endogenous proteins (FIG. 10b) and does not cross with p53. The analysis of human or monkey cell lines shows the SR-p70 protein, like p53, is generally weakly detectable. In contrast, when an accumulation of p53 exists, SR-p70 becomes, for its part also, more readily detectable (FIG. 10b). A study by RT-PCR of the distribution of SR-p70 transcripts shows that the gene is expressed in all the cell types tested.

EXAMPLE VII

Cloning of the SR-p70 Gene and Chromosomal Localization

1) Cloning of SR-p70 Gene

The library used is a cosmid library prepared with purified human genomic DNA from placenta and marketed by Stratagene (reference 95 1202).

Screening of the gene is carried out as described in the EXAMPLE III.3, with an SR-p70 DNA fragment labelled with $^{32}$P with the BRL "Random Primers DNA Labelling Systems" kit (reference 18187-013). The hybridization and washing buffers are treated by adding 50% of formaldehyde. The last wash is carried out in 0.1×SSC/0.1% SDS at 60° C. In a similar manner, the SR-p70 gene was isolated from a library prepared with C57 black mouse genomic DNA.

An analysis and a partial sequencing of the clones demonstrate the presence of 14 exons with a structure close to that of the p53 gene, in particular in the central portion where the size and positioning of the exons are highly conserved (FIG. 12). This structure was partially defined in mouse and in man.

As an example, the human genomic sequences of the 3' region of intron 1, of exon 2, of intron 3 and of the 5' region of exon 3 are presented in FIG. 13.

2) Chromosomal Localization of the SR-p 70 Gene in Man

Figure 11:
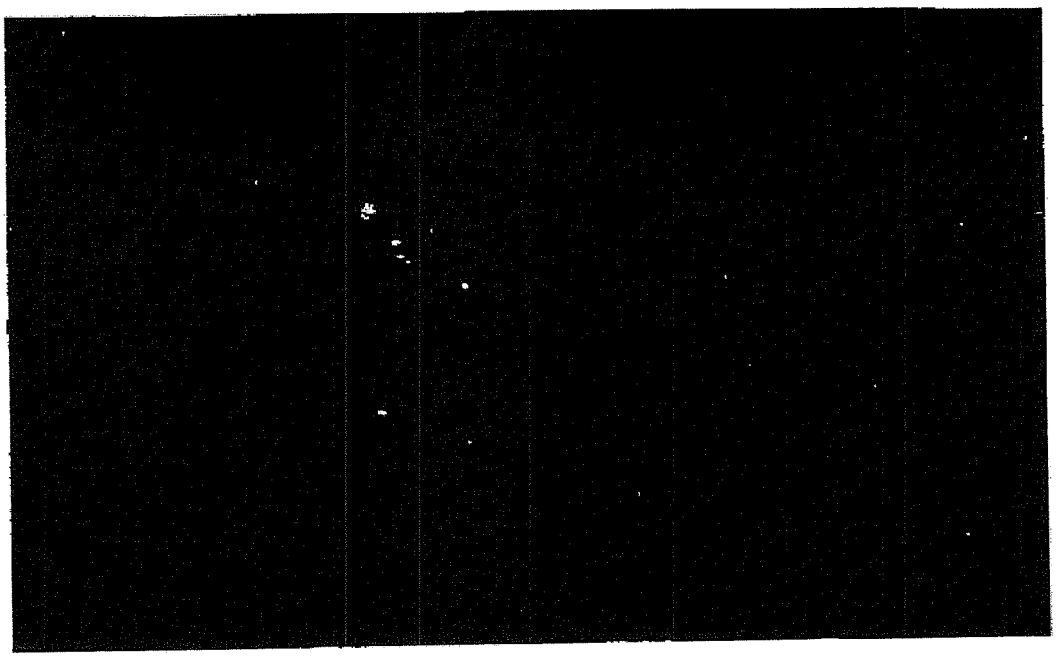
FIG. 11: Chromosomal localization of the human SR-p70 gene. The signal appears on chromosome 1, in the p36 region.

This was carried out with human SR-70 gene DNA using the technique described by R. Slim et al., Hum. Genet., 1991, 88, 21-26. Fifty mitoses were analysed, more than 80% of which had double spots localized at 1p36 on both chromosomes and more especially at 1p36.2-1p36.3 (FIG. 11). The identification of chromosome 1 and its orientation are based on the heterochromatin of the secondary constriction. The pictures were produced on a Zeiss Axiophot microscope, taken with a LHESA cooled CCD camera and treated with Optilab.

EXAMPLE VIII

A) Demonstration of an mRNA Coding for a Deduced Human SR-p70 Protein Possessing Both a Shorter N-Terminal End and a Divergence 1) Culturing of IMR-32 (Human Neuroblastoma) Cells The cells were cultured as described in the catalogue "Catalogue of cell lines and hybridomas, 7th edition, 1992" of the ATCC (American Type Culture Collection).

2) Preparation of the cDNA

The RNA is prepared as described in Example I.2.a. The cDNA is prepared in a manner similar to that described in Example I.3, with 5 µg total RNA in a final volume of 20 µl using a poly(T)$_{12}$ primer and with cold nucleotides. The reaction is not interrupted with EDTA.

3) Specific Amplification of SR-p 70 cDNA by the so-called PCR Technique

The polymerization is carried out with 2 µl of cDNA in 50 µl final with the buffer of the following composition: 50 mM Tris-HCl pH 9.2, 16 mM (NH$_4$)$_2$SO$_4$, 1.75 mM MgCl$_2$, in the presence of 10% DMSO, 0.4 mM NTP, 100 ng of each of the two nucleic acid primers and 3.5 units of the mixture of TAQ and PWO polymerases (Boehringer Mannheim, ref. 1681 842).

The primer pair is of the following composition:

```
sense primer:
                                         (SEQ ID No. 26)
AGGCCGGCGTGGGGAAG (position 16 to 32, FIG. 6)

antisense primer:
                                         (SEQ ID No. 27)
CTTGGCGATCTGGCAGTAG (position 503 to 485, FIG. 6).
```

The reaction is carried out for 30 cycles at 95° C./30 seconds, 58° C./1 minute and 68° C./2 minutes 30 seconds, followed by a final cycle of 68° C./10 minutes.

The PCR product is subjected to electrophoresis on a 1% agarose gel (TAE buffer). After ethidium bromide staining, two major bands are revealed: a band approximately 490 bp in size (expected size (see FIG. 6)) and an additional band approximately 700 bp in size. The latter is extracted from the gel using the "Geneclean" kit (Bio 101, ref 1001 400). After a desalting on a column of polyacrylamide P10 (Biorad, ref 15011050), the fragment is subjected to a further PCR amplification for 10 cycles as described above.

4) Determination of the Sequence of the Amplified Product

In a first step, the PCR product is removed from the oligonucleotides on a column of Sephacryl S-400 (Pharmacia 17-0609-01) and then desalted on a column of P10. The sequencing reaction is carried out using the Applied Biosystems kit (ref. 401 628) (373 DNA sequencer) with the antisense primer.

The sequence obtained is identical to the SR-p70 cDNA sequence (Example II.4) with an insertion of 198 bp between positions 217 and 218 (FIG. 14). The deduced N-terminal protein sequence (sequence designated SR-p70d) is 49 amino acids shorter, with a divergence of the first 13 amino acids (sequence ID No. 13). There is hence coexistence of at least two different SR-p70 transcripts as already described for the mouse AtT-20 line.

B) Cloning of Human SR-p70 and Demonstration of an mRNA Coding for a Deduced Human SR-p70 Protein Possessing the Same N-Terminal End as SR-p70d and a Divergence in the C-Terminal Portion 1) Specific Amplification of SR-p70 cDNA by the so-called PCR Technique The amplification was carried out as described in EXAMPLE VIII.A from purified RNA of IMR-32 cells with the primer pair of the following composition:

```
                                         (SEQ ID No. 28)
   sense primer:      GCG GCC ACG ACC GTG AC
   (position 160 to 176, sequence ID No. 11)

(SEQ ID No. 29)
   antisense primer:   GGC AGC TTG GGT CTC TGG
   (position 1993 to 1976, FIG. 6).
```

After removal of the excess primers on an S400 column and desalting on a P10 column, 1 µl of the sample is subjected again to a PCR with the primer pair of the following composition:

sense primer:
(SEQ ID No. 54)
TAT CTC GAG CTG TAC GTC GGT GAC CCC
XhoI (position 263 to 280, sequence ID No. 11)

antisense primer:
(SEQ ID No. 55)
ATA TCT AGA TCA GTG GAT CTC GGC CTC
XbaI (position 1943 to 1926, FIG. 6).

2) Cloning of the Amplified Product into Plasmid pCDNA3

The PCR product obtained in 1) is desalted on a P10 column, digested with the restriction enzymes XhoI and XbaI and then cloned into plasmid pCDNA3 as described in EXAMPLE II.5. Two recombinant clones are sequenced using the Applied Biosystems kit with the oligonu-cleotides specific for SR-p70 cDNA.

The first sequence obtained corresponds to the complete sequence of the mRNA coding for SR-p70 described in EXAMPLE VIII.a. The deduced protein contains 587 amino acids (sequence ID No. 13 and FIG. 16).

The second sequence obtained is identical to the SR-p70d cDNA sequence described above, but with two deletions, of 149 bp and of 94 bp between positions 1049 and 1050 on the one hand, and between positions 1188 and 1189 on the other hand (sequence ID No. 14 and FIG. 15). The protein sequence deduced from this second sequence reveals a protein having an N-terminal portion 49 amino acids shorter, with a divergence in the first 13 amino acids as well as a divergence of protein sequence between amino acids 350 and 397 (sequence ID No. 15 and FIG. 16) (sequence designated SR-p70e). The deduced protein contains 506 amino acids.

C) Demonstration of an mRNA Coding for a Deduced Human SR-p70 Protein Possessing a Shorter N-Terminal End 1) Culturing of SK-N-SH (Human Neuroblastoma) Cells The cells are cultivated as described in the "Catalogue of cell lines and hybridomas, 7th edition, 1992" of the ATCC (American Type Culture Collection).

2) Preparation of the cDNA and Amplification of SR-p70 cDNA by the so-called PCR Technique These steps are carried out as described in EXAMPLE VIII.A with the primer pair of the following composition:

(SEQ ID No. 32)
sense primer: AGG GGA CGC AGC GAA ACC
(position 128 to 145, FIG. 17)

(SEQ ID No. 29)
antisense primer:   GGC AGC TTG GGT CTC TGG
(position 1993 to 1976, FIG. 6).

The sequencing is carried out with the Applied Biosystem kit with primers specific for SR-p70 cDNA, and reveals two cDNAs:

a first cDNA corresponding to the mRNA coding for SR-p70a a second cDNA having a deletion of 98 bp between positions 24 and 25 (sequence ID No. 16 and FIG. 15).

This deletion comprises the translation initiation ATG of SR-p70a. The protein deduced (designated SR-p70f) from this second cDNA possesses a translation initiation ATG downstream corresponding to an internal ATG of SR-p70a. The deduced protein hence contains 588 amino acids (sequence ID No. 17 and FIG. 16) and is truncated with respect to the 48 N-terminal amino acids of SR-p70a.

D) Demonstration of an mRNA Coding for Human SR-p70b

1) Culturing of K562 Cells

The cells are cultured as described in the "Catalogue of cell lines and hybridomas, 7th edition, 1992" of ATCC (American Type Culture Collection).

2) Preparation of the cDNA, Amplification of SR-p70 cDNA by the so-called PCR Technique and Sequencing These steps are carried out as described in EXAMPLE VIII.C.

The sequencing reveals two cDNAs:

A first cDNA corresponding to the mRNA coding for SR-p70a, and a second cDNA having a deletion of 94 bp between positions 1516 and 1517 (sequence ID No. 18 and FIG. 15). The deduced protein (designated SR-p70b) contains 199 amino acids and possesses a C-terminal sequence truncated by 137 amino acids relative to SR-p70a, with the last 4 amino acids divergent (sequence ID No. 19 and FIG. 21).

This cDNA is similar to the one described in EXAMPLE I relating to monkey SR-p70b.

The molecules described in this example (EXAMPLE VIII.A, B, C and D) reveal SR-p70 variants which are the outcome of differential splicings of the primary mRNA, transcribed by the SR-p70 gene.

The SR-p70a is encoded by an mRNA composed of 14 exons (see EXAMPLE VII). This is the reference protein. SR-p70b is the outcome of an insertion between exons 3 and 4 and of the absence of exons 11 and 13. SR-p70f is the outcome of the absence of exon 2. This example describes the existence of SR-p70 variants non-exhaustively, with a strong probability of existence of other variants. Similarly, the existence of these variants described in this example, as well as SR-p70a, is not limited to the lines in which they have been demonstrated. In effect, studies performed by RT-PCR showed that these variants are to be found in the various lines studied.

Furthermore, the initiation methionine of SR-p70f corresponds to an internal methionine of SR-p70a, suggesting the possibility of initiation downstream on the mRNA coding for SR-p70a.

EXAMPLE IX

Obtaining a 5' Sequence of Human SR-p70a mRNA

1) Amplification of the 5' End of SR-p70 cDNA by PCR

The cell culturing and the preparations of total RNA and of cDNA are carried out as described in EXAMPLE VIII.1 and 2. The RNA template is hydrolysed by incubation for 5 minutes at 65° C. after the addition of 4'µl of 500 mM EDTA and 4 µl of 2 N NaOH. The sample is then desalted on a P10 column. The cDNA is elongated at the 3' end with a dG tail as described in EXAMPLE 1.3.d, in a final volume of 40 µl. After the addition of 4 µl of 500 mM EDTA and 4 µl of 2 N NaOH, the cDNA is incubated at 65° C. for 3 minutes and then desalted on a P10 column. PCR amplification is carried out as described in EXAMPLE VIII.3 with 8 µl of cDNA and for 30 cycles with the primer pair of the following composition:

```
sense primer:           CCCCCCCCCCCCCCN    (SEQ ID No. 41)
(where N equals G, A or T)

antisense primer:       CCATCAGCTCCAGGCTCTC  (SEQ ID No. 33)
(position 1167 to 1149, FIG. 6).
```

After removal of the excess primers on an S-400 column and desalting on a P10 column, 1 µl of the sample is subjected again to a PCR with the pair of the following composition:

```
sense primer:           CCCCCCCCCCCCCCN    (SEQ ID No. 41)

antisense primer:       CCAGGACAGGCGCAGATG  (SEQ ID No. 34)
(position 928 to 911, FIG. 6).
```

The sample, passed again through an S-400 column and a P10 column, is subjected to a third amplification for 20 cycles with the following pair:

```
sense primer:           CCCCCCCCCCCCCCN antisense primer:       CTTGGCGATCTGGCAGTAG
(position 503 to 485, FIG. 6).
```

2) Determination of the SR-p70 cDNA 5' Sequence

The sequence is produced as described in EXAMPLE VIII.4. This sequence reveals a non-coding 5' region of at least 237 bases upstream of the initiation ATG of SR-p70a (FIG. 17). By comparison of this sequence (obtained from the line IMR-32) with the one obtained from the line HT-29 in particular (FIG. 6), two point differences (FIG. 17: see bold characters) are revealed (G→A and C→T), positioned, respectively, at −20 and −30 from the initiation ATG of SR-p70a (FIGS. 6 and 17). This variability is located in exon 2 (FIG. 13). It is not ruled out that this variability is also to be found within a coding frame as the outcome of an alternative splicing as described in EXAMPLES III in mouse and VIII in man, or alternatively as the outcome of a translation initiation on a CTG (as has been demonstrated for FGFb (Proc. Natl. Acad. Sci. USA, 1989, 86, 1836-1840)).

Similarly, it is not ruled out that this variability has a repercussion on the translation of SR-p70 or on the splicing of the primary RNA.

At all events, this variability, probably of allelic origin, may serve as a marker, either at genomic level (see EXAMPLE XI) or at mRNA level (see EXAMPLE X).

EXAMPLE X

1) Analysis by PCR of the Transcriptional Expression of SR-p70a in Cell Samples (RT-PCR)

Cell culturing (SK-N-AS, SK-N-MC, HT-29, U-373MG, SW480, IMR-32, CHP212) is carried out as described in Example VI.1.a (referred to the catalogue "Catalogue of cell lines and hybridomas, 7th edition 1992" of the ATCC).

The preparation of the cDNA and the PCR amplification are carried out as described in EXAMPLE VIII.2 and 3. The primer pair used is of the following composition:

```
sense primer:           AGGGGACGCAGCGAAACC  (SEQ ID No. 32)
(position 128 to 145, FIG. 17)

antisense primer:       GGCAGCTTGGGTCTCTGG  (SEQ ID No. 29)
(position 1993 to 1976, FIG. 6).
```

Figure 18:
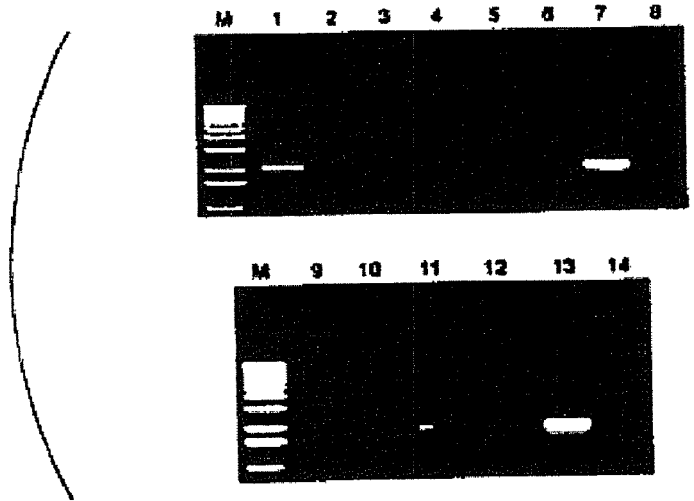
FIG. 18: Analysis of the SR-p70a transcripts after PCR amplification.
- lane M: 1 kb ladder (GIBCO-BRL) molecular weight markers
- lane 1: line HT29
- lane 3: line SK-N-AS
- lane 5: line UMR-32
- lane 7: line U-373 MG
- lane 9: line SW 480
- lane 11: line CHP 212
- lane 13: line SK-N-MC
- lanes 2, 4, 6, 8, 10, 12, 14: negative controls corresponding to lanes 1, 3, 5, 7, 9, 11 and 13, respectively (absence of inverse transcriptase in the RT-PCR reaction).

The samples are analysed by electrophoresis on a 1% agarose gel and visualization with ethidium bromide (FIG. 18).

The size of the band obtained in the samples corresponds to the expected size (approximately 2 kb, FIGS. 6 and 17). The intensity of the bands obtained is reproducible. A reamplification of 1 µl of the sample under the same conditions for 20 cycles reveals a band in each of the samples.

2) Determination of the Sequence of the Amplified Products

After passage of the samples through S-400 and P 10 columns, sequencing is carried out on an Applied Biosystems sequencer 373 with the reference kit 401 628. The primers used are, inter alia, the following:

|  | position | FIG. |
|---|---|---|
| AGGGGACGCAGCGAAACC (SEQ ID No. 32) | 128 to 145 | 22 |
| CTTGGCGATCTGGCAGTAG (SEQ ID No. 27) | 593 to 485 | 6 |
| GATGAGGTGGCTGGCTGGA (SEQ ID No. 35) | 677 to 659 | 6 |
| CCATCAGCTCCAGGCTCTC (SEQ ID No. 33) | 1167 to 1149 | 6 |
| TGGTCAGGTTCTGCAGGTG (SEQ ID No. 36) | 1605 to 1587 | 6 |
| GGCAGCTTGGGTCTCTGG (SEQ ID No. 29) | 1993 to 1976 | 6 |

No protein difference in the SR-p70a was detected. However, sequences obtained reveal a double variability at positions −20 and −30 upstream of the initiation ATG of SR-p70a (FIGS. 6 and 17). This variability, probably of allelic origin, enables two classes of transcripts to be defined: a first class possessing a G at position −30 and a C at position −20 (class $G^{-30}/C^{-20}$) and a second class possessing a difference at two positions: an A at −30 and a T at −20 (class $A^{-30}/T^{-20}$).

First class: SK-N-AS, SK-N-MC, HT-29, U-373MG, SW480.

Second class: IMR-32, CHP212.

EXAMPLE XI

Analytical Method of Determination of the Allelic Distribution of the SR-p70 Gene in a Population of 10 Persons This allelic distribution is based on the allelic variability demonstrated in EXAMPLES IX and X:

$G^{-30}/C^{-20}$ allele possessing, respectively, a G and a C at positions −30 and −20 upstream of the initiation ATG of SR-p70a.

A⁻³⁰/T⁻²⁰ allele possessing, respectively, an A and a T at the same positions.

This variability may be demonstrated by the use of restriction enzymes that differentiate the two alleles (FIG. 13). As an example:

Enzyme BplI having a cleavage site only on the $G^{-30}/C^{-20}$ allele in the zone of interest (this site encompasses both variable positions).

Enzyme StyI having a cleavage site only on the $A^{-30}/T^{-20}$ allele in the zone of interest.

1) Genomic Amplification of Exon 2 by PCR

The polymerization reaction is carried out with 500 ng of purified genomic DNA, in 50 µl final with the conditions described in Example VIII.3.

The primer pair is of the following position:

```
                                       (SEQ ID No. 37)
Sense primer:         CACCTACTCCAGGGATGC
(position 1 to 18, FIG. 13)

(SEQ ID No. 38)
Antisense primer:     AGGAAAATAGAAGCGTCAGTC
(position 833 to 813, FIG. 13).
```

After removal of the excess primer on an S-400 column and desalting on a P10 column, 1 µl of the sample is amplified again for 25 cycles under the same conditions with the following primer pair:

```
                                       (SEQ ID No. 39)
Sense primer:         CAGGCCCACTTGCCTGCC
(position 25 to 32, FIG. 13)

(SEQ ID No. 40)
Antisense primer:     CTGTCCCCAAGCTGATGAG
(position 506 to 488, FIG. 13).
```

Figure 19A:
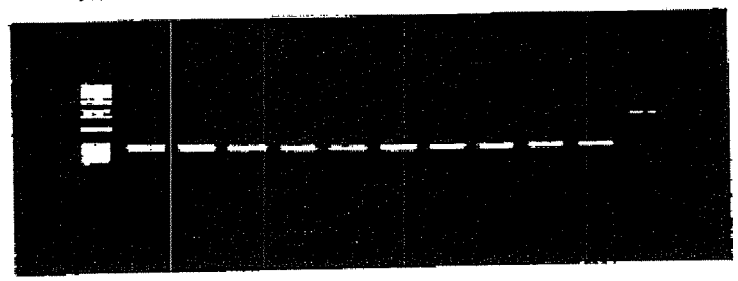
FIGS. 19A and 19B: A: Analysis by agarose gel electrophoresis of genomic fragments amplified by PCR (from the 3' end of intron 1 to the 5' end of exon 3). The numbering of the lanes corresponds to the numbering of the control population. Lane M: molecular weight markers (1 kb ladder).
- B: Analysis identical to that of part A, after digestion of the same samples with the restriction enzyme StyI.
Figure 19B:
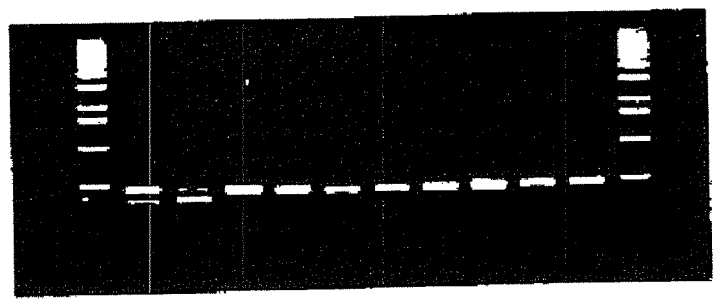
Figure 20:
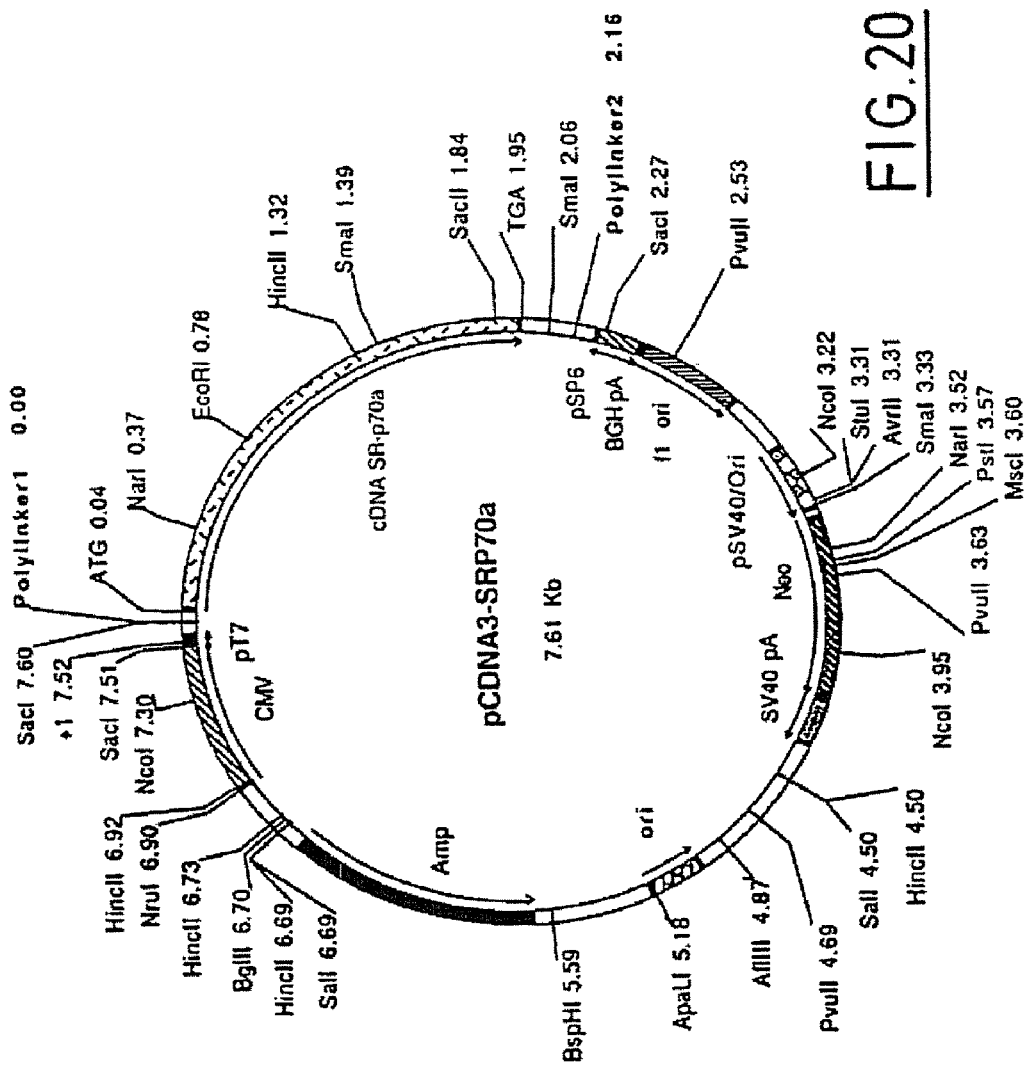

The amplified products are subjected to electrophoresis on a 1% agarose gel (FIG. 19-A).

2) Digestion with the Restriction Enzyme StyI

The samples are desalted beforehand on a P10 column and then digested with the restriction enzyme StyI (BRL 15442-015) in the buffer of the following composition: 50 mM Tris-HCl pH 8, 100 mM NaCl, 10 mM $MgCl_2$, at 37° C. for 30 min. The digestion products are analysed by electrophoresis on a 1% agarose gel (TAE buffer). Visualization is carried out by ethidium bromide staining (FIG. 19-B).

A band of 482 base pairs characterizes the $G^{-30}/C^{-20}$ allele (FIGS. 13 and 19). The presence of a band of 376 base pairs and a band of 106 base pairs characterize the $A^{-20}/T^{-20}$ allele (allele possessing a StyI cleavage site).

On the population of 10 persons, 2 persons exhibit the $G^{-30}/C^{-20}$ and $A^{-30}/T^{-20}$ alleles, the other 8 persons being homozygous with the $G^{-30}/C^{-20}$ allele. The study of a fresh population of 9 persons demonstrated 3 heterozygous persons exhibiting the $G^{-30}/C^{-20}$ and $A^{-30}/T^{-20}$ alleles, the other 6 persons being homozygous for the $G^{-30}/C^{-20}$ allele.

EXAMPLE XII

Test of Reversion of Transformation of the Line SK-N-AS by Transfection with SR-p70 cDNA The expression vector used is described in EXAMPLE II.5 and shown diagrammatically in FIG. 15. The method used is the so-called calcium phosphate method described by Graham et al. (Virology 1973, 54, 2, 536-539). The line is inoculated in the proportion of 5×10⁵ cells per dish 6 cm in diameter in 5 ml of the medium described in Example I.1. The cells are cultured at 37° C. and with 5% $CO_2$ overnight. The transfection medium is prepared in the following manner: the following mixture is prepared by adding, in order, 1 ml of HEBS buffer (8 mg/ml NaCl, 370 µg/ml KCl, 125 µg/ml $Na_2HPO_4.2H_2O$, 1 mg/ml dextrose, 5 mg/ml Hepes pH 7.05), 10 µg of the plasmid to be transfected and 50 µl of 2.5 M $CaCl_2$ added dropwise. The transfection medium is left for 30 min at room temperature and then added dropwise to the medium contained in the culture dish. The cells are incubated for 5 to 6 hours at 37° C./5% $CO_2$. After the medium is aspirated off, 5 ml of fresh medium containing 2% of foetal bovine serum are added. After 48 hours at 37° C./5% $CO_2$, the cells are rinsed with PBS, detached by trypsinization, diluted in 10 ml of culture medium (5% foetal bovine serum) and plated out in a dish 10 cm in diameter (the dilution may be adjusted in accordance with the efficiency of transfection). After a further incubation for 10 hours (the time for the cells to adhere), the cells are subjected to selection by adding G418 at a final concentration of 600 µg/ml Geneticin equivalent for 15 to 21 days (the medium is changed every day). The clones obtained are then rinsed with PBS, fixed in 70% ethanol, dried, stained with 1% crystal violet and then counted.

Four plasmid transfections were carried out in duplicate:
plasmid pcDNA3 without insert
plasmid pcDNA3/SR-p70 containing human SR-p70a cDNA
plasmid pcDNA3/SR-p70 Mut containing SR-p70a cDNA possessing a mutation at position 293 AA (R→E) which is analogous to the mutation 273 (R→H) in the DNA-binding domain of p53
control without plasmid.

The result is expressed as the number of clones per dish.

|  | Experiment 1 | Experiment 2 | Mean |
|---|---|---|---|
| pCDNA3 | 172 | 353 | 262 |
| pCDNA3/SR-p70 | 13 | 8 | 10 |
| pCDNA3/SR-p70 Mut | 92 | 87 | 89 |
| Absence of plasmid | 1 | 3 | 2 |

The number of clones obtained by transfection with plasmid pcDNA3/SR-p70 is 25-fold less than the number of clones obtained with the control pcDNA3 and 9-fold less than the number of clones obtained with pcDNA3/SR-p70 Mut, indicating a mortality or an arrest of cell division of the cells transfected with SR-p70 cDNA. This result is not the consequence of a toxicity in view of the clones obtained with the mutated SR-p70 cDNA, but probably of an apoptosis as has been demonstrated for the p53 protein (Koshland et al., Sciences, 1993, 262, 1953-1981).

EXAMPLE XIII

Biological Role of the SR-p70 Protein

The structural homology between the DNA-binding domain of p53 and the central region of the SR-p70 protein enables it to be inferred that SR-p70 is a transcription factor (see FIGS. 1 and 2). In effect, p53 (393 amino acids) consists of several functional domains. The N-terminal region (1-91 amino acids) is involved in the activation of transcription, and contains sites for interaction with different cellular and viral proteins. The central portion (amino acids 92 to 292) permits binding to the specific DNA sequences located in the promoter regions of certain genes (the majority of point mutations that inactivate p53 are localized in this region), and also possesses numerous sites for interaction with viral proteins which inhibit its activity. Finally, the last 100 amino acids of p53 are responsible for its oligomerization as well as for the regulation of the latter (Hainaut P., Current Opinion in Oncology, 1995, 7, 76-82; Prokocimer M., Blood, 1994, 84 No. 8, 2391-2411).

The sequence homology between p53 and SR-p70 is significant, in particular as regards the amino acids involved directly in the interaction with DNA, suggesting that SR-p70 binds to the p53 sites on DNA. These amino acids correspond very exactly to what are referred to as the "hot spots", amino acids frequently mutated in human tumours (SWISS PROT: SW: P53_human and Prokocimer M., Blood, 1994, 84 No. 8, 2391-2411). From this homology, it may be deduced that the SR-p70 protein exerts a control over the activity of the genes regulated by p53, either independently of the latter or by forming heterooligomers with it.

Consequently, like p53, the products of the SR-p70 gene must be involved in the control and regulation of the cell cycle, causing the cycle to stop (momentarily or permanently), and the implementation of programmes such as DNA repair, differentiation or cell death. The likelihood of the existence of "p53-like" activities had been strongly felt with the demonstration in p53$^{-/-}$ mice of activities of DNA repair and cell death in response to ionizing radiations (Strasser et al., Cell, 1994, 79, 329-339). The authors of the present invention have localized the human SR-p70 gene in the telomeric region of the short arm of chromosome 1, precisely at 1p36.2-36.3, the smallest deleted region (SRO) common to a majority of neuroblastomas and of other types of tumours (melanomas and sarcomas) (White et al., PNAS, 1995, 92, 5520-5524). This region of loss of heterozygosity (LOH) defines the locus of a tumour-suppressing gene whose loss of activity is considered to be the cause of tumour formation. It is important to recall that this region is also subject to "maternal imprinting"; the maternal allele is preferentially lost in neuroblastomas having the 1p36 deletion (without amplification of N-Myc) (Caron et al., Hum. Mol. Gen., 1995, 4, 535-539). The wide-type SR-p70 gene introduced into neuroblastoma cells and expressed therein permits the reversion of their transformation. The loss of this anti-oncogenic activity is hence associated with the development of the tumour. The 1p36 region possesses a syngeneic homology with the distal segment of the mouse chromosome 4. In this region, the curly tail (ct) gene (Beier et al., Mammalian Genome, 1995, 6, 269-272) involved in congenital malformations of the neural tube (NTM: spina bifida, anencephaly, etc). The ct mouse is the best animal model for studying these malformations. It is accepted that these malformations result from abnormalities of cell proliferation. Bearing in mind the nature of the SR-p70 gene and its chromosomal localization, one of the hypotheses is that SR-p70 could be the human homologue of ct and that, on this basis, the detection of early mutations and chromosomal abnormalities affecting this gene should permit, for example, as an application, the identification of persons at risk (0.5-1% of newborn babies affected by NTM) and the implementation of preventive treatments (Neumann et al., Nature Genetics, 1994, 6, 357-362; Di Vinci et al., Int. J. Cancer, 1994, 59, 422-426; Moll et al., PNAS, 1995, 92, 4407-4411; Chen et al., Development, 1995, 121, 681-691).

EXAMPLE XIV

Allelic Study of the SR-p70 Gene

The GC and AT alleles are readily identified by StyI restriction of the PCR products of exon 2 (see Example XI). Hence it was possible to determine in this way, in GC/AT heterozygous individuals bearing neuroblastoma tumours, the lost SR-p70 allele (GC or AT), in spite of the presence of contaminating healthy tissue.

Surprisingly, when the same analysis is carried out on the RNA, a single allele is demonstrated independently of the presence or otherwise of a deletion and, still more surprisingly, in spite of the presence of healthy tissue. This suggests that the imprint (differential expression of the two alleles) would also exist in the contaminating tissue.

In order to verify this, the same analysis was repeated on the RNA originating from blood cells of healthy GC/AT heterozygous individuals. Only one of the two types of transcript was detected also in these cells. This result confirms the observation made on the tumour samples regarding the existence of a generalized genetic imprint for the SR-p70 gene.

The implications of this discovery are important, since it enables it to be postulated that a single sporadic mutation inactivating the active SR-p70 allele will give rise to a loss of activity, this potentially occurring in all the tissues.

The absence of precise data on the biological function of SR-p70 does not enable the consequences of this loss of SR-p70 activity for the cell to be measured. Nevertheless, its strong homology with the p53 tumour-suppressing protein, as well as the demonstration that SR-p70 is a transcription factor capable of utilizing the P21$^{waf}$ promoter, suggests a role of this protein in the control of the cell cycle and in differentiation.

Knudson and Meadows, 1980 (New Eng. J. Med. 302: 1254-56), consider the IV-S neuroblastomas to be a collection of non-malignant cells from the neural crest carrying a mutation which interferes with their normal differentiation.

It is conceivable that the loss of SR-p70 activity, like the loss of p53 control over the cell cycle, favours the appearance of cellular abnormalities such as aneuploidy, amplification (described in the case of neuroblastomas) and other genetic reorganizations capable of causing cell transformation (Livingstone et al., 1992, Cell 71:923-25; Yin et al. 1992, Cell 72:937-48; Cross et al. 1995, Science 267:1353-56; Fukasawa et al. 1996, Science 271:1744-47). Neuroblastomas might hence arise originally from a temporary or permanent loss of activity of SR-p70, thereby favouring the occurrence of oncogenic events and hence tumour progression.

In the case of the 1p36 constitutional deletion described by Biegel et al., 1993 (Am. J. Hum. Genet. 52:176-82), IV-S neuroblastoma does indeed occur and the gene affected is NBS-1 (SR-p70).

In conclusion, what is described for neuroblastomas might also apply to other types of tumours, in particular those associated with reorganization of the end of the short arm of chromosome 1 (Report 2 international workshop on human chr 1 mapping 1995, Cytogenetics and Cell Genet. 72:113-154). From a therapeutic standpoint, the involvement of SR-p70 in the occurrence of tumours should lead to the avoidance of the use of mutagenic agents in chemotherapy, bearing in mind the risks of cell transformation by these products, and to the use, in preference to these products, of non-mutagenic substances which stimulate differentiation.

Moreover, the frequency of occurrence of the GC and AT alleles is as follows: in the population, Frequency(AT)=0.15, and on a sample of 25 (neuroblastoma) patients, F(AT)=0.30. These statistics indicate that the AT allele could be a predisposing factor.

SEQUENCE LISTING

<160> NUMBER OF SEQ ID NOS: 55

<210> SEQ ID NO 1
<211> LENGTH: 2874
<212> TYPE: DNA
<213> ORGANISM: Cebus apella
<220> FEATURE:
<221> NAME/KEY: CDS
<222> LOCATION: (156)..(2066)

<400> SEQUENCE: 1

```
tgcctccccg cccgcgcacc cgccccgagg cctgtgctcc tgcgaagggg acgcagcgaa      60
gccggggccc gcgccaggcc ggccgggacg gacgccgatg cccggagctg cgacggctgc     120
agagcgagct gccctcggag gccggtgtga ggaag atg gcc cag tcc acc acc        173
                                      Met Ala Gln Ser Thr Thr
                                        1               5 acc tcc ccc gat ggg ggc acc acg ttt gag cac ctc tgg agc tct ctg       221
Thr Ser Pro Asp Gly Gly Thr Thr Phe Glu His Leu Trp Ser Ser Leu
                10                  15                  20 gaa cca gac agc acc tac ttc gac ctt ccc cag tca agc cgg ggg aat       269
Glu Pro Asp Ser Thr Tyr Phe Asp Leu Pro Gln Ser Ser Arg Gly Asn
             25                  30                  35 aat gag gtg gtg ggt ggc acg gat tcc agc atg gac gtc ttc cac cta       317
Asn Glu Val Val Gly Gly Thr Asp Ser Ser Met Asp Val Phe His Leu
         40                  45                  50 gag ggc atg acc aca tct gtc atg gcc cag ttc aat ttg ctg agc agc       365
Glu Gly Met Thr Thr Ser Val Met Ala Gln Phe Asn Leu Leu Ser Ser
 55                  60                  65                  70 acc atg gac cag atg agc agc cgc gct gcc tcg gcc agc ccg tac acc       413
Thr Met Asp Gln Met Ser Ser Arg Ala Ala Ser Ala Ser Pro Tyr Thr
                 75                  80                  85 ccg gag cac gcc gcc agc gtg ccc acc cat tca ccc tac gca cag ccc       461
Pro Glu His Ala Ala Ser Val Pro Thr His Ser Pro Tyr Ala Gln Pro
             90                  95                 100 agc tcc acc ttc gac acc atg tcg ccc gcg cct gtc atc ccc tcc aac       509
Ser Ser Thr Phe Asp Thr Met Ser Pro Ala Pro Val Ile Pro Ser Asn
        105                 110                 115 acc gac tat ccc gga ccc cac cac ttc gag gtc act ttc cag cag tcc       557
Thr Asp Tyr Pro Gly Pro His His Phe Glu Val Thr Phe Gln Gln Ser
    120                 125                 130 agc acg gcc aag tca gcc acc tgg acg tac tcc cca ctc ttg aag aaa       605
Ser Thr Ala Lys Ser Ala Thr Trp Thr Tyr Ser Pro Leu Leu Lys Lys
135                 140                 145                 150 ctc tac tgc cag atc gcc aag aca tgc ccc atc cag atc aag gtg tcc       653
Leu Tyr Cys Gln Ile Ala Lys Thr Cys Pro Ile Gln Ile Lys Val Ser
                155                 160                 165 gcc cca ccg ccc ccg ggc acc gcc atc cgg gcc atg cct gtc tac aag       701
Ala Pro Pro Pro Pro Gly Thr Ala Ile Arg Ala Met Pro Val Tyr Lys
            170                 175                 180 aag gcg gag cac gtg acc gac atc gtg aag cgc tgc ccc aac cac gag       749
Lys Ala Glu His Val Thr Asp Ile Val Lys Arg Cys Pro Asn His Glu
        185                 190                 195 ctc ggg agg gac ttc aac gaa gga cag tct gcc cca gcc agc cac ctc       797
Leu Gly Arg Asp Phe Asn Glu Gly Gln Ser Ala Pro Ala Ser His Leu
    200                 205                 210 atc cgt gtg gaa ggc aat aat ctc tcg cag tat gtg gac gac cct gtc       845
Ile Arg Val Glu Gly Asn Asn Leu Ser Gln Tyr Val Asp Asp Pro Val
215                 220                 225                 230
```

|  |  |
|---|---|
| acc ggc agg cag agc gtc gtg gtg ccc tat gag cca cca cag gtg ggg<br>Thr Gly Arg Gln Ser Val Val Val Pro Tyr Glu Pro Pro Gln Val Gly<br>235 240 245 | 893 |
| aca gaa ttc acc acc atc ctg tac aac ttc atg tgt aac agc agc tgt<br>Thr Glu Phe Thr Thr Ile Leu Tyr Asn Phe Met Cys Asn Ser Ser Cys<br>250 255 260 | 941 |
| gtg ggg ggc atg aac cga cgg ccc atc ctc atc atc atc acc ctg gag<br>Val Gly Gly Met Asn Arg Arg Pro Ile Leu Ile Ile Ile Thr Leu Glu<br>265 270 275 | 989 |
| acg cgg gat ggg cag gtg ctg ggc cgc cgg tcc ttc gag ggc cgc atc<br>Thr Arg Asp Gly Gln Val Leu Gly Arg Arg Ser Phe Glu Gly Arg Ile<br>280 285 290 | 1037 |
| tgc gcc tgt cct ggc cgc gac cga aaa gcc gat gag gac cac tac cgg<br>Cys Ala Cys Pro Gly Arg Asp Arg Lys Ala Asp Glu Asp His Tyr Arg<br>295 300 305 310 | 1085 |
| gag cag cag gcc ttg aat gag agc tcc gcc aag aac ggg gct gcc agc<br>Glu Gln Gln Ala Leu Asn Glu Ser Ser Ala Lys Asn Gly Ala Ala Ser<br>315 320 325 | 1133 |
| aag cgc gcc ttc aag cag agt ccc cct gcc gtc ccc gcc ctg ggc ccg<br>Lys Arg Ala Phe Lys Gln Ser Pro Pro Ala Val Pro Ala Leu Gly Pro<br>330 335 340 | 1181 |
| ggt gtg aag aag cgg cgg cac gga gac gag gac acg tac tac ctg cag<br>Gly Val Lys Lys Arg Arg His Gly Asp Glu Asp Thr Tyr Tyr Leu Gln<br>345 350 355 | 1229 |
| gtg cga ggc cgc gag aac ttc gag atc ctg atg aag ctg aag gag agc<br>Val Arg Gly Arg Glu Asn Phe Glu Ile Leu Met Lys Leu Lys Glu Ser<br>360 365 370 | 1277 |
| ctg gag ctg atg gag ttg gtg ccg cag ccg ctg gta gac tcc tat cgg<br>Leu Glu Leu Met Glu Leu Val Pro Gln Pro Leu Val Asp Ser Tyr Arg<br>375 380 385 390 | 1325 |
| cag cag cag cag ctc cta cag agg ccg agt cac cta cag ccc cca tcc<br>Gln Gln Gln Gln Leu Leu Gln Arg Pro Ser His Leu Gln Pro Pro Ser<br>395 400 405 | 1373 |
| tac ggg ccg gtc ctc tcg ccc atg aac aag gtg cac ggg ggc gtg aac<br>Tyr Gly Pro Val Leu Ser Pro Met Asn Lys Val His Gly Gly Val Asn<br>410 415 420 | 1421 |
| aag ctg ccc tcc gtc aac cag ctg gtg ggc cag cct ccc ccg cac agc<br>Lys Leu Pro Ser Val Asn Gln Leu Val Gly Gln Pro Pro Pro His Ser<br>425 430 435 | 1469 |
| tcg gca gct aca ccc aac ctg gga cct gtg ggc tct ggg atg ctc aac<br>Ser Ala Ala Thr Pro Asn Leu Gly Pro Val Gly Ser Gly Met Leu Asn<br>440 445 450 | 1517 |
| aac cac ggc cac gca gtg cca gcc aac agc gag atg acc agc agc cac<br>Asn His Gly His Ala Val Pro Ala Asn Ser Glu Met Thr Ser Ser His<br>455 460 465 470 | 1565 |
| ggc acc cag tcc atg gtc tcg ggg tcc cac tgc act ccg cca ccc ccc<br>Gly Thr Gln Ser Met Val Ser Gly Ser His Cys Thr Pro Pro Pro Pro<br>475 480 485 | 1613 |
| tac cac gcc gac ccc agc ctc gtc agt ttt tta aca gga ttg ggg tgt<br>Tyr His Ala Asp Pro Ser Leu Val Ser Phe Leu Thr Gly Leu Gly Cys<br>490 495 500 | 1661 |
| cca aac tgc atc gag tat ttc acg tcc cag ggg tta cag agc att tac<br>Pro Asn Cys Ile Glu Tyr Phe Thr Ser Gln Gly Leu Gln Ser Ile Tyr<br>505 510 515 | 1709 |
| cac ctg cag aac ctg acc atc gag gac ctg ggg gcc ctg aag atc ccc<br>His Leu Gln Asn Leu Thr Ile Glu Asp Leu Gly Ala Leu Lys Ile Pro<br>520 525 530 | 1757 |
| gag cag tat cgc atg acc atc tgg cgg ggc ctg cag gac ctg aag cag<br>Glu Gln Tyr Arg Met Thr Ile Trp Arg Gly Leu Gln Asp Leu Lys Gln<br>535 540 545 550 | 1805 |

```
ggc cac gac tac ggc gcc gcc gcg cag cag ctg ctc cgc tcc agc aac      1853
Gly His Asp Tyr Gly Ala Ala Ala Gln Gln Leu Leu Arg Ser Ser Asn
                555                 560                 565 gcg gcc gcc att tcc atc ggc ggc tcc ggg gag ctg cag cgc cag cgg      1901
Ala Ala Ala Ile Ser Ile Gly Gly Ser Gly Glu Leu Gln Arg Gln Arg
            570                 575                 580 gtc atg gag gcc gtg cac ttc cgc gtg cgc cac acc atc acc atc ccc      1949
Val Met Glu Ala Val His Phe Arg Val Arg His Thr Ile Thr Ile Pro
        585                 590                 595 aac cgc ggc ggc ccc ggc gcc ggc ccc gac gag tgg gcg gac ttc ggc      1997
Asn Arg Gly Gly Pro Gly Ala Gly Pro Asp Glu Trp Ala Asp Phe Gly
    600                 605                 610 ttc gac ctg ccc gac tgc aag gcc cgc aag cag ccc atc aag gag gag      2045
Phe Asp Leu Pro Asp Cys Lys Ala Arg Lys Gln Pro Ile Lys Glu Glu
615                 620                 625                 630 ttc acg gag gcc gag atc cac tgaggggccg ggcccagcca gagcctgtgc         2096
Phe Thr Glu Ala Glu Ile His
                635 caccgcccag agaccaggcc cgcctcgctc tccttcctgt gtccaaaact gcctccggag    2156 gcagggcctc caggctgtgc ccggggaaag gcaaggtccg gcccatgccc cggcacctca    2216 ccggccccag gagaggccca gccaccaaag ccgcctgcgg acagcctgag tcacctgcag    2276 aaccttctgg agctgcccta tgctgggct tgcggggcag gggccggccc actctcagcc     2336 ctgccactgc cgggcgtgct ccatggcagg cgtgggtggg gaccgcagtg tcagctccga    2396 cctccaggcc tcatcctaga gactctgtca tctgccgatc aagcaaggtc cttccagagg    2456 aaagaatcct cttcgctggt ggactgccaa aaagtatttt gcgacatctt ttggttctgg    2516 agagtggtga gcagccaagc gactgtgtct gaaacaccgt gcattttcag ggaatgtccc    2576 taacgggctg gggactctct ctgctggact tgggagtggc ctttgccccc agcacactgt    2636 attctgcggg accgcctcct tcctgcccct aacaaccacc aaagtgttgc tgaaattgga    2696 gaaaactggg gaaggcgcaa cccctcccag gtgcgggaag catctggtac cgcctcggcc    2756 agtgcccctc agcctgggca cagtcacctc tccttgggga accctgggca gaaagggaca    2816 gcctgtcctt agaggaccgg aaattgtcaa tatttgataa aatgataccc ttttctac     2874

<210> SEQ ID NO 2
<211> LENGTH: 637
<212> TYPE: PRT
<213> ORGANISM: Cebus apella

<400> SEQUENCE: 2

Met Ala Gln Ser Thr Thr Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110
```

```
Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Ala Pro Pro Pro Gly Thr Ala Ile Arg
                165                 170                 175

Ala Met Pro Val Tyr Lys Lys Ala Glu His Val Thr Asp Ile Val Lys
        180                 185                 190

Arg Cys Pro Asn His Glu Leu Gly Arg Asp Phe Asn Glu Gly Gln Ser
    195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
                260                 265                 270

Ile Ile Ile Thr Leu Glu Thr Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Pro Gly Val Lys Lys Arg Arg His Gly Asp Glu
        340                 345                 350

Asp Thr Tyr Tyr Leu Gln Val Arg Gly Arg Glu Asn Phe Glu Ile Leu
    355                 360                 365

Met Lys Leu Lys Glu Ser Leu Glu Leu Met Glu Leu Val Pro Gln Pro
370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Val Asn Lys Leu Pro Ser Val Asn Gln Leu Val Gly
        420                 425                 430

Gln Pro Pro Pro His Ser Ser Ala Ala Thr Pro Asn Leu Gly Pro Val
    435                 440                 445

Gly Ser Gly Met Leu Asn Asn His Gly His Ala Val Pro Ala Asn Ser
    450                 455                 460

Glu Met Thr Ser Ser His Gly Thr Gln Ser Met Val Ser Gly Ser His
465                 470                 475                 480

Cys Thr Pro Pro Pro Tyr His Ala Asp Pro Ser Leu Val Ser Phe
                485                 490                 495

Leu Thr Gly Leu Gly Cys Pro Asn Cys Ile Glu Tyr Phe Thr Ser Gln
        500                 505                 510

Gly Leu Gln Ser Ile Tyr His Leu Gln Asn Leu Thr Ile Glu Asp Leu
    515                 520                 525
```

```
Gly Ala Leu Lys Ile Pro Glu Gln Tyr Arg Met Thr Ile Trp Arg Gly
            530                 535                 540

Leu Gln Asp Leu Lys Gln Gly His Asp Tyr Gly Ala Ala Ala Gln Gln
545                 550                 555                 560

Leu Leu Arg Ser Ser Asn Ala Ala Ile Ser Ile Gly Gly Ser Gly
            565                 570                 575

Glu Leu Gln Arg Gln Arg Val Met Glu Ala Val His Phe Arg Val Arg
            580                 585                 590

His Thr Ile Thr Ile Pro Asn Arg Gly Gly Pro Gly Ala Gly Pro Asp
            595                 600                 605

Glu Trp Ala Asp Phe Gly Phe Asp Leu Pro Asp Cys Lys Ala Arg Lys
            610                 615                 620

Gln Pro Ile Lys Glu Glu Phe Thr Glu Ala Glu Ile His
625                 630                 635

<210> SEQ ID NO 3
<211> LENGTH: 2034
<212> TYPE: DNA
<213> ORGANISM: Cebus apella
<220> FEATURE:
<221> NAME/KEY: CDS
<222> LOCATION: (156)..(1652)

<400> SEQUENCE: 3
tgcctccccg cccgcgcacc cgccccgagg cctgtgctcc tgcgaagggg acgcagcgaa      60
gccggggccc gcgccaggcc ggccgggacg gacgccgatg cccggagctg cgacggctgc     120
agagcgagct gccctcggag gccggtgtga ggaag atg gcc cag tcc acc acc       173
                                      Met Ala Gln Ser Thr Thr
                                        1               5 acc tcc ccc gat ggg ggc acc acg ttt gag cac ctc tgg agc tct ctg      221
Thr Ser Pro Asp Gly Gly Thr Thr Phe Glu His Leu Trp Ser Ser Leu
             10                  15                  20 gaa cca gac agc acc tac ttc gac ctt ccc cag tca agc cgg ggg aat      269
Glu Pro Asp Ser Thr Tyr Phe Asp Leu Pro Gln Ser Ser Arg Gly Asn
         25                  30                  35 aat gag gtg gtg ggt ggc acg gat tcc agc atg gac gtc ttc cac cta      317
Asn Glu Val Val Gly Gly Thr Asp Ser Ser Met Asp Val Phe His Leu
     40                  45                  50 gag ggc atg acc aca tct gtc atg gcc cag ttc aat ttg ctg agc agc      365
Glu Gly Met Thr Thr Ser Val Met Ala Gln Phe Asn Leu Leu Ser Ser
55                  60                  65                  70 acc atg gac cag atg agc agc cgc gct gcc tcg gcc agc ccg tac acc      413
Thr Met Asp Gln Met Ser Ser Arg Ala Ala Ser Ala Ser Pro Tyr Thr
                 75                  80                  85 ccg gag cac gcc gcc agc gtg ccc acc cat tca ccc tac gca cag ccc      461
Pro Glu His Ala Ala Ser Val Pro Thr His Ser Pro Tyr Ala Gln Pro
             90                  95                 100 agc tcc acc ttc gac acc atg tcg ccc gcg cct gtc atc ccc tcc aac      509
Ser Ser Thr Phe Asp Thr Met Ser Pro Ala Pro Val Ile Pro Ser Asn
        105                 110                 115 acc gac tat ccc gga ccc cac cac ttc gag gtc act ttc cag cag tcc      557
Thr Asp Tyr Pro Gly Pro His His Phe Glu Val Thr Phe Gln Gln Ser
    120                 125                 130 agc acg gcc aag tca gcc acc tgg acg tac tcc cca ctc ttg aag aaa      605
Ser Thr Ala Lys Ser Ala Thr Trp Thr Tyr Ser Pro Leu Leu Lys Lys
135                 140                 145                 150 ctc tac tgc cag atc gcc aag aca tgc ccc atc cag atc aag gtg tcc      653
Leu Tyr Cys Gln Ile Ala Lys Thr Cys Pro Ile Gln Ile Lys Val Ser
                155                 160                 165
```

```
gcc cca ccg ccc ccg ggc acc gcc atc cgg gcc atg cct gtc tac aag      701
Ala Pro Pro Pro Pro Gly Thr Ala Ile Arg Ala Met Pro Val Tyr Lys
            170                 175                 180 aag gcg gag cac gtg acc gac atc gtg aag cgc tgc ccc aac cac gag      749
Lys Ala Glu His Val Thr Asp Ile Val Lys Arg Cys Pro Asn His Glu
        185                 190                 195 ctc ggg agg gac ttc aac gaa gga cag tct gcc cca gcc agc cac ctc      797
Leu Gly Arg Asp Phe Asn Glu Gly Gln Ser Ala Pro Ala Ser His Leu
    200                 205                 210 atc cgt gtg gaa ggc aat aat ctc tcg cag tat gtg gac gac cct gtc      845
Ile Arg Val Glu Gly Asn Asn Leu Ser Gln Tyr Val Asp Asp Pro Val
215                 220                 225                 230 acc ggc agg cag agc gtc gtg gtg ccc tat gag cca cca cag gtg ggg      893
Thr Gly Arg Gln Ser Val Val Val Pro Tyr Glu Pro Pro Gln Val Gly
                235                 240                 245 aca gaa ttc acc acc atc ctg tac aac ttc atg tgt aac agc agc tgt      941
Thr Glu Phe Thr Thr Ile Leu Tyr Asn Phe Met Cys Asn Ser Ser Cys
            250                 255                 260 gtg ggg ggc atg aac cga cgg ccc atc ctc atc atc atc acc ctg gag      989
Val Gly Gly Met Asn Arg Arg Pro Ile Leu Ile Ile Ile Thr Leu Glu
        265                 270                 275 acg cgg gat ggg cag gtg ctg ggc cgc cgg tcc ttc gag ggc cgc atc     1037
Thr Arg Asp Gly Gln Val Leu Gly Arg Arg Ser Phe Glu Gly Arg Ile
    280                 285                 290 tgc gcc tgt cct ggc cgc gac cga aaa gcc gat gag gac cac tac cgg     1085
Cys Ala Cys Pro Gly Arg Asp Arg Lys Ala Asp Glu Asp His Tyr Arg
295                 300                 305                 310 gag cag cag gcc ttg aat gag agc tcc gcc aag aac ggg gct gcc agc     1133
Glu Gln Gln Ala Leu Asn Glu Ser Ser Ala Lys Asn Gly Ala Ala Ser
                315                 320                 325 aag cgc gcc ttc aag cag agt ccc cct gcc gtc ccc gcc ctg ggc ccg     1181
Lys Arg Ala Phe Lys Gln Ser Pro Pro Ala Val Pro Ala Leu Gly Pro
            330                 335                 340 ggt gtg aag aag cgg cgg cac gga gac gag gac acg tac tac ctg cag     1229
Gly Val Lys Lys Arg Arg His Gly Asp Glu Asp Thr Tyr Tyr Leu Gln
        345                 350                 355 gtg cga ggc cgc gag aac ttc gag atc ctg atg aag ctg aag gag agc     1277
Val Arg Gly Arg Glu Asn Phe Glu Ile Leu Met Lys Leu Lys Glu Ser
    360                 365                 370 ctg gag ctg atg gag ttg gtg ccg cag ccg ctg gta gac tcc tat cgg     1325
Leu Glu Leu Met Glu Leu Val Pro Gln Pro Leu Val Asp Ser Tyr Arg
375                 380                 385                 390 cag cag cag cag ctc cta cag agg ccg agt cac cta cag ccc cca tcc     1373
Gln Gln Gln Gln Leu Leu Gln Arg Pro Ser His Leu Gln Pro Pro Ser
                395                 400                 405 tac ggg ccg gtc ctc tcg ccc atg aac aag gtg cac ggg ggc gtg aac     1421
Tyr Gly Pro Val Leu Ser Pro Met Asn Lys Val His Gly Gly Val Asn
            410                 415                 420 aag ctg ccc tcc gtc aac cag ctg gtg ggc cag cct ccc ccg cac agc     1469
Lys Leu Pro Ser Val Asn Gln Leu Val Gly Gln Pro Pro Pro His Ser
        425                 430                 435 tcg gca gct aca ccc aac ctg gga cct gtg ggc tct ggg atg ctc aac     1517
Ser Ala Ala Thr Pro Asn Leu Gly Pro Val Gly Ser Gly Met Leu Asn
    440                 445                 450 aac cac ggc cac gca gtg cca gcc aac agc gag atg acc agc agc cac     1565
Asn His Gly His Ala Val Pro Ala Asn Ser Glu Met Thr Ser Ser His
455                 460                 465                 470 ggc acc cag tcc atg gtc tcg ggg tcc cac tgc act ccg cca ccc ccc     1613
Gly Thr Gln Ser Met Val Ser Gly Ser His Cys Thr Pro Pro Pro Pro
```

-continued

```
                    475            480            485
tac cac gcc gac ccc agc ctc gtc agg acc tgg ggg ccc tgaagatccc    1662
Tyr His Ala Asp Pro Ser Leu Val Arg Thr Trp Gly Pro
            490                495 cgagcagtat cgcatgacca tctggcgggg cctgcaggac ctgaagcagg gccacgacta  1722
cggcgccgcc gcgcagcagc tgctccgctc cagcaacgcg gccgccattt ccatcggcgg  1782
ctccggggag ctgcagcgcc agcgggtcat ggaggccgtg cacttccgcg tgcgccacac  1842
catcaccatc cccaaccgcg gcggccccgg cgccggcccc gacgagtggg cggacttcgg  1902
cttcgacctg cccgactgca aggcccgcaa gcagcccatc aaggaggagt tcacggaggc  1962
cgagatccac tgaggggccg ggcccagcca gagcctgtgc caccgcccag agacccaggc  2022
cgcctcgctc tc                                                      2034
```

<210> SEQ ID NO 4
<211> LENGTH: 499
<212> TYPE: PRT
<213> ORGANISM: Cebus apella

<400> SEQUENCE: 4

```
Met Ala Gln Ser Thr Thr Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Ala Pro Pro Pro Gly Thr Ala Ile Arg
                165                 170                 175

Ala Met Pro Val Tyr Lys Lys Ala Glu His Val Thr Asp Ile Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270
```

```
Ile Ile Ile Thr Leu Glu Thr Arg Asp Gly Gln Val Leu Gly Arg Arg
            275                 280                 285

Ser Phe Glu Gly Arg Ile Cys Ala Cys Pro Gly Arg Asp Arg Lys Ala
        290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Pro Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Val Asn Lys Leu Pro Ser Val Asn Gln Leu Val Gly
            420                 425                 430

Gln Pro Pro Pro His Ser Ser Ala Ala Thr Pro Asn Leu Gly Pro Val
        435                 440                 445

Gly Ser Gly Met Leu Asn Asn His Gly His Ala Val Pro Ala Asn Ser
    450                 455                 460

Glu Met Thr Ser Ser His Gly Thr Gln Ser Met Val Ser Gly Ser His
465                 470                 475                 480

Cys Thr Pro Pro Pro Tyr His Ala Asp Pro Ser Leu Val Arg Thr
                485                 490                 495

Trp Gly Pro

<210> SEQ ID NO 5
<211> LENGTH: 2156
<212> TYPE: DNA
<213> ORGANISM: Homo sapiens
<220> FEATURE:
<221> NAME/KEY: CDS
<222> LOCATION: (33)..(1940)

<400> SEQUENCE: 5
gcgagctgcc ctcggaggcc ggcgtgggga ag atg gcc cag tcc acc gcc acc      53
                                    Met Ala Gln Ser Thr Ala Thr
                                    1               5 tcc cct gat ggg ggc acc acg ttt gag cac ctc tgg agc tct ctg gaa     101
Ser Pro Asp Gly Gly Thr Thr Phe Glu His Leu Trp Ser Ser Leu Glu
        10                  15                  20 cca gac agc acc tac ttc gac ctt ccc cag tca agc cgg ggg aat aat     149
Pro Asp Ser Thr Tyr Phe Asp Leu Pro Gln Ser Ser Arg Gly Asn Asn
25                  30                  35 gag gtg gtg ggc gga acg gat tcc agc atg gac gtc ttc cac ctg gag     197
Glu Val Val Gly Gly Thr Asp Ser Ser Met Asp Val Phe His Leu Glu
40                  45                  50                  55 ggc atg act aca tct gtc atg gcc cag ttc aat ctg ctg agc agc acc     245
Gly Met Thr Thr Ser Val Met Ala Gln Phe Asn Leu Leu Ser Ser Thr
            60                  65                  70 atg gac cag atg agc agc cgc gcg gcc tcg gcc agc ccc tac acc cca     293
Met Asp Gln Met Ser Ser Arg Ala Ala Ser Ala Ser Pro Tyr Thr Pro
    75                  80                  85
```

-continued

| | | |
|---|---|---|
| gag cac gcc gcc agc gtg ccc acc cac tcg ccc tac gca caa ccc agc<br>Glu His Ala Ala Ser Val Pro Thr His Ser Pro Tyr Ala Gln Pro Ser<br>     90                        95                       100 | 341 |
| tcc acc ttc gac acc atg tcg ccg gcg cct gtc atc ccc tcc aac acc<br>Ser Thr Phe Asp Thr Met Ser Pro Ala Pro Val Ile Pro Ser Asn Thr<br>105                   110                     115 | 389 |
| gac tac ccc gga ccc cac cac ttt gag gtc act ttc cag cag tcc agc<br>Asp Tyr Pro Gly Pro His His Phe Glu Val Thr Phe Gln Gln Ser Ser<br>120                  125                   130                  135 | 437 |
| acg gcc aag tca gcc acc tgg acg tac tcc ccg ctc ttg aag aaa ctc<br>Thr Ala Lys Ser Ala Thr Trp Thr Tyr Ser Pro Leu Leu Lys Lys Leu<br>             140                     145                  150 | 485 |
| tac tgc cag atc gcc aag aca tgc ccc atc cag atc aag gtg tcc acc<br>Tyr Cys Gln Ile Ala Lys Thr Cys Pro Ile Gln Ile Lys Val Ser Thr<br>         155                     160                  165 | 533 |
| ccg cca ccc cca ggc act gcc atc cgg gcc atg cct gtt tac aag aaa<br>Pro Pro Pro Pro Gly Thr Ala Ile Arg Ala Met Pro Val Tyr Lys Lys<br>    170                     175                     180 | 581 |
| gcg gag cac gtg acc gac gtc gtg aaa cgc tgc ccc aac cac gag ctc<br>Ala Glu His Val Thr Asp Val Val Lys Arg Cys Pro Asn His Glu Leu<br>185                   190                   195 | 629 |
| ggg agg gac ttc aac gaa gga cag tct gct cca gcc agc cac ctc atc<br>Gly Arg Asp Phe Asn Glu Gly Gln Ser Ala Pro Ala Ser His Leu Ile<br>200                  205                   210                  215 | 677 |
| cgc gtg gaa ggc aat aat ctc tcg cag tat gtg gat gac cct gtc acc<br>Arg Val Glu Gly Asn Asn Leu Ser Gln Tyr Val Asp Asp Pro Val Thr<br>             220                     225                  230 | 725 |
| ggc agg cag agc gtc gtg gtg ccc tat gag cca cca cag gtg ggg acg<br>Gly Arg Gln Ser Val Val Val Pro Tyr Glu Pro Pro Gln Val Gly Thr<br>         235                     240                  245 | 773 |
| gaa ttc acc acc atc ctg tac aac ttc atg tgt aac agc agc tgt gta<br>Glu Phe Thr Thr Ile Leu Tyr Asn Phe Met Cys Asn Ser Ser Cys Val<br>    250                     255                     260 | 821 |
| ggg ggc atg aac cgg cgg ccc atc ctc atc atc atc acc ctg gag atg<br>Gly Gly Met Asn Arg Arg Pro Ile Leu Ile Ile Ile Thr Leu Glu Met<br>265                   270                   275 | 869 |
| cgg gat ggg cag gtg ctg ggc cgc cgg tcc ttt gag ggc cgc atc tgc<br>Arg Asp Gly Gln Val Leu Gly Arg Arg Ser Phe Glu Gly Arg Ile Cys<br>280                   285                   290                  295 | 917 |
| gcc tgt cct ggc cgc gac cga aaa gct gat gag gac cac tac cgg gag<br>Ala Cys Pro Gly Arg Asp Arg Lys Ala Asp Glu Asp His Tyr Arg Glu<br>             300                     305                  310 | 965 |
| cag cag gcc ctg aac gag agc tcc gcc aag aac ggg gcc gcc agc aag<br>Gln Gln Ala Leu Asn Glu Ser Ser Ala Lys Asn Gly Ala Ala Ser Lys<br>         315                     320                  325 | 1013 |
| cgt gcc ttc aag cag agc ccc cct gcc gtc ccc gcc ctt ggt gcc ggt<br>Arg Ala Phe Lys Gln Ser Pro Pro Ala Val Pro Ala Leu Gly Ala Gly<br>    330                     335                     340 | 1061 |
| gtg aag aag cgg cgg cat gga gac gag gac acg tac tac ctt cag gtg<br>Val Lys Lys Arg Arg His Gly Asp Glu Asp Thr Tyr Tyr Leu Gln Val<br>345                   350                   355 | 1109 |
| cga ggc cgg gag aac ttt gag atc ctg atg aag ctg aaa gag agc ctg<br>Arg Gly Arg Glu Asn Phe Glu Ile Leu Met Lys Leu Lys Glu Ser Leu<br>360                   365                   370                  375 | 1157 |
| gag ctg atg gag ttg gtg ccg cag cca ctg gtg gac tcc tat cgg cag<br>Glu Leu Met Glu Leu Val Pro Gln Pro Leu Val Asp Ser Tyr Arg Gln<br>             380                     385                  390 | 1205 |
| cag cag cag ctc cta cag agg ccg agt cac cta cag ccc cgg tcc tac<br>Gln Gln Gln Leu Leu Gln Arg Pro Ser His Leu Gln Pro Pro Ser Tyr<br>         395                     400                  405 | 1253 |

```
ggg ccg gtc ctc tcg ccc atg aac aag gtg cac ggg ggc atg aac aag      1301
Gly Pro Val Leu Ser Pro Met Asn Lys Val His Gly Gly Met Asn Lys
        410                 415                 420 ctg ccc tcc gtc aac cag ctg gtg ggc cag cct ccc ccg cac agt tcg      1349
Leu Pro Ser Val Asn Gln Leu Val Gly Gln Pro Pro Pro His Ser Ser
    425                 430                 435 gca gct aca ccc aac ctg ggg ccc gtg ggc ccc ggg atg ctc aac aac      1397
Ala Ala Thr Pro Asn Leu Gly Pro Val Gly Pro Gly Met Leu Asn Asn
440                 445                 450                 455 cat ggc cac gca gtg cca gcc aac ggc gag atg agc agc agc cac agc      1445
His Gly His Ala Val Pro Ala Asn Gly Glu Met Ser Ser Ser His Ser
                460                 465                 470 gcc cag tcc atg gtc tcg ggg tcc cac tgc act ccg cca ccc ccc tac      1493
Ala Gln Ser Met Val Ser Gly Ser His Cys Thr Pro Pro Pro Pro Tyr
            475                 480                 485 cac gcc gac ccc agc ctc gtc agt ttt tta aca gga ttg ggg tgt cca      1541
His Ala Asp Pro Ser Leu Val Ser Phe Leu Thr Gly Leu Gly Cys Pro
        490                 495                 500 aac tgc atc gag tat ttc acc tcc caa ggg tta cag agc att tac cac      1589
Asn Cys Ile Glu Tyr Phe Thr Ser Gln Gly Leu Gln Ser Ile Tyr His
    505                 510                 515 ctg cag aac ctg acc att gag gac ctg ggg gcc ctg aag atc ccc gag      1637
Leu Gln Asn Leu Thr Ile Glu Asp Leu Gly Ala Leu Lys Ile Pro Glu
520                 525                 530                 535 cag tac cgc atg acc atc tgg cgg ggc ctg cag gac ctg aag cag ggc      1685
Gln Tyr Arg Met Thr Ile Trp Arg Gly Leu Gln Asp Leu Lys Gln Gly
                540                 545                 550 cac gac tac agc acc gcg cag cag ctg ctc cgc tct agc aac gcg gcc      1733
His Asp Tyr Ser Thr Ala Gln Gln Leu Leu Arg Ser Ser Asn Ala Ala
            555                 560                 565 acc atc tcc atc ggc ggc tca ggg gaa ctg cag cgc cag cgg gtc atg      1781
Thr Ile Ser Ile Gly Gly Ser Gly Glu Leu Gln Arg Gln Arg Val Met
        570                 575                 580 gag gcc gtg cac ttc cgc gtg cgc cac acc atc acc atc ccc aac cgc      1829
Glu Ala Val His Phe Arg Val Arg His Thr Ile Thr Ile Pro Asn Arg
    585                 590                 595 ggc ggc cca ggc ggc ggc cct gac gag tgg gcg gac ttc ggc ttc gac      1877
Gly Gly Pro Gly Gly Gly Pro Asp Glu Trp Ala Asp Phe Gly Phe Asp
600                 605                 610                 615 ctg ccc gac tgc aag gcc cgc aag cag ccc atc aag gag gag ttc acg      1925
Leu Pro Asp Cys Lys Ala Arg Lys Gln Pro Ile Lys Glu Glu Phe Thr
                620                 625                 630 gag gcc gag atc cac tgagggcctc gcctggctgc agcctgcgcc accgcccaga      1980
Glu Ala Glu Ile His
            635 gacccaagct gcctcccctc tccttcctgt gtgtccaaaa ctgcctcagg aggcaggacc    2040 ttcgggctgt gcccggggaa aggcaaggtc cggcccatcc ccaggcacct cacaggcccc    2100 aggaaaggcc cagccaccga agccgcctgt ggacagcctg agtcacctgc agaacc        2156

<210> SEQ ID NO 6
<211> LENGTH: 636
<212> TYPE: PRT
<213> ORGANISM: Homo sapiens

<400> SEQUENCE: 6

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
```

-continued

```
                    20                  25                  30
        Gln Ser Ser Arg Gly Asn Asn Glu Val Val Gly Gly Thr Asp Ser Ser
                     35                  40                  45

Met Asp Val Phe His Leu Glu Gly Met Thr Thr Ser Val Met Ala Gln
         50                  55                  60

Phe Asn Leu Leu Ser Ser Thr Met Asp Gln Met Ser Ser Arg Ala Ala
         65                  70                  75                  80

Ser Ala Ser Pro Tyr Thr Pro Glu His Ala Ala Ser Val Pro Thr His
                             85                  90                  95

Ser Pro Tyr Ala Gln Pro Ser Ser Thr Phe Asp Thr Met Ser Pro Ala
                        100                 105                 110

Pro Val Ile Pro Ser Asn Thr Asp Tyr Pro Gly Pro His His Phe Glu
                        115                 120                 125

Val Thr Phe Gln Gln Ser Ser Thr Ala Lys Ser Ala Thr Trp Thr Tyr
                    130                 135                 140

Ser Pro Leu Leu Lys Lys Leu Tyr Cys Gln Ile Ala Lys Thr Cys Pro
        145                 150                 155                 160

Ile Gln Ile Lys Val Ser Thr Pro Pro Pro Gly Thr Ala Ile Arg
                        165                 170                 175

Ala Met Pro Val Tyr Lys Lys Ala Glu His Val Thr Asp Val Val Lys
                        180                 185                 190

Arg Cys Pro Asn His Glu Leu Gly Arg Asp Phe Asn Glu Gly Gln Ser
                        195                 200                 205

Ala Pro Ala Ser His Leu Ile Arg Val Glu Gly Asn Asn Leu Ser Gln
            210                 215                 220

Tyr Val Asp Asp Pro Val Thr Gly Arg Gln Ser Val Val Val Pro Tyr
        225                 230                 235                 240

Glu Pro Pro Gln Val Gly Thr Glu Phe Thr Thr Ile Leu Tyr Asn Phe
                        245                 250                 255

Met Cys Asn Ser Ser Cys Val Gly Gly Met Asn Arg Arg Pro Ile Leu
                        260                 265                 270

Ile Ile Ile Thr Leu Glu Met Arg Asp Gly Gln Val Leu Gly Arg Arg
                    275                 280                 285

Ser Phe Glu Gly Arg Ile Cys Ala Cys Pro Gly Arg Asp Arg Lys Ala
            290                 295                 300

Asp Glu Asp His Tyr Arg Glu Gln Gln Ala Leu Asn Glu Ser Ser Ala
        305                 310                 315                 320

Lys Asn Gly Ala Ala Ser Lys Arg Ala Phe Lys Gln Ser Pro Pro Ala
                        325                 330                 335

Val Pro Ala Leu Gly Ala Gly Val Lys Lys Arg Arg His Gly Asp Glu
                        340                 345                 350

Asp Thr Tyr Tyr Leu Gln Val Arg Gly Arg Glu Asn Phe Glu Ile Leu
                    355                 360                 365

Met Lys Leu Lys Glu Ser Leu Glu Leu Met Glu Leu Val Pro Gln Pro
                370                 375                 380

Leu Val Asp Ser Tyr Arg Gln Gln Gln Leu Leu Gln Arg Pro Ser
        385                 390                 395                 400

His Leu Gln Pro Pro Ser Tyr Gly Pro Val Leu Ser Pro Met Asn Lys
                        405                 410                 415

Val His Gly Gly Met Asn Lys Leu Pro Ser Val Asn Gln Leu Val Gly
                        420                 425                 430

Gln Pro Pro Pro His Ser Ser Ala Ala Thr Pro Asn Leu Gly Pro Val
                    435                 440                 445
```

```
Gly Pro Gly Met Leu Asn Asn His Gly His Ala Val Pro Ala Asn Gly
    450                 455                 460
Glu Met Ser Ser His Ser Ala Gln Ser Met Val Ser Gly Ser His
465                 470                 475                 480
Cys Thr Pro Pro Pro Tyr His Ala Asp Pro Ser Leu Val Ser Phe
                    485                 490                 495
Leu Thr Gly Leu Gly Cys Pro Asn Cys Ile Glu Tyr Phe Thr Ser Gln
                500                 505                 510
Gly Leu Gln Ser Ile Tyr His Leu Gln Asn Leu Thr Ile Glu Asp Leu
            515                 520                 525
Gly Ala Leu Lys Ile Pro Glu Gln Tyr Arg Met Thr Ile Trp Arg Gly
        530                 535                 540
Leu Gln Asp Leu Lys Gln Gly His Asp Tyr Ser Thr Ala Gln Gln Leu
545                 550                 555                 560
Leu Arg Ser Ser Asn Ala Ala Thr Ile Ser Ile Gly Gly Ser Gly Glu
                565                 570                 575
Leu Gln Arg Gln Arg Val Met Glu Ala Val His Phe Arg Val Arg His
                580                 585                 590
Thr Ile Thr Ile Pro Asn Arg Gly Pro Gly Gly Pro Asp Glu
                595                 600                 605
Trp Ala Asp Phe Gly Phe Asp Leu Pro Asp Cys Lys Ala Arg Lys Gln
            610                 615                 620
Pro Ile Lys Glu Glu Phe Thr Glu Ala Glu Ile His
625                 630                 635

<210> SEQ ID NO 7
<211> LENGTH: 2040
<212> TYPE: DNA
<213> ORGANISM: Mus musculus
<220> FEATURE:
<221> NAME/KEY: CDS
<222> LOCATION: (124)..(1890)

<400> SEQUENCE: 7
tgatctccct gtggcctgca ggggactgag ccagggagta gatgccctga gaccccaagg     60
gacacccaag gaaaccttgc tggctttgag aaagggatcg tctctctcct gcccaagaga    120 agc atg tgt atg ggc cct gtg tat gaa tcc ttg ggg cag gcc cag ttc    168
    Met Cys Met Gly Pro Val Tyr Glu Ser Leu Gly Gln Ala Gln Phe
    1               5                   10                  15 aat ttg ctc agc agt gcc atg gac cag atg ggc agc cgt gcg gcc ccg    216
Asn Leu Leu Ser Ser Ala Met Asp Gln Met Gly Ser Arg Ala Ala Pro
                20                  25                  30 gcg agc ccc tac acc ccg gag cac gcc gcc agc gcg ccc acc cac tcg    264
Ala Ser Pro Tyr Thr Pro Glu His Ala Ala Ser Ala Pro Thr His Ser
            35                  40                  45 ccc tac gcg cag ccc agc tcc acc ttc gac acc atg tct ccg gcg cct    312
Pro Tyr Ala Gln Pro Ser Ser Thr Phe Asp Thr Met Ser Pro Ala Pro
        50                  55                  60 gtc atc cct tcc aat acc gac tac ccc ggc ccc cac cac ttc gag gtc    360
Val Ile Pro Ser Asn Thr Asp Tyr Pro Gly Pro His His Phe Glu Val
65                  70                  75 acc ttc cag cag tcg agc act gcc aag tcg gcc acc tgg aca tac tcc    408
Thr Phe Gln Gln Ser Ser Thr Ala Lys Ser Ala Thr Trp Thr Tyr Ser
80                  85                  90                  95 cca ctc ttg aag aag ttg tac tgt cag att gct aag aca tgc ccc atc    456
Pro Leu Leu Lys Lys Leu Tyr Cys Gln Ile Ala Lys Thr Cys Pro Ile
                100                 105                 110
```

-continued

| | | |
|---|---|---|
| cag atc aaa gtg tcc aca cca cca ccc ccg ggc acg gcc atc cgg gcc<br>Gln Ile Lys Val Ser Thr Pro Pro Pro Pro Gly Thr Ala Ile Arg Ala<br>  115             120                 125 | 504 | |
| atg cct gtc tac aag aag gca gag cat gtg acc gac att gtt aag cgc<br>Met Pro Val Tyr Lys Lys Ala Glu His Val Thr Asp Ile Val Lys Arg<br>          130                 135             140 | 552 | |
| tgc ccc aac cac gag ctt gga agg gac ttc aat gaa gga cag tct gcc<br>Cys Pro Asn His Glu Leu Gly Arg Asp Phe Asn Glu Gly Gln Ser Ala<br>145                 150                 155 | 600 | |
| ccg gct agc cac ctc atc cgt gta gaa ggc aac aac ctc gcc cag tac<br>Pro Ala Ser His Leu Ile Arg Val Glu Gly Asn Asn Leu Ala Gln Tyr<br>160                 165                 170                 175 | 648 | |
| gtg gat gac cct gtc acc gga agg cag agt gtg gtt gtg ccg tat gaa<br>Val Asp Asp Pro Val Thr Gly Arg Gln Ser Val Val Val Pro Tyr Glu<br>          180                 185                 190 | 696 | |
| ccc cca cag gtg gga aca gaa ttt acc acc atc ctg tac aac ttc atg<br>Pro Pro Gln Val Gly Thr Glu Phe Thr Thr Ile Leu Tyr Asn Phe Met<br>      195                 200                 205 | 744 | |
| tgt aac agc agc tgt gtg ggg ggc atg aat cgg agg ccc atc ctt gtc<br>Cys Asn Ser Ser Cys Val Gly Gly Met Asn Arg Arg Pro Ile Leu Val<br>          210                 215                 220 | 792 | |
| atc atc acc ctg gag acc cgg gat gga cag gtc ctg ggc cgc cgg tct<br>Ile Ile Thr Leu Glu Thr Arg Asp Gly Gln Val Leu Gly Arg Arg Ser<br>225                 230                 235 | 840 | |
| ttc gag ggt cgc atc tgt gcc tgt cct ggc cgt gac cgc aaa gct gat<br>Phe Glu Gly Arg Ile Cys Ala Cys Pro Gly Arg Asp Arg Lys Ala Asp<br>240                 245                 250                 255 | 888 | |
| gaa gac cat tac cgg gag caa cag gct ctg aat gaa agt acc acc aaa<br>Glu Asp His Tyr Arg Glu Gln Gln Ala Leu Asn Glu Ser Thr Thr Lys<br>          260                 265                 270 | 936 | |
| aat gga gct gcc agc aaa cgt gca ttc aag cag agc ccc cct gcc atc<br>Asn Gly Ala Ala Ser Lys Arg Ala Phe Lys Gln Ser Pro Pro Ala Ile<br>              275                 280                 285 | 984 | |
| cct gcc ctg ggt acc aac gtg aag aag aga cgc cac ggg gac gag gac<br>Pro Ala Leu Gly Thr Asn Val Lys Lys Arg Arg His Gly Asp Glu Asp<br>          290                 295                 300 | 1032 | |
| atg ttc tac atg cac gtg cga ggc cgg gag aac ttt gag atc ttg atg<br>Met Phe Tyr Met His Val Arg Gly Arg Glu Asn Phe Glu Ile Leu Met<br>305                 310                 315 | 1080 | |
| aaa gtc aag gag agc cta gaa ctg atg gag ctt gtg ccc cag cct ttg<br>Lys Val Lys Glu Ser Leu Glu Leu Met Glu Leu Val Pro Gln Pro Leu<br>320                 325                 330                 335 | 1128 | |
| gtt gac tcc tat cga cag cag cag cag cag cag ctc cta cag agg ccg<br>Val Asp Ser Tyr Arg Gln Gln Gln Gln Gln Gln Leu Leu Gln Arg Pro<br>              340                 345                 350 | 1176 | |
| agt cac ctg cag cct cca tcc tat ggg ccc gtg ctc tcc cca atg aac<br>Ser His Leu Gln Pro Pro Ser Tyr Gly Pro Val Leu Ser Pro Met Asn<br>          355                 360                 365 | 1224 | |
| aag gta cac ggt ggt gtc aac aaa ctg ccc tcc gtc aac cag ctg gtg<br>Lys Val His Gly Gly Val Asn Lys Leu Pro Ser Val Asn Gln Leu Val<br>          370                 375                 380 | 1272 | |
| ggc cag cct ccc ccg cac agc tca gca gct ggg ccc aac ctg ggg ccc<br>Gly Gln Pro Pro Pro His Ser Ser Ala Ala Gly Pro Asn Leu Gly Pro<br>385                 390                 395 | 1320 | |
| atg ggc tcc ggg atg ctc aac agc cac ggc cac agc atg ccg gcc aat<br>Met Gly Ser Gly Met Leu Asn Ser His Gly His Ser Met Pro Ala Asn<br>400                 405                 410                 415 | 1368 | |
| ggt gag atg aat gga ggc cac agc tcc cag acc atg gtt tcg gga tcc<br>Gly Glu Met Asn Gly Gly His Ser Ser Gln Thr Met Val Ser Gly Ser | 1416 | |

```
                420               425                430
cac tgc acc ccg cca ccc ccc tat cat gca gac ccc agc ctc gtc agt    1464
His Cys Thr Pro Pro Pro Pro Tyr His Ala Asp Pro Ser Leu Val Ser
            435                 440                 445 ttt ttg aca ggg ttg ggg tgt cca aac tgc atc gag tgc ttc act tcc    1512
Phe Leu Thr Gly Leu Gly Cys Pro Asn Cys Ile Glu Cys Phe Thr Ser
            450                 455                 460 caa ggg ttg cag agc atc tac cac ctg cag aac ctt acc atc gag gac    1560
Gln Gly Leu Gln Ser Ile Tyr His Leu Gln Asn Leu Thr Ile Glu Asp
        465                 470                 475 ctt ggg gct ctg aag gtc cct gac cag tac cgt atg acc atc tgg agg    1608
Leu Gly Ala Leu Lys Val Pro Asp Gln Tyr Arg Met Thr Ile Trp Arg
480                 485                 490                 495 ggc cta cag gac ctg aag cag agc cat gac tgc ggc cag caa ctg cta    1656
Gly Leu Gln Asp Leu Lys Gln Ser His Asp Cys Gly Gln Gln Leu Leu
                500                 505                 510 cgc tcc agc agc aac gcg gcc acc atc tcc atc ggc ggc tct ggc gag    1704
Arg Ser Ser Ser Asn Ala Ala Thr Ile Ser Ile Gly Gly Ser Gly Glu
            515                 520                 525 ctg cag cgg cag cgg gtc atg gaa gcc gtg cat ttc cgt gtg cgc cac    1752
Leu Gln Arg Gln Arg Val Met Glu Ala Val His Phe Arg Val Arg His
        530                 535                 540 acc atc aca atc ccc aac cgt gga ggc gca ggt gcg gtg aca ggt ccc    1800
Thr Ile Thr Ile Pro Asn Arg Gly Gly Ala Gly Ala Val Thr Gly Pro
    545                 550                 555 gac gag tgg gcg gac ttt ggc ttt gac ctg cct gac tgc aag tcc cgt    1848
Asp Glu Trp Ala Asp Phe Gly Phe Asp Leu Pro Asp Cys Lys Ser Arg
560                 565                 570                 575 aag cag ccc atc aaa gag gag ttc aca gag aca gag agc cac              1890
Lys Gln Pro Ile Lys Glu Glu Phe Thr Glu Thr Glu Ser His
                580                 585 tgaggaacgt accttcttct cctgtccttc ctctgtgaga aactgctctt ggaagtggga    1950
cctgttggct gtgcccacag aaaccagcaa ggaccttctg ccggatgcca ttcctgaagg    2010
gaagtcgctc atgaactaac tccctcttgg                                     2040

<210> SEQ ID NO 8
<211> LENGTH: 589
<212> TYPE: PRT
<213> ORGANISM: Mus musculus

<400> SEQUENCE: 8

Met Cys Met Gly Pro Val Tyr Glu Ser Leu Gly Gln Ala Gln Phe Asn
1               5                   10                  15

Leu Leu Ser Ser Ala Met Asp Gln Met Gly Ser Arg Ala Ala Pro Ala
            20                  25                  30

Ser Pro Tyr Thr Pro Glu His Ala Ala Ser Ala Pro Thr His Ser Pro
        35                  40                  45

Tyr Ala Gln Pro Ser Ser Thr Phe Asp Thr Met Ser Pro Ala Pro Val
    50                  55                  60

Ile Pro Ser Asn Thr Asp Tyr Pro Gly Pro His His Phe Glu Val Thr
65                  70                  75                  80

Phe Gln Gln Ser Ser Thr Ala Lys Ser Ala Thr Trp Thr Tyr Ser Pro
                85                  90                  95

Leu Leu Lys Lys Leu Tyr Cys Gln Ile Ala Lys Thr Cys Pro Ile Gln
            100                 105                 110

Ile Lys Val Ser Thr Pro Pro Pro Gly Thr Ala Ile Arg Ala Met
        115                 120                 125
```

-continued

Pro Val Tyr Lys Lys Ala Glu His Val Thr Asp Ile Val Lys Arg Cys
130                 135                 140

Pro Asn His Glu Leu Gly Arg Asp Phe Asn Glu Gly Gln Ser Ala Pro
145                 150                 155                 160

Ala Ser His Leu Ile Arg Val Glu Gly Asn Asn Leu Ala Gln Tyr Val
                165                 170                 175

Asp Asp Pro Val Thr Gly Arg Gln Ser Val Val Pro Tyr Glu Pro
        180                 185                 190

Pro Gln Val Gly Thr Glu Phe Thr Thr Ile Leu Tyr Asn Phe Met Cys
        195                 200                 205

Asn Ser Ser Cys Val Gly Gly Met Asn Arg Arg Pro Ile Leu Val Ile
210                 215                 220

Ile Thr Leu Glu Thr Arg Asp Gly Gln Val Leu Gly Arg Arg Ser Phe
225                 230                 235                 240

Glu Gly Arg Ile Cys Ala Cys Pro Gly Arg Asp Arg Lys Ala Asp Glu
                245                 250                 255

Asp His Tyr Arg Glu Gln Gln Ala Leu Asn Glu Ser Thr Thr Lys Asn
        260                 265                 270

Gly Ala Ala Ser Lys Arg Ala Phe Lys Gln Ser Pro Pro Ala Ile Pro
        275                 280                 285

Ala Leu Gly Thr Asn Val Lys Lys Arg Arg His Gly Asp Glu Asp Met
290                 295                 300

Phe Tyr Met His Val Arg Gly Arg Glu Asn Phe Glu Ile Leu Met Lys
305                 310                 315                 320

Val Lys Glu Ser Leu Glu Leu Met Glu Leu Val Pro Gln Pro Leu Val
                325                 330                 335

Asp Ser Tyr Arg Gln Gln Gln Gln Gln Leu Leu Gln Arg Pro Ser
        340                 345                 350

His Leu Gln Pro Pro Ser Tyr Gly Pro Val Leu Ser Pro Met Asn Lys
        355                 360                 365

Val His Gly Gly Val Asn Lys Leu Pro Ser Val Asn Gln Leu Val Gly
370                 375                 380

Gln Pro Pro His Ser Ser Ala Ala Gly Pro Asn Leu Gly Pro Met
385                 390                 395                 400

Gly Ser Gly Met Leu Asn Ser His Gly His Ser Met Pro Ala Asn Gly
                405                 410                 415

Glu Met Asn Gly Gly His Ser Ser Gln Thr Met Val Ser Gly Ser His
        420                 425                 430

Cys Thr Pro Pro Pro Tyr His Ala Asp Pro Ser Leu Val Ser Phe
        435                 440                 445

Leu Thr Gly Leu Gly Cys Pro Asn Cys Ile Glu Cys Phe Thr Ser Gln
450                 455                 460

Gly Leu Gln Ser Ile Tyr His Leu Gln Asn Leu Thr Ile Glu Asp Leu
465                 470                 475                 480

Gly Ala Leu Lys Val Pro Asp Gln Tyr Arg Met Thr Ile Trp Arg Gly
                485                 490                 495

Leu Gln Asp Leu Lys Gln Ser His Asp Cys Gly Gln Gln Leu Leu Arg
        500                 505                 510

Ser Ser Ser Asn Ala Ala Thr Ile Ser Ile Gly Gly Ser Gly Glu Leu
        515                 520                 525

Gln Arg Gln Arg Val Met Glu Ala Val His Phe Arg Val Arg His Thr
530                 535                 540

```
Ile Thr Ile Pro Asn Arg Gly Gly Ala Gly Ala Val Thr Gly Pro Asp
545                 550                 555                 560

Glu Trp Ala Asp Phe Gly Phe Asp Leu Pro Asp Cys Lys Ser Arg Lys
                565                 570                 575

Gln Pro Ile Lys Glu Glu Phe Thr Glu Thr Glu Ser His
            580                 585
```

<210> SEQ ID NO 9
<211> LENGTH: 758
<212> TYPE: DNA
<213> ORGANISM: Mus musculus
<220> FEATURE:
<221> NAME/KEY: CDS
<222> LOCATION: (389)..(757)

<400> SEQUENCE: 9

```
tggtcccgct tcgaccaaga ctccggctac cagcttgcgg gccccgcgga ggaggagacc      60
ccgctggggc tagctgggcg acgcgcgcca agcggcggcg ggaaggaggc ggggaggagcg    120 gggcccgaga ccccgactcg ggcagagcca gctggggagg cggggcgcgc gtgggagcca    180
ggggcccggg tggccggccc tcctccgcca cggctgagtg cccgcgctgc cttcccgccg    240
gtccgccaag aaaggcgcta agcctgcggc agtcccctcg ccgccgcctc cctgctccgc    300
acccttataa cccgccgtcc cgcatccagg cgaggaggca acgctgcagc ccagccctcg    360
ccgacgccga cgcccggccc ggagcaga atg agc ggc agc gtt ggg gag atg      412
                                Met Ser Gly Ser Val Gly Glu Met
                                  1               5 gcc cag acc tct tct tcc tcc tcc tcc acc ttc gag cac ctg tgg agt     460
Ala Gln Thr Ser Ser Ser Ser Ser Ser Thr Phe Glu His Leu Trp Ser
 10                  15                  20 tct cta gag cca gac agc acc tac ttt gac ctc ccc cag ccc agc caa     508
Ser Leu Glu Pro Asp Ser Thr Tyr Phe Asp Leu Pro Gln Pro Ser Gln
 25                  30                  35                  40 ggg act agc gag gca tca ggc agc gag gag tcc aac atg gat gtc ttc     556
Gly Thr Ser Glu Ala Ser Gly Ser Glu Glu Ser Asn Met Asp Val Phe
                 45                  50                  55 cac ctg caa ggc atg gcc cag ttc aat ttg ctc agc agt gcc atg gac     604
His Leu Gln Gly Met Ala Gln Phe Asn Leu Leu Ser Ser Ala Met Asp
             60                  65                  70 cag atg ggc agc cgt gcg gcc ccg gcg agc ccc tac acc ccg gag cac     652
Gln Met Gly Ser Arg Ala Ala Pro Ala Ser Pro Tyr Thr Pro Glu His
         75                  80                  85 gcc gcc agc gcg ccc acc cac tcg ccc tac gcg cag ccc agc tcc acc     700
Ala Ala Ser Ala Pro Thr His Ser Pro Tyr Ala Gln Pro Ser Ser Thr
     90                  95                 100 ttc gac acc atg tct ccg gcg cct gtc atc cct tcc aat acc gac tac     748
Phe Asp Thr Met Ser Pro Ala Pro Val Ile Pro Ser Asn Thr Asp Tyr
105                 110                 115                 120 ccc ggc ccc c                                                        758
Pro Gly Pro
```

<210> SEQ ID NO 10
<211> LENGTH: 123
<212> TYPE: PRT
<213> ORGANISM: Mus musculus

<400> SEQUENCE: 10

```
Met Ser Gly Ser Val Gly Glu Met Ala Gln Thr Ser Ser Ser Ser Ser
 1               5                  10                  15

Ser Thr Phe Glu His Leu Trp Ser Ser Leu Glu Pro Asp Ser Thr Tyr
```

```
                    20                  25                  30
Phe Asp Leu Pro Gln Pro Ser Gln Gly Thr Ser Glu Ala Ser Gly Ser
     35                  40                  45

Glu Glu Ser Asn Met Asp Val Phe His Leu Gln Gly Met Ala Gln Phe
 50                  55                  60

Asn Leu Leu Ser Ser Ala Met Asp Gln Met Gly Ser Arg Ala Ala Pro
65                  70                  75                  80

Ala Ser Pro Tyr Thr Pro Glu His Ala Ala Ser Ala Pro Thr His Ser
             85                  90                  95

Pro Tyr Ala Gln Pro Ser Ser Thr Phe Asp Thr Met Ser Pro Ala Pro
            100                 105                 110

Val Ile Pro Ser Asn Thr Asp Tyr Pro Gly Pro
            115                 120

<210> SEQ ID NO 11
<211> LENGTH: 559
<212> TYPE: DNA
<213> ORGANISM: Homo sapiens

<400> SEQUENCE: 11
cgaccttccc cagtcaagcc gggggaataa tgaggtggtg ggcggaacgg attccagcat      60
ggacgtcttc cacctggagg gcatgactac atctgtcatg catcctcggc tcctgcctca     120
ctagctgcgg agcctctccc gctcggtcca cgctgccggg cggccacgac cgtgacccct     180
cccctcgggc cgcccagatc catgcctcgt cccacgggac accagttccc tggcgtgtgc     240 agacccccg gcgcctacca tgctgtacgt cggtgacccc gcacggcacc tcgccacggc      300
ccagttcaat ctgctgagca gcaccatgga ccagatgagc agccgcgcgg cctcggccag     360 ccctacacc ccagagcacg ccgccagcgt gcccacccac tcgccctacg cacaacccag     420
ctccaccttc gacaccatgt cgccggcgcc tgtcatcccc tccaacaccg actaccccgg     480
accccaccac tttgaggtca cttttccagca gtccagcacg gccaagtcag ccacctggac     540
gtactccccg ctcttgaag                                                   559

<210> SEQ ID NO 12
<211> LENGTH: 1764
<212> TYPE: DNA
<213> ORGANISM: Homo sapiens

<400> SEQUENCE: 12
atgctgtacg tcggtgaccc cgcacggcac ctcgccacgg cccagttcaa tctgctgagc      60
agcaccatgg accagatgag cagccgcgcg gcctcggcca gccctacac cccagagcac     120 gccgccagcg tgcccaccca ctcgccctac gcacaaccca gctccacctt cgacaccatg     180
tcgccggcgc tgtcatcccc tccaacaccc gactaccccg gaccccacca ctttgaggtc     240
actttccagc agtccagcac ggccaagtca gccacctgga cgtactcccc gctcttgaag     300
aaactctact gccagatcgc caagacatgc cccatccaga tcaaggtgtc caccccgcca     360 ccccaggca ctgccatccg ggccatgcct gtttacaaga agcggagca cgtgaccgac     420 gtcgtgaaac gctgccccaa ccacgagctc gggagggact caacgaagg acagtctgct     480 ccagccagcc acctcatccg cgtggaaggc aataatctct cgcagtatgt ggatgaccct     540
gtcaccggca ggcagagcgt cgtggtgccc tatgagccac acaggtggg gacggaattc     600 accaccatcc tgtacaactt catgtgtaac agcagctgtg tagggggcat gaaccggcgg     660
cccatcctca tcatcatcac cctggagatg cgggatgggc aggtgctggg ccgccggtcc     720
```

```
tttgagggcc gcatctgcgc ctgtcctggc cgcgaccgaa aagctgatga ggaccactac    780
cgggagcagc aggccctgaa cgagagctcc gccaagaacg gggccgccag caagcgtgcc    840
ttcaagcaga gccccctgc cgtccccgcc cttggtgccg gtgtgaagaa gcggcggcat    900
ggagacgagg acacgtacta ccttcaggtg cgaggccggg agaactttga gatcctgatg    960
aagctgaaag agagcctgga gctgatggag ttggtgccgc agccactggt ggactcctat   1020
cggcagcagc agcagctcct acagaggccg agtcacctac agccccgtc ctacgggccg    1080 gtcctctcgc ccatgaacaa ggtgcacggg ggcatgaaca agctgccctc cgtcaaccag    1140
ctggtgggcc agcctccccc gcacagttcg gcagctacac ccaacctggg gcccgtgggc    1200
cccgggatgc tcaacaacca tggccacgca gtgccagcca acggcgagat gagcagcagc    1260
cacagcgccc agtccatggt ctcggggtcc cactgcactc cgccaccccc ctaccacgcc    1320
gaccccagcc tcgtcagttt tttaacagga ttggggtgtc caaactgcat cgagtatttc    1380
acctcccaag ggttacagag catttaccac ctgcagaacc tgaccattga ggacctgggg    1440
gccctgaaga tccccgagca gtaccgcatg accatctggc gggggcctgca ggacctgaag    1500 cagggccacg actacagcac cgcgcagcag ctgctccgct ctagcaacgc ggccaccatc    1560
tccatcggcg gctcagggga actgcagcgc cagcgggtca tggaggccgt gcacttccgc    1620
gtgcgccaca ccatcaccat ccccaaccgc ggcggcccag gcggcggccc tgacgagtgg    1680
gcggacttcg gcttcgacct gcccgactgc aaggcccgca gcagcccat caaggaggag    1740 ttcacggagg ccgagatcca ctga                                          1764
```

<210> SEQ ID NO 13
<211> LENGTH: 587
<212> TYPE: PRT
<213> ORGANISM: Homo sapiens

<400> SEQUENCE: 13

```
Met Leu Tyr Val Gly Asp Pro Ala Arg His Leu Ala Thr Ala Gln Phe
1               5                   10                  15

Asn Leu Leu Ser Ser Thr Met Asp Gln Met Ser Ser Arg Ala Ala Ser
            20                  25                  30

Ala Ser Pro Tyr Thr Pro Glu His Ala Ala Ser Val Pro Thr His Ser
        35                  40                  45

Pro Tyr Ala Gln Pro Ser Ser Thr Phe Asp Thr Met Ser Pro Ala Pro
    50                  55                  60

Val Ile Pro Ser Asn Thr Asp Tyr Pro Gly Pro His His Phe Glu Val
65                  70                  75                  80

Thr Phe Gln Gln Ser Ser Thr Ala Lys Ser Ala Thr Trp Thr Tyr Ser
                85                  90                  95

Pro Leu Leu Lys Lys Leu Tyr Cys Gln Ile Ala Lys Thr Cys Pro Ile
            100                 105                 110

Gln Ile Lys Val Ser Thr Pro Pro Pro Gly Thr Ala Ile Arg Ala
        115                 120                 125

Met Pro Val Tyr Lys Lys Ala Glu His Val Thr Asp Val Val Lys Arg
    130                 135                 140

Cys Pro Asn His Glu Leu Gly Arg Asp Phe Asn Glu Gly Gln Ser Ala
145                 150                 155                 160

Pro Ala Ser His Leu Ile Arg Val Glu Gly Asn Asn Leu Ser Gln Tyr
                165                 170                 175

Val Asp Asp Pro Val Thr Gly Arg Gln Ser Val Val Val Pro Tyr Glu
```

```
                180                 185                 190
Pro Pro Gln Val Gly Thr Glu Phe Thr Thr Ile Leu Tyr Asn Phe Met
        195                 200                 205
Cys Asn Ser Ser Cys Val Gly Gly Met Asn Arg Arg Pro Ile Leu Ile
        210                 215                 220
Ile Ile Thr Leu Glu Met Arg Asp Gly Gln Val Leu Gly Arg Arg Ser
225                 230                 235                 240
Phe Glu Gly Arg Ile Cys Ala Cys Pro Gly Arg Asp Arg Lys Ala Asp
                245                 250                 255
Glu Asp His Tyr Arg Glu Gln Gln Ala Leu Asn Glu Ser Ser Ala Lys
                260                 265                 270
Asn Gly Ala Ala Ser Lys Arg Ala Phe Lys Gln Ser Pro Pro Ala Val
                275                 280                 285
Pro Ala Leu Gly Ala Gly Val Lys Lys Arg Arg His Gly Asp Glu Asp
                290                 295                 300
Thr Tyr Tyr Leu Gln Val Arg Gly Arg Glu Asn Phe Glu Ile Leu Met
305                 310                 315                 320
Lys Leu Lys Glu Ser Leu Glu Leu Met Glu Leu Val Pro Gln Pro Leu
                325                 330                 335
Val Asp Ser Tyr Arg Gln Gln Gln Leu Leu Gln Arg Pro Ser His
                340                 345                 350
Leu Gln Pro Pro Ser Tyr Gly Pro Val Leu Ser Pro Met Asn Lys Val
                355                 360                 365
His Gly Gly Met Asn Lys Leu Pro Ser Val Asn Gln Leu Val Gly Gln
                370                 375                 380
Pro Pro Pro His Ser Ser Ala Ala Thr Pro Asn Leu Gly Pro Val Gly
385                 390                 395                 400
Pro Gly Met Leu Asn Asn His Gly His Ala Val Pro Ala Asn Gly Glu
                405                 410                 415
Met Ser Ser Ser His Ser Ala Gln Ser Met Val Ser Gly Ser His Cys
                420                 425                 430
Thr Pro Pro Pro Tyr His Ala Asp Pro Ser Leu Val Ser Phe Leu
        435                 440                 445
Thr Gly Leu Gly Cys Pro Asn Cys Ile Glu Tyr Phe Thr Ser Gln Gly
        450                 455                 460
Leu Gln Ser Ile Tyr His Leu Gln Asn Leu Thr Ile Glu Asp Leu Gly
465                 470                 475                 480
Ala Leu Lys Ile Pro Glu Gln Tyr Arg Met Thr Ile Trp Arg Gly Leu
                485                 490                 495
Gln Asp Leu Lys Gln Gly His Asp Tyr Ser Thr Ala Gln Gln Leu Leu
                500                 505                 510
Arg Ser Ser Asn Ala Ala Thr Ile Ser Ile Gly Gly Ser Gly Glu Leu
                515                 520                 525
Gln Arg Gln Arg Val Met Glu Ala Val His Phe Arg Val Arg His Thr
                530                 535                 540
Ile Thr Ile Pro Asn Arg Gly Pro Gly Gly Pro Asp Glu Trp
545                 550                 555                 560
Ala Asp Phe Gly Phe Asp Leu Pro Asp Cys Lys Ala Arg Lys Gln Pro
                565                 570                 575
Ile Lys Glu Glu Phe Thr Glu Ala Glu Ile His
                580                 585

<210> SEQ ID NO 14
```

<211> LENGTH: 1521
<212> TYPE: DNA
<213> ORGANISM: Homo sapiens

<400> SEQUENCE: 14

| | |
|---|---|
| atgctgtacg tcggtgaccc cgcacggcac ctcgccacgg cccagttcaa tctgctgagc | 60 |
| agcaccatgg accagatgag cagccgcgcg gcctcggcca gccctacac cccagagcac | 120 |
| gccgccagcg tgcccaccca ctcgccctac gcacaaccca gctccacctt cgacaccatg | 180 |
| tcgccggcgc ctgtcatccc ctccaacacc gactacccccg acccaccca ctttgaggtc | 240 |
| actttccagc agtccagcac ggccaagtca gccacctgga cgtactcccc gctcttgaag | 300 |
| aaactctact gccagatcgc caagacatgc cccatccaga tcaaggtgtc caccccgcca | 360 |
| ccccaggca ctgccatccg ggccatgcct gtttacaaga agcggagca cgtgaccgac | 420 |
| gtcgtgaaac gctgccccaa ccacgagctc ggggagggact tcaacgaagg acagtctgct | 480 |
| ccagccagcc acctcatccg cgtggaaggc aataatctct cgcagtatgt ggatgaccct | 540 |
| gtcaccggca ggcagagcgt cgtggtgccc tatgagccac acaggtggg gacggaattc | 600 |
| accaccatcc tgtacaactt catgtgtaac agcagctgtg taggggggcat gaaccggcgg | 660 |
| cccatcctca tcatcatcac cctggagatg cgggatgggc aggtgctggg ccgccggtcc | 720 |
| tttgagggcc gcatctgcgc ctgtcctggc cgcgaccgaa aagctgatga ggaccactac | 780 |
| cgggagcagc aggccctgaa cgagagctcc gccaagaacg gggccgccag caagcgtgcc | 840 |
| ttcaagcaga gcccccctgc cgtccccgcc cttggtgccg tgtgtaagaa gcggcggcat | 900 |
| ggagacgagg acacgtacta ccttcaggtg cgaggccggg agaactttga gatcctgatg | 960 |
| aagctgaaag agagcctgga gctgatggag ttggtgccgc agccactggt ggactcctat | 1020 |
| cggcagcagc agcagctcct acagaggccg ccccgggatg ctcaacaacc atggccacgc | 1080 |
| agtgccagcc aacggcgaga tgagcagcag ccacagcgcc cagtccatgg tctcggggtc | 1140 |
| ccactgcact ccgccacccc cctaccacgc cgaccccagc ctcgtcagga cctgggggcc | 1200 |
| ctgaagatcc ccgagcagta ccgcatgacc atctggcggg cctgcagga cctgaagcag | 1260 |
| ggccacgact acagcaccgc gcagcagctg ctccgctcta gcaacgcggc caccatctcc | 1320 |
| atcggcggct caggggaact gcagcgccag cgggtcatgg aggccgtgca cttccgcgtg | 1380 |
| cgccacacca tcaccatccc caaccgcggc ggccaggcg gcggccctga cgagtgggcg | 1440 |
| gacttcggct tcgacctgcc cgactgcaag gcccgcaagc agcccatcaa ggaggagttc | 1500 |
| acggaggccg agatccactg a | 1521 |

<210> SEQ ID NO 15
<211> LENGTH: 506
<212> TYPE: PRT
<213> ORGANISM: Homo sapiens

<400> SEQUENCE: 15

Met Leu Tyr Val Gly Asp Pro Ala Arg His Leu Ala Thr Ala Gln Phe
1               5                   10                  15

Asn Leu Leu Ser Ser Thr Met Asp Gln Met Ser Ser Arg Ala Ala Ser
            20                  25                  30

Ala Ser Pro Tyr Thr Pro Glu His Ala Ala Ser Val Pro Thr His Ser
        35                  40                  45

Pro Tyr Ala Gln Pro Ser Ser Thr Phe Asp Thr Met Ser Pro Ala Pro
    50                  55                  60

Val Ile Pro Ser Asn Thr Asp Tyr Pro Gly Pro His His Phe Glu Val

-continued

```
                65                  70                  75                  80
Thr Phe Gln Gln Ser Ser Thr Ala Lys Ser Ala Thr Trp Thr Tyr Ser
                        85                  90                  95
Pro Leu Leu Lys Lys Leu Tyr Cys Gln Ile Ala Lys Thr Cys Pro Ile
                100                 105                 110
Gln Ile Lys Val Ser Thr Pro Pro Pro Gly Thr Ala Ile Arg Ala
            115                 120                 125
Met Pro Val Tyr Lys Lys Ala Glu His Val Thr Asp Val Val Lys Arg
        130                 135                 140
Cys Pro Asn His Glu Leu Gly Arg Asp Phe Asn Glu Gly Gln Ser Ala
145                 150                 155                 160
Pro Ala Ser His Leu Ile Arg Val Glu Gly Asn Asn Leu Ser Gln Tyr
                165                 170                 175
Val Asp Asp Pro Val Thr Gly Arg Gln Ser Val Val Pro Tyr Glu
            180                 185                 190
Pro Pro Gln Val Gly Thr Glu Phe Thr Thr Ile Leu Tyr Asn Phe Met
        195                 200                 205
Cys Asn Ser Ser Cys Val Gly Gly Met Asn Arg Arg Pro Ile Leu Ile
    210                 215                 220
Ile Ile Thr Leu Glu Met Arg Asp Gly Gln Val Leu Gly Arg Arg Ser
225                 230                 235                 240
Phe Glu Gly Arg Ile Cys Ala Cys Pro Gly Arg Asp Arg Lys Ala Asp
                245                 250                 255
Glu Asp His Tyr Arg Glu Gln Gln Ala Leu Asn Glu Ser Ser Ala Lys
            260                 265                 270
Asn Gly Ala Ala Ser Lys Arg Ala Phe Lys Gln Ser Pro Pro Ala Val
        275                 280                 285
Pro Ala Leu Gly Ala Gly Val Lys Lys Arg Arg His Gly Asp Glu Asp
    290                 295                 300
Thr Tyr Tyr Leu Gln Val Arg Gly Arg Glu Asn Phe Glu Ile Leu Met
305                 310                 315                 320
Lys Leu Lys Glu Ser Leu Glu Leu Met Glu Leu Val Pro Gln Pro Leu
                325                 330                 335
Val Asp Ser Tyr Arg Gln Gln Gln Leu Leu Gln Arg Pro Pro Arg
            340                 345                 350
Asp Ala Gln Gln Pro Trp Pro Arg Ser Ala Ser Gln Arg Arg Asp Glu
        355                 360                 365
Gln Gln Pro Gln Arg Pro Val His Gly Leu Gly Val Pro Leu His Ser
    370                 375                 380
Ala Thr Pro Leu Pro Arg Arg Pro Gln Pro Arg Gln Asp Leu Gly Ala
385                 390                 395                 400
Leu Lys Ile Pro Glu Gln Tyr Arg Met Thr Ile Trp Arg Gly Leu Gln
                405                 410                 415
Asp Leu Lys Gln Gly His Asp Tyr Ser Thr Ala Gln Leu Leu Arg
            420                 425                 430
Ser Ser Asn Ala Ala Thr Ile Ser Ile Gly Gly Ser Gly Glu Leu Gln
        435                 440                 445
Arg Gln Arg Val Met Glu Ala Val His Phe Arg Val Arg His Thr Ile
    450                 455                 460
Thr Ile Pro Asn Arg Gly Gly Pro Gly Gly Pro Asp Glu Trp Ala
465                 470                 475                 480
Asp Phe Gly Phe Asp Leu Pro Asp Cys Lys Ala Arg Lys Gln Pro Ile
                485                 490                 495
```

```
Lys Glu Glu Phe Thr Glu Ala Glu Ile His
        500                 505

<210> SEQ ID NO 16
<211> LENGTH: 1870
<212> TYPE: DNA
<213> ORGANISM: Homo sapiens
<220> FEATURE:
<221> NAME/KEY: CDS
<222> LOCATION: (104)..(1867)

<400> SEQUENCE: 16
tgcccggggc tgcgacggct gcagggaacc agacagcacc tacttcgacc ttccccagtc      60
aagccggggg aataatgagg tggtgggcgg aacggattcc agc atg gac gtc ttc      115
                                              Met Asp Val Phe
                                                1 cac ctg gag ggc atg act aca tct gtc atg gcc cag ttc aat ctg ctg      163
His Leu Glu Gly Met Thr Thr Ser Val Met Ala Gln Phe Asn Leu Leu
  5              10                  15                  20 agc agc acc atg gac cag atg agc agc cgc gcg gcc tcg gcc agc ccc      211
Ser Ser Thr Met Asp Gln Met Ser Ser Arg Ala Ala Ser Ala Ser Pro
             25                  30                  35 tac acc cca gag cac gcc gcc agc gtg ccc acc cac tcg ccc tac gca      259
Tyr Thr Pro Glu His Ala Ala Ser Val Pro Thr His Ser Pro Tyr Ala
         40                  45                  50 caa ccc agc tcc acc ttc gac acc atg tcg ccg gcg cct gtc atc ccc      307
Gln Pro Ser Ser Thr Phe Asp Thr Met Ser Pro Ala Pro Val Ile Pro
     55                  60                  65 tcc aac acc gac tac ccc gga ccc cac cac ttt gag gtc act ttc cag      355
Ser Asn Thr Asp Tyr Pro Gly Pro His His Phe Glu Val Thr Phe Gln
 70                  75                  80 cag tcc agc acg gcc aag tca gcc acc tgg acg tac tcc ccg ctc ttg      403
Gln Ser Ser Thr Ala Lys Ser Ala Thr Trp Thr Tyr Ser Pro Leu Leu
85                  90                  95                 100 aag aaa ctc tac tgc cag atc gcc aag aca tgc ccc atc cag atc aag      451
Lys Lys Leu Tyr Cys Gln Ile Ala Lys Thr Cys Pro Ile Gln Ile Lys
                105                 110                 115 gtg tcc acc ccg cca ccc cca ggc act gcc atc cgg gcc atg cct gtt      499
Val Ser Thr Pro Pro Pro Pro Gly Thr Ala Ile Arg Ala Met Pro Val
            120                 125                 130 tac aag aaa gcg gag cac gtg acc gac gtc gtg aaa cgc tgc ccc aac      547
Tyr Lys Lys Ala Glu His Val Thr Asp Val Val Lys Arg Cys Pro Asn
        135                 140                 145 cac gag ctc ggg agg gac ttc aac gaa gga cag tct gct cca gcc agc      595
His Glu Leu Gly Arg Asp Phe Asn Glu Gly Gln Ser Ala Pro Ala Ser
    150                 155                 160 cac ctc atc cgc gtg gaa ggc aat aat ctc tcg cag tat gtg gat gac      643
His Leu Ile Arg Val Glu Gly Asn Asn Leu Ser Gln Tyr Val Asp Asp
165                 170                 175                 180 cct gtc acc ggc agg cag agc gtc gtg gtg ccc tat gag cca cca cag      691
Pro Val Thr Gly Arg Gln Ser Val Val Val Pro Tyr Glu Pro Pro Gln
                185                 190                 195 gtg ggg acg gaa ttc acc acc atc ctg tac aac ttc atg tgt aac agc      739
Val Gly Thr Glu Phe Thr Thr Ile Leu Tyr Asn Phe Met Cys Asn Ser
            200                 205                 210 agc tgt gta ggg ggc atg aac cgg cgg ccc atc ctc atc atc atc acc      787
Ser Cys Val Gly Gly Met Asn Arg Arg Pro Ile Leu Ile Ile Ile Thr
        215                 220                 225 ctg gag atg cgg gat ggg cag gtg ctg ggc cgc cgg tcc ttt gag ggc      835
Leu Glu Met Arg Asp Gly Gln Val Leu Gly Arg Arg Ser Phe Glu Gly
```

-continued

```
                230                 235                 240
cgc atc tgc gcc tgt cct ggc cgc gac cga aaa gct gat gag gac cac     883
Arg Ile Cys Ala Cys Pro Gly Arg Asp Arg Lys Ala Asp Glu Asp His
245                 250                 255                 260 tac cgg gag cag cag gcc ctg aac gag agc tcc gcc aag aac ggg gcc     931
Tyr Arg Glu Gln Gln Ala Leu Asn Glu Ser Ser Ala Lys Asn Gly Ala
                265                 270                 275 gcc agc aag cgt gcc ttc aag cag agc ccc cct gcc gtc ccc gcc ctt     979
Ala Ser Lys Arg Ala Phe Lys Gln Ser Pro Pro Ala Val Pro Ala Leu
            280                 285                 290 ggt gcc ggt gtg aag aag cgg cgg cat gga gac gag gac acg tac tac    1027
Gly Ala Gly Val Lys Lys Arg Arg His Gly Asp Glu Asp Thr Tyr Tyr
        295                 300                 305 ctt cag gtg cga ggc cgg gag aac ttt gag atc ctg atg aag ctg aaa    1075
Leu Gln Val Arg Gly Arg Glu Asn Phe Glu Ile Leu Met Lys Leu Lys
    310                 315                 320 gag agc ctg gag ctg atg gag ttg gtg ccg cag cca ctg gtg gac tcc    1123
Glu Ser Leu Glu Leu Met Glu Leu Val Pro Gln Pro Leu Val Asp Ser
325                 330                 335                 340 tat cgg cag cag cag cag ctc cta cag agg ccg agt cac cta cag ccc    1171
Tyr Arg Gln Gln Gln Gln Leu Leu Gln Arg Pro Ser His Leu Gln Pro
                345                 350                 355 ccg tcc tac ggg ccg gtc ctc tcg ccc atg aac aag gtg cac ggg ggc    1219
Pro Ser Tyr Gly Pro Val Leu Ser Pro Met Asn Lys Val His Gly Gly
            360                 365                 370 atg aac aag ctg ccc tcc gtc aac cag ctg gtg ggc cag cct ccc ccg    1267
Met Asn Lys Leu Pro Ser Val Asn Gln Leu Val Gly Gln Pro Pro Pro
        375                 380                 385 cac agt tcg gca gct aca ccc aac ctg ggg ccc gtg ggc ccc ggg atg    1315
His Ser Ser Ala Ala Thr Pro Asn Leu Gly Pro Val Gly Pro Gly Met
    390                 395                 400 ctc aac aac cat ggc cac gca gtg cca gcc aac ggc gag atg agc agc    1363
Leu Asn Asn His Gly His Ala Val Pro Ala Asn Gly Glu Met Ser Ser
405                 410                 415                 420 agc cac agc gcc cag tcc atg gtc tcg ggg tcc cac tgc act ccg cca    1411
Ser His Ser Ala Gln Ser Met Val Ser Gly Ser His Cys Thr Pro Pro
                425                 430                 435 ccc ccc tac cac gcc gac ccc agc ctc gtc agt ttt tta aca gga ttg    1459
Pro Pro Tyr His Ala Asp Pro Ser Leu Val Ser Phe Leu Thr Gly Leu
            440                 445                 450 ggg tgt cca aac tgc atc gag tat ttc acc tcc caa ggg tta cag agc    1507
Gly Cys Pro Asn Cys Ile Glu Tyr Phe Thr Ser Gln Gly Leu Gln Ser
        455                 460                 465 att tac cac ctg cag aac ctg acc att gag gac ctg ggg gcc ctg aag    1555
Ile Tyr His Leu Gln Asn Leu Thr Ile Glu Asp Leu Gly Ala Leu Lys
    470                 475                 480 atc ccc gag cag tac cgc atg acc atc tgg cgg ggc ctg cag gac ctg    1603
Ile Pro Glu Gln Tyr Arg Met Thr Ile Trp Arg Gly Leu Gln Asp Leu
485                 490                 495                 500 aag cag ggc cac gac tac agc acc gcg cag cag ctg ctc cgc tct agc    1651
Lys Gln Gly His Asp Tyr Ser Thr Ala Gln Gln Leu Leu Arg Ser Ser
                505                 510                 515 aac gcg gcc acc atc tcc atc ggc ggc tca ggg gaa ctg cag cgc cag    1699
Asn Ala Ala Thr Ile Ser Ile Gly Gly Ser Gly Glu Leu Gln Arg Gln
            520                 525                 530 cgg gtc atg gag gcc gtg cac ttc cgc gtg cgc cac acc atc acc atc    1747
Arg Val Met Glu Ala Val His Phe Arg Val Arg His Thr Ile Thr Ile
        535                 540                 545 ccc aac cgc ggc ggc cca ggc ggc ggc cct gac gag tgg gcg gac ttc    1795
```

-continued

```
Pro Asn Arg Gly Gly Pro Gly Gly Pro Asp Glu Trp Ala Asp Phe
    550                 555                 560 ggc ttc gac ctg ccc gac tgc aag gcc cgc aag cag ccc atc aag gag      1843
Gly Phe Asp Leu Pro Asp Cys Lys Ala Arg Lys Gln Pro Ile Lys Glu
565                 570                 575                 580 gag ttc acg gag gcc gag atc cac tga                                   1870
Glu Phe Thr Glu Ala Glu Ile His
                585
```

<210> SEQ ID NO 17
<211> LENGTH: 588
<212> TYPE: PRT
<213> ORGANISM: Homo sapiens

<400> SEQUENCE: 17

```
Met Asp Val Phe His Leu Glu Gly Met Thr Thr Ser Val Met Ala Gln
1               5                   10                  15

Phe Asn Leu Leu Ser Ser Thr Met Asp Gln Met Ser Ser Arg Ala Ala
            20                  25                  30

Ser Ala Ser Pro Tyr Thr Pro Glu His Ala Ala Ser Val Pro Thr His
        35                  40                  45

Ser Pro Tyr Ala Gln Pro Ser Ser Thr Phe Asp Thr Met Ser Pro Ala
    50                  55                  60

Pro Val Ile Pro Ser Asn Thr Asp Tyr Pro Gly Pro His His Phe Glu
65                  70                  75                  80

Val Thr Phe Gln Gln Ser Ser Thr Ala Lys Ser Ala Thr Trp Thr Tyr
                85                  90                  95

Ser Pro Leu Leu Lys Lys Leu Tyr Cys Gln Ile Ala Lys Thr Cys Pro
            100                 105                 110

Ile Gln Ile Lys Val Ser Thr Pro Pro Pro Gly Thr Ala Ile Arg
        115                 120                 125

Ala Met Pro Val Tyr Lys Lys Ala Glu His Val Thr Asp Val Val Lys
    130                 135                 140

Arg Cys Pro Asn His Glu Leu Gly Arg Asp Phe Asn Glu Gly Gln Ser
145                 150                 155                 160

Ala Pro Ala Ser His Leu Ile Arg Val Glu Gly Asn Asn Leu Ser Gln
                165                 170                 175

Tyr Val Asp Asp Pro Val Thr Gly Arg Gln Ser Val Val Pro Tyr
            180                 185                 190

Glu Pro Pro Gln Val Gly Thr Glu Phe Thr Thr Ile Leu Tyr Asn Phe
        195                 200                 205

Met Cys Asn Ser Ser Cys Val Gly Gly Met Asn Arg Arg Pro Ile Leu
    210                 215                 220

Ile Ile Ile Thr Leu Glu Met Arg Asp Gly Gln Val Leu Gly Arg Arg
225                 230                 235                 240

Ser Phe Glu Gly Arg Ile Cys Ala Cys Pro Gly Arg Asp Arg Lys Ala
                245                 250                 255

Asp Glu Asp His Tyr Arg Glu Gln Gln Ala Leu Asn Glu Ser Ser Ala
            260                 265                 270

Lys Asn Gly Ala Ala Ser Lys Arg Ala Phe Lys Gln Ser Pro Pro Ala
        275                 280                 285

Val Pro Ala Leu Gly Ala Gly Val Lys Lys Arg Arg His Gly Asp Glu
    290                 295                 300

Asp Thr Tyr Tyr Leu Gln Val Arg Gly Arg Glu Asn Phe Glu Ile Leu
305                 310                 315                 320
```

```
Met Lys Leu Lys Glu Ser Leu Glu Leu Met Glu Leu Val Pro Gln Pro
            325                 330                 335

Leu Val Asp Ser Tyr Arg Gln Gln Gln Leu Leu Gln Arg Pro Ser
            340                 345                 350

His Leu Gln Pro Pro Ser Tyr Gly Pro Val Leu Ser Pro Met Asn Lys
            355                 360                 365

Val His Gly Gly Met Asn Lys Leu Pro Ser Val Asn Gln Leu Val Gly
            370                 375                 380

Gln Pro Pro His Ser Ser Ala Ala Thr Pro Asn Leu Gly Pro Val
385                 390                 395                 400

Gly Pro Gly Met Leu Asn Asn His Gly His Ala Val Pro Ala Asn Gly
            405                 410                 415

Glu Met Ser Ser Ser His Ser Ala Gln Ser Met Val Ser Gly Ser His
            420                 425                 430

Cys Thr Pro Pro Pro Tyr His Ala Asp Pro Ser Leu Val Ser Phe
            435                 440                 445

Leu Thr Gly Leu Gly Cys Pro Asn Cys Ile Glu Tyr Phe Thr Ser Gln
            450                 455                 460

Gly Leu Gln Ser Ile Tyr His Leu Gln Asn Leu Thr Ile Glu Asp Leu
465                 470                 475                 480

Gly Ala Leu Lys Ile Pro Glu Gln Tyr Arg Met Thr Ile Trp Arg Gly
            485                 490                 495

Leu Gln Asp Leu Lys Gln Gly His Asp Tyr Ser Thr Ala Gln Gln Leu
            500                 505                 510

Leu Arg Ser Ser Asn Ala Ala Thr Ile Ser Ile Gly Gly Ser Gly Glu
            515                 520                 525

Leu Gln Arg Gln Arg Val Met Glu Ala Val His Phe Arg Val Arg His
            530                 535                 540

Thr Ile Thr Ile Pro Asn Arg Gly Gly Pro Gly Gly Pro Asp Glu
545                 550                 555                 560

Trp Ala Asp Phe Gly Phe Asp Leu Pro Asp Cys Lys Ala Arg Lys Gln
            565                 570                 575

Pro Ile Lys Glu Glu Phe Thr Glu Ala Glu Ile His
            580                 585

<210> SEQ ID NO 18
<211> LENGTH: 1817
<212> TYPE: DNA
<213> ORGANISM: Homo sapiens

<400> SEQUENCE: 18
atggcccagt ccaccgccac ctcccctgat gggggcacca cgtttgagca cctctggagc      60
tctctggaac cagacagcac ctacttcgac cttccccagt caagccgggg gaataatgag     120
gtggtgggcg gaacggattc cagcatggac gtcttccacc tggagggcat gactacatct     180
gtcatggccc agttcaatct gctgagcagc accatggacc agatgagcag ccgcgcggcc     240
tcggccagcc cctacacccc agagcacgcc gccagcgtgc ccacccactc gccctacgca     300
caacccagct ccaccttcga caccatgtcg ccggcgcctg tcatcccctc aacaccgac      360 taccccggac ccaccacttt tgaggtcact ttccagcagt ccagcacggc caagtcagcc     420
acctggacgt actccccgct cttgaagaaa ctctactgcc agatcgccaa gcatgcccc      480 atccagatca aggtgtccac cccgccaccc ccaggcactg ccatccgggc catgcctgtt     540
tacaagaaag cggagcacgt gaccgacgtc gtgaaacgct gccccaacca cgagctcggg     600
```

-continued

```
agggacttca acgaaggaca gtctgctcca gccagccacc tcatccgcgt ggaaggcaat      660
aatctctcgc agtatgtgga tgaccctgtc accggcaggc agagcgtcgt ggtgccctat      720
gagccaccac aggtggggac ggaattcacc accatcctgt acaacttcat gtgtaacagc      780
agctgtgtag ggggcatgaa ccggcggccc atcctcatca tcatcaccct ggagatgcgg      840
gatgggcagg tgctgggccg ccggtccttt gagggccgca tctgcgcctg tcctggccgc      900
gaccgaaaag ctgatgagga ccactaccgg gagcagcagg ccctgaacga gagctccgcc      960
aagaacgggg ccgccagcaa gcgtgccttc aagcagagcc ccctgccgt ccccgccctt      1020
ggtgccggtg tgaagaagcg gcggcatgga cgaggacac cgtactacct tcaggtgcga       1080
ggccgggaga actttgagat cctgatgaag ctgaaagaga gcctggagct gatggagttg      1140
gtgccgcagc cactggtgga ctcctatcgg cagcagcagc agctcctaca gaggccgagt      1200
cacctacagc ccccgtccta cgggccggtc ctctcgccca tgaacaaggt gcacggggc      1260
atgaacaagc tgccctccgt caaccagctg gtgggccagc tcccccgca cagttccgga      1320
gctacaccca acctggggcc cgtgggcccc gggatgctca acaaccatgg ccacgcagtg      1380
ccagccaacg gcgagatgag cagcagccac agcgcccagt ccatggtctc ggggtcccac      1440
tgcactccgc caccccccta ccacgccgac cccagcctcg tcaggacctg ggggccctga      1500
agatccccga gcagtaccgc atgaccatct ggcggggcct gcaggacctg aagcagggcc      1560
acgactacag caccgcgcag cagctgctcc gctctagcaa cgcggccacc atctccatcg      1620
gcggctcagg ggaactgcag cgccagcggg tcatggaggc cgtgcacttc cgcgtgcgcc      1680
acaccatcac catccccaac cgcggcggcc caggcggcgg ccctgacgag tgggcggact      1740
tcggcttcga cctgcccgac tgcaaggccc gcaagcagcc catcaaggag gagttcacgg      1800
aggccgagat ccactga                                                    1817
```

<210> SEQ ID NO 19
<211> LENGTH: 499
<212> TYPE: PRT
<213> ORGANISM: Homo sapiens

<400> SEQUENCE: 19

```
Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160
```

-continued

```
Ile Gln Ile Lys Val Ser Thr Pro Pro Pro Gly Thr Ala Ile Arg
            165                 170                 175
Ala Met Pro Val Tyr Lys Lys Ala Glu His Val Thr Asp Val Val Lys
        180                 185                 190
Arg Cys Pro Asn His Glu Leu Gly Arg Asp Phe Asn Glu Gly Gln Ser
            195                 200                 205
Ala Pro Ala Ser His Leu Ile Arg Val Glu Gly Asn Asn Leu Ser Gln
    210                 215                 220
Tyr Val Asp Asp Pro Val Thr Gly Arg Gln Ser Val Val Pro Tyr
225                 230                 235                 240
Glu Pro Pro Gln Val Gly Thr Glu Phe Thr Thr Ile Leu Tyr Asn Phe
                245                 250                 255
Met Cys Asn Ser Ser Cys Val Gly Gly Met Asn Arg Arg Pro Ile Leu
            260                 265                 270
Ile Ile Ile Thr Leu Glu Met Arg Asp Gly Gln Val Leu Gly Arg Arg
        275                 280                 285
Ser Phe Glu Gly Arg Ile Cys Ala Cys Pro Gly Arg Asp Arg Lys Ala
    290                 295                 300
Asp Glu Asp His Tyr Arg Glu Gln Gln Ala Leu Asn Glu Ser Ser Ala
305                 310                 315                 320
Lys Asn Gly Ala Ala Ser Lys Arg Ala Phe Lys Gln Ser Pro Pro Ala
                325                 330                 335
Val Pro Ala Leu Gly Ala Gly Val Lys Lys Arg Arg His Gly Asp Glu
            340                 345                 350
Asp Thr Tyr Tyr Leu Gln Val Arg Gly Arg Glu Asn Phe Glu Ile Leu
        355                 360                 365
Met Lys Leu Lys Glu Ser Leu Glu Leu Met Glu Leu Val Pro Gln Pro
    370                 375                 380
Leu Val Asp Ser Tyr Arg Gln Gln Gln Leu Leu Gln Arg Pro Ser
385                 390                 395                 400
His Leu Gln Pro Pro Ser Tyr Gly Pro Val Leu Ser Pro Met Asn Lys
                405                 410                 415
Val His Gly Gly Met Asn Lys Leu Pro Ser Val Asn Gln Leu Val Gly
            420                 425                 430
Gln Pro Pro Pro His Ser Ala Ala Thr Pro Asn Leu Gly Pro Val
        435                 440                 445
Gly Pro Gly Met Leu Asn Asn His Gly His Ala Val Pro Ala Asn Gly
    450                 455                 460
Glu Met Ser Ser Ser His Ser Ala Gln Ser Met Val Ser Gly Ser His
465                 470                 475                 480
Cys Thr Pro Pro Pro Tyr His Ala Asp Pro Ser Leu Val Arg Thr
                485                 490                 495
Trp Gly Pro
```

<210> SEQ ID NO 20
<211> LENGTH: 17
<212> TYPE: DNA
<213> ORGANISM: Artificial
<220> FEATURE:
<223> OTHER INFORMATION: primer

<400> SEQUENCE: 20
gcgagctgcc ctcggag         17

```
<210> SEQ ID NO 21
<211> LENGTH: 19
<212> TYPE: DNA
<213> ORGANISM: Artificial
<220> FEATURE:
<223> OTHER INFORMATION: antisense primer

<400> SEQUENCE: 21
ggttctgcag gtgactcag                                                  19

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22
gccatgcctg tctacaag                                                   18

<210> SEQ ID NO 23
<211> LENGTH: 18
<212> TYPE: DNA
<213> ORGANISM: Artificial
<220> FEATURE:
<223> OTHER INFORMATION: antisense primer

<400> SEQUENCE: 23
accagctggt tgacggag                                                   18

<210> SEQ ID NO 24
<211> LENGTH: 21
<212> TYPE: DNA
<213> ORGANISM: Artificial
<220> FEATURE:
<223> OTHER INFORMATION: primer

<400> SEQUENCE: 24
gtcaaccagc tggtgggcca g                                               21

<210> SEQ ID NO 25
<211> LENGTH: 16
<212> TYPE: DNA
<213> ORGANISM: Artificial
<220> FEATURE:
<223> OTHER INFORMATION: antisense primer

<400> SEQUENCE: 25
gtggatctcg gcctcc                                                     16

<210> SEQ ID NO 26
<211> LENGTH: 17
<212> TYPE: DNA
<213> ORGANISM: Artificial
<220> FEATURE:
<223> OTHER INFORMATION: primer

<400> SEQUENCE: 26
aggccggcgt ggggaag                                                    17

<210> SEQ ID NO 27
<211> LENGTH: 19
<212> TYPE: DNA
<213> ORGANISM: Artificial
<220> FEATURE:
<223> OTHER INFORMATION: antisense primer
```

```
<400> SEQUENCE: 27
cttggcgatc tggcagtag                                                    19

<210> SEQ ID NO 28
<211> LENGTH: 17
<212> TYPE: DNA
<213> ORGANISM: Artificial
<220> FEATURE:
<223> OTHER INFORMATION: primer

<400> SEQUENCE: 28
gcggccacga ccgtgac                                                      17

<210> SEQ ID NO 29
<211> LENGTH: 18
<212> TYPE: DNA
<213> ORGANISM: Artificial
<220> FEATURE:
<223> OTHER INFORMATION: antisense primer

<400> SEQUENCE: 29
ggcagcttgg gtctctgg                                                     18

<210> SEQ ID NO 30
<211> LENGTH: 18
<212> TYPE: DNA
<213> ORGANISM: Artificial
<220> FEATURE:
<223> OTHER INFORMATION: primer

<400> SEQUENCE: 30
ctgtacgtcg gtgacccc                                                     18

<210> SEQ ID NO 31
<211> LENGTH: 18
<212> TYPE: DNA
<213> ORGANISM: Artificial
<220> FEATURE:
<223> OTHER INFORMATION: antisense primer

<400> SEQUENCE: 31
tcagtggatc tcggcctc                                                     18

<210> SEQ ID NO 32
<211> LENGTH: 18
<212> TYPE: DNA
<213> ORGANISM: Artificial
<220> FEATURE:
<223> OTHER INFORMATION: primer

<400> SEQUENCE: 32
aggggacgca gcgaaacc                                                     18

<210> SEQ ID NO 33
<211> LENGTH: 19
<212> TYPE: DNA
<213> ORGANISM: Artificial
<220> FEATURE:
<223> OTHER INFORMATION: antisense primer

<400> SEQUENCE: 33
ccatcagctc caggctctc                                                    19

<210> SEQ ID NO 34
<211> LENGTH: 18
```

```
<212> TYPE: DNA
<213> ORGANISM: Artificial
<220> FEATURE:
<223> OTHER INFORMATION: antisense primer

<400> SEQUENCE: 34
ccaggacagg cgcagatg                                                 18

<210> SEQ ID NO 35
<211> LENGTH: 19
<212> TYPE: DNA
<213> ORGANISM: Artificial
<220> FEATURE:
<223> OTHER INFORMATION: antisense primer

<400> SEQUENCE: 35
gatgaggtgg ctggctgga                                                19

<210> SEQ ID NO 36
<211> LENGTH: 19
<212> TYPE: DNA
<213> ORGANISM: Artificial
<220> FEATURE:
<223> OTHER INFORMATION: antisense primer

<400> SEQUENCE: 36
tggtcaggtt ctgcaggtg                                                19

<210> SEQ ID NO 37
<211> LENGTH: 18
<212> TYPE: DNA
<213> ORGANISM: Artificial
<220> FEATURE:
<223> OTHER INFORMATION: primer

<400> SEQUENCE: 37
cacctactcc agggatgc                                                 18

<210> SEQ ID NO 38
<211> LENGTH: 21
<212> TYPE: DNA
<213> ORGANISM: Artificial
<220> FEATURE:
<223> OTHER INFORMATION: antisense primer

<400> SEQUENCE: 38
aggaaaatag aagcgtcagt c                                             21

<210> SEQ ID NO 39
<211> LENGTH: 18
<212> TYPE: DNA
<213> ORGANISM: Artificial
<220> FEATURE:
<223> OTHER INFORMATION: primer

<400> SEQUENCE: 39
caggcccact tgcctgcc                                                 18

<210> SEQ ID NO 40
<211> LENGTH: 19
<212> TYPE: DNA
<213> ORGANISM: Artificial
<220> FEATURE:
<223> OTHER INFORMATION: antisense primer

<400> SEQUENCE: 40
```

```
ctgtccccaa gctgatgag                                                  19
```

<210> SEQ ID NO 41
<211> LENGTH: 15
<212> TYPE: DNA
<213> ORGANISM: Artificial
<220> FEATURE:
<223> OTHER INFORMATION: primer

<400> SEQUENCE: 41

```
cccccccccc ccccd                                                      15
```

<210> SEQ ID NO 42
<211> LENGTH: 16
<212> TYPE: DNA
<213> ORGANISM: Artificial
<220> FEATURE:
<223> OTHER INFORMATION: primer

<400> SEQUENCE: 42

```
cccccccccc cccccd                                                     16
```

<210> SEQ ID NO 43
<211> LENGTH: 1400
<212> TYPE: DNA
<213> ORGANISM: Cebus apella

<400> SEQUENCE: 43

```
ggggctccgg ggacacttgg cgtccgggct ggaagcgtgc tttccaagac ggtgacacgc     60
ttccctgagg attggcagcc agactgctta cgggtcactg ccatggagga gccgcagtca    120
gatcccagca tcgagccccc tctgagtcag gaaacatttt cagacctatg gaaactactt    180
cctgaaaaca acgttctgtc ccccttgccg tcccaagcgg tggatgattt gatgctctct    240
ccggatgatc ttgcacaatg gttaactgaa gacccaggtc cagatgaagc tcccagaatg    300
tcagaggctg ctccccacat ggcccccaca ccagcagctc ctacaccggc ggcccctgca    360
ccagccccct cctggcccct gtcatcctct gtcccttccc agaaaaccta ccacggcagc    420
tacggttttc gtctgggctt cctgcattct ggaacagcca agtctgtgac ttgcacgtac    480
tccccctgacc tcaacaagat gttttgccag ctggccaaga cctgcccgcgt gcagctgtgg    540
gttgattcca caccccgcc cggcagccgc gtccgcgcca tggccatcta caagcagtca    600
cagcacatga ctgaggtcgt gaggcgctgc ccccaccatg agcgctgctc agacagcgat    660
ggactggccc ctcctcaaca tcttatccga gtggaaggaa atttgcgtgt ggagtattcg    720
gatgacagaa acactttcg acatagtgtg gtggtgccct atgagccgcc tgaggttggc    780
tctgactgta ccaccatcca ctacaactac atgtgtaaca gttcctgcat gggcggcatg    840
aaccggaggc ccatcctcac aattatcaca ctggaagact ccagtggtaa tctactggga    900
cggaacagct ttgaggtgcg agtttgtgcc tgtcctggga gagaccggcg cacagaggaa    960
gagaatttcc gcaagaaagg ggagccttgc cacgagctgc cccctgggag cactaagcga   1020
gcactgccca caacaccag ctcctctccc cagccaaaga agaaaccact ggatggaaa     1080
tatttcaccc ttcagatccg cgggcgtgag cgcttcgaga tgttccgaga gctgaatgag   1140
gccttggaac tcaaggatgc ccaggctggg aaagagccag cggggagcag ggctcactcc   1200
agccacctga agtccaagaa ggggcaatct acctcccgcc ataaaaaatt catgttcaag   1260
acagaggggc ctgactcaga ctgacattct cagcttcttg ttccccccact gagcctccca   1320
cccccatctc tccctcccct gccatttgna gttctgggtc tttaaaccct tgcttgcaat   1380
```
aggtgtgtgt cagaagcaaa                                           1400

<210> SEQ ID NO 44
<211> LENGTH: 393
<212> TYPE: PRT
<213> ORGANISM: Cebus apella

<400> SEQUENCE: 44

```
Met Glu Glu Pro Gln Ser Asp Pro Ser Ile Glu Pro Leu Ser Gln
1               5                   10                  15

Glu Thr Phe Ser Asp Leu Trp Lys Leu Pro Glu Asn Asn Val Leu
            20                  25                  30

Ser Pro Leu Pro Ser Gln Ala Val Asp Asp Leu Met Leu Ser Pro Asp
            35                  40                  45

Asp Leu Ala Gln Trp Leu Thr Glu Asp Pro Gly Pro Asp Glu Ala Pro
    50                  55                  60

Arg Met Ser Glu Ala Ala Pro His Met Ala Thr Pro Ala Ala Pro
65                  70                  75                  80

Thr Pro Ala Ala Pro Ala Pro Ala Pro Ser Trp Pro Leu Ser Ser
                85                  90                  95

Val Pro Ser Gln Lys Thr Tyr His Gly Ser Tyr Gly Phe Arg Leu Gly
                100                 105                 110

Phe Leu His Ser Gly Thr Ala Lys Ser Val Thr Cys Thr Tyr Ser Pro
            115                 120                 125

Asp Leu Asn Lys Met Phe Cys Gln Leu Ala Lys Thr Cys Pro Val Gln
    130                 135                 140

Leu Trp Val Asp Ser Thr Pro Pro Gly Ser Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Ser Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Phe Arg Lys Lys Gly Glu Pro Cys His Glu Leu Pro Pro Gly Ser Thr
    290                 295                 300

Lys Arg Ala Leu Pro Asn Asn Thr Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Ala Gly Ser Arg Ala His Ser Ser His
        355                 360                 365
```

Leu Lys Ser Lys Lys Gly Gln Ser Thr Ser Arg His Lys Lys Phe Met
    370                 375                 380

Phe Lys Thr Glu Gly Pro Asp Ser Asp
385                 390

<210> SEQ ID NO 45
<211> LENGTH: 393
<212> TYPE: PRT
<213> ORGANISM: Homo sapiens

<400> SEQUENCE: 45

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Gly Thr Arg Val Arg Ala Met Ala
145                 150                 155                 160

Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp

```
                    340                 345                 350
Ala Gln Gln Gly Lys Glu Pro Gly Gly Arg Ser Ala His Ser Ser His
        355                 360                 365
Leu Lys Ser Lys Lys Gly Gln Ser Thr Ser Arg His Lys Lys Leu Met
    370                 375                 380
Phe Lys Thr Glu Gly Pro Asp Ser Asp
385                 390
```

<210> SEQ ID NO 46
<211> LENGTH: 889
<212> TYPE: DNA
<213> ORGANISM: Homo sapiens

<400> SEQUENCE: 46

```
cacctactcc agggatgccc caggcaggcc cacttgcctg ccgcccccac cgaggctgtc        60
acaggaggac agagcacgag ttcccagggt gctcaggtgt cattccttcc ttcctgcaga       120
gcgagctgcc ctcggaggcc ggcgtgggga agatggccca gtccaccgcc acctcccctg       180
atggggcac cacgtttgag cacctctgga gctctctgtg agtgcgcttg gctggcaga        240
gctgggggcc cccctgggag gcactctggg ctagcctcag ccaccttcgc tgggctaact       300
gggccagagc aggaggggtg gccccgggag gactctgggc tagccccagc caccctcact       360
gagactttgg gctaaacttg gcaaccctca ctgggattct gggctagcct cgaccaccct       420
tgctgcacta actggaccag agcaggagag gtggctccac actagtcttg ggctagcctt       480
agccaccctc atcagcttgg ggacagggcg ggtcggaggg gcaggaaga gggactgctg        540
ccctaggcct tccctgggga tgcaggacca aaattcagac tctttttctct ggccagctct      600
ggagagggcc catggccagc agaggcccag aataacagag cccatgactg gctctgcctc       660
tctggcactc acagcagccc tggaatggca ggtggaggac agagatggga tgagagggaa       720
tgggaagggc aggagacgta ggcctcacca ggagtctcag gctagccttg agctctgggc       780
ctgggaggta ttggggtgac acccaaactg gggactgacg cttctatttt cctctccctg       840
ccccagggaa ccagacagca cctacttcga ccttccccag tcaagccgg                  889
```

<210> SEQ ID NO 47
<211> LENGTH: 23
<212> TYPE: DNA
<213> ORGANISM: Artificial
<220> FEATURE:
<223> OTHER INFORMATION: primer comprising BamHI site

<400> SEQUENCE: 47

```
gatccgggcc ctttttttttt ttt                                              23
```

<210> SEQ ID NO 48
<211> LENGTH: 20
<212> TYPE: DNA
<213> ORGANISM: Artificial
<220> FEATURE:
<223> OTHER INFORMATION: primer comprising ApaI site

<400> SEQUENCE: 48

```
aaaaaaaaaa aaagggcccg                                                   20
```

<210> SEQ ID NO 49
<211> LENGTH: 26
<212> TYPE: DNA
<213> ORGANISM: Artificial

```
<220> FEATURE:
<223> OTHER INFORMATION: primer comprising KpnI site

<400> SEQUENCE: 49
actggtaccg cgagctgccc tcggag                                    26

<210> SEQ ID NO 50
<211> LENGTH: 28
<212> TYPE: DNA
<213> ORGANISM: Artificial
<220> FEATURE:
<223> OTHER INFORMATION: antisense primer comprising Xba I site

<400> SEQUENCE: 50
gactctagag gttctgcagg tgactcag                                  28

<210> SEQ ID NO 51
<211> LENGTH: 19
<212> TYPE: DNA
<213> ORGANISM: Artificial
<220> FEATURE:
<223> OTHER INFORMATION: primer

<400> SEQUENCE: 51
gagcatgtga ccgacattg                                            19

<210> SEQ ID NO 52
<211> LENGTH: 30
<212> TYPE: DNA
<213> ORGANISM: Artificial
<220> FEATURE:
<223> OTHER INFORMATION: primer comprising BamHI site

<400> SEQUENCE: 52
tttggatccg tcaaccagct ggtgggccag                                30

<210> SEQ ID NO 53
<211> LENGTH: 25
<212> TYPE: DNA
<213> ORGANISM: Artificial
<220> FEATURE:
<223> OTHER INFORMATION: antisense primer comprising a Sal I site

<400> SEQUENCE: 53
aaagtcgacg tggatctcgg cctcc                                     25

<210> SEQ ID NO 54
<211> LENGTH: 27
<212> TYPE: DNA
<213> ORGANISM: Artificial
<220> FEATURE:
<223> OTHER INFORMATION: primer

<400> SEQUENCE: 54
tatctcgagc tgtacgtcgg tgacccc                                   27

<210> SEQ ID NO 55
<211> LENGTH: 27
<212> TYPE: DNA
<213> ORGANISM: Artificial
<220> FEATURE:
<223> OTHER INFORMATION: antisense primer

<400> SEQUENCE: 55
atatctagat cagtggatct cggcctc                                   27
```

The invention claimed is:

1. An isolated nucleic acid sequence coding for a polypeptide comprising amino acid sequence SEQ ID NO:6.

2. An isolated nucleic acid sequence coding for a polypeptide consisting essentially of amino acid sequence SEQ ID NO:6.

3. An isolated nucleic acid sequence coding for a polypeptide comprising the amino acid sequence from residue 111 to residue 309 of SEQ ID NO:6.

4. A cloning or expression vector comprising a nucleic acid sequence according to claim 1.

5. A vector, according to claim 4, which is plasmid pSE1.

6. An isolated host cell transfected by a vector according to claim 5.

7. A transfected host cell, according to claim 6 which is *E. coli* MC 1061.

* * * * *

UNITED STATES PATENT AND TRADEMARK OFFICE
CERTIFICATE OF CORRECTION

| | | |
|---|---|---|
| PATENT NO. | : 7,838,648 B2 | Page 1 of 2 |
| APPLICATION NO. | : 12/464274 | |
| DATED | : November 23, 2010 | |
| INVENTOR(S) | : Daniel Caput et al. | |

It is certified that error appears in the above-identified patent and that said Letters Patent is hereby corrected as shown below:

Title Page, Item (56), in column 2, under "Other Publications", line 1, delete "Termainal" and insert -- Terminal --, therefor.

On the Title Page, in item (56), in column 2, under "Other Publications", line 39, delete "gnes" and insert -- genes --, therefor.

On the Title Page, in item (56), in column 2, under "Other Publications", line 45, delete "Ca2'" and insert -- Ca2+ --, therefor.

On Title page 2, in column 1, under "Other Publications", line 6, delete "Expressio" and insert -- Expression --, therefor.

On Title page 2, in column 1, under "Other Publications", line 7, delete "alpa" and insert -- alpha --, therefor.

On Title page 2, in column 1, under "Other Publications", line 7, delete "Progession" and insert -- Progression --, therefor.

On Title page 2, in column 1, under "Other Publications", line 12, delete "Pendered syndrom" and insert -- Pendred syndrome --, therefor.

On Title page 2, in column 2, under "Other Publications", line 12, delete "continguous" and insert -- contiguous --, therefor.

In column 3, line 41, delete "cDNAS" and insert -- cDNAs --, therefor.

In column 12, line 30, delete "4 nl" and insert -- 4 µl --, therefor.

In column 15, line 37, delete "p8," and insert -- pH 8, --, therefor.

Signed and Sealed this
Eighth Day of March, 2011

David J. Kappos
*Director of the United States Patent and Trademark Office*

CERTIFICATE OF CORRECTION (continued)
U.S. Pat. No. 7,838,648 B2

In column 15, line 47, delete "11.3" and insert -- II.3 --, therefor.

In column 15, line 60, delete "50)" and insert -- 51). --, therefor.

In column 22, line 58, delete "4'µl'" and insert -- 4 µl --, therefor.

In column 22, line 61, delete "1.3.d," and insert -- I.3.d --, therefor.

In column 24, line 31, delete "593" and insert -- 503 --, therefor.

In column 25, line 24, below "FIG. 13)."
insert -- The reaction is carried out for 30 cycles as described in EXAMPLE VIII.3. --.

In column 25, line 50, delete "$A^{-20}/T^{-20}$" and insert -- $A^{-30}/T^{-20}$ --, therefor.

In column 26, line 29, delete "(R→E)" and insert -- (R→H) --, therefor.